United States Patent
Verroust et al.

(10) Patent No.: US 6,586,389 B1
(45) Date of Patent: Jul. 1, 2003

(54) CUBILIN PROTEIN, DNA SEQUENCES ENCODING CUBILIN AND USES THEREOF

(75) Inventors: Pierre J. Verroust, Paris (FR); Timothy G. Hammond, New Orleans, LA (US)

(73) Assignee: Administrators of the Tulane Educational Fund, New Orleans, LA (US)

(*) Notice: Subject to any disclaimer, the term of this patent is extended or adjusted under 35 U.S.C. 154(b) by 0 days.

(21) Appl. No.: 09/341,461

(22) PCT Filed: Jan. 21, 1999

(86) PCT No.: PCT/US99/01259

§ 371 (c)(1), (2), (4) Date: Jul. 20, 2000

(87) PCT Pub. No.: WO99/37757

PCT Pub. Date: Jul. 29, 1999

Related U.S. Application Data

(60) Provisional application No. 60/072,197, filed on Jan. 22, 1998, now abandoned.

(51) Int. Cl.[7] .............................................. A61K 38/17
(52) U.S. Cl. ........................................... 514/2; 530/350
(58) Field of Search .......................... 530/350; 536/23.1; 514/2

(56) References Cited

U.S. PATENT DOCUMENTS 5,447,860 A * 9/1995 Ziegler .................... 435/240.1

OTHER PUBLICATIONS

Coffman, Genbank P21783, , May 1, 1991.*
Verroust, P. J.; et al, Vitamin B12 B12–Proteins, Lect. Eur. Symp., 4th (1998), Meeting Date 1996, 491–504. Editor(s): Kraeutler, Bernhard; Arigoni, Duilio; Golding Bernard T. Publisher: Wiley–VCH Verlag GmbH, Weinheim, Germany.*

* cited by examiner

Primary Examiner—Lorraine Spector
Assistant Examiner—Eliane Lazar-Wesley
(74) Attorney, Agent, or Firm—Benjamin Aaron Adler

(57) ABSTRACT

The present invention provides novel renal receptors for ligands. Cubilin and megalin are representative examples of such renal receptors. Also provided are potential uses of these renal receptors for treating toxicity in various tissues and for detecting renal damage.

5 Claims, 26 Drawing Sheets

```
 -20 MSSQFLWGFV TLLMIAELDG KTGKPEQRGQ KRIADLHQPR MTTEEGNLVF
                                                          *
  31 LTSSTQNIEF RTGSLGKIKL NDEDLGECLH QIQRNKDDII DLRKNTTGLP
  81 QNILSQVHQL NSKLVDLERD FQNLQQNVER KVCSSNPCLN GGTCVNLHDS
 131 FVCICPSQWK GLFCSEDVNE CVVYSGTPFG CQSGSTCVNT VGSFRCDCTP
 181 DTYGPQCASK YNDCEQGSKQ LCKHGICEDL QRVHHGQPNF HCICDAGWTT
 231 PPNGISCTED KDECSLQPSP CSEHAQCFNT QGSFYCGACP KGWQGNGYEC
 281 QDINECEINN GGCSQAPLVP CLNTPGSFSC GNCPAGFSGD GRVCTPVDIC
 331 SIHNGGCHPE ATCSSSPVLG SFLPVCTCPP GYTGNGYGSN GCVRLSNICS
                                     *
 381 RHPCVNGQCI ETVSSYFCKC DSGWSGQNCT ENINDCSSNP CLNGGTCIDG
                                                          *
 431 INGFTCDCTS SWTGYYCQTP QAACGGILSG TQGTFAYHSP NDTYIHNVNC
 481 FWIVRTDEEK VLHVTFTFFD LESASNCPRE YLQIHDGDSS ADFPLGRYCG
 531 SRPPQGIHSS ANALYFHLYS EYIRSGRGFT ARWEAKLPEC GGILTDNYGS
 581 ITSPGYPGNY PPGRDCVWQV LVNPNSLITF TFGTLSLESH NDCSKDYLEI
 631 RDGPFHQDPV LGKFCTSLST PPLKTTGPAA RIHFHSDSET SDKGFHITYL
                        *                                 *
 681 TTQSDLDCGG NYTDTDGELL LPPLSGPFSH SRQCVYLITQ AQGEQIVINF
                                               *
 731 THVELESQMG CSHTYIEVGD HDSLLRKICG NETLFPIRSV SNKVWIRLRI
 781 DALVQKASFR ADYQVACGGM LRGEGFFRSP FYPNAYPGRR TCRWTISQPQ
               *
 831 RQVVLLNFTD FQIGSSASCD TDYIEIGPSS VLGSPGNEKF CSSNIPSFIT
 881 SVYNILYVTF VKSSSMENRG FTAKFSSDKL ECGEVLTAST GIIESPGHPN
               *                                *
 931 VYPRGVNCTW HVVVQRGQLI RLEFSSFYLE FHYNCTNDYL EIYDTAAQTF
 981 LGRYCGKSIP PSLTSNSNSI KLIFVSDSAL AHEGFSINYE AIDASSVCLY
1031 DYTDNFGMLS SPNFPNNYPS NWECIYRITV GLNQQIALHF TDFTLEDYFG
1081 SQCVDFVEIR DGGYETSPLV GIYCGSVLPP TIISHSNKLW LKFKSDAALT
                        *
1131 AKGFSAYWDG SSTGCGGNLT TPQVLTSPNY PMPYYHSSEC YWRLEASHGS
1181 PFELEFQDFH LEHHPSCSLD YLGRVDGPTT NSRLIDKLCG DTTPAPIRSN
                                                *
1231 KDVVLLKTEE LMQGQLGRGF EINFRQRCDN VVIVNKTFGI LESINYPNPY
```

Fig. 3A

```
                *                    *                    *
1281 DKNQRCNWTI QATTGNTVNY TFLGFDVESY MNCSTDYVEL YDGPQWMGRY
1331 CGNNMPPPGA TTGSQLHVLF HTDGINSGEK GFKMQWFTHG CGGEMSGTAG
1381 SFSSPGYPNS YPHNKECIWN IRVAPGSSIQ LTIHDFDVEY HTSCNYDSLE
                                                                  *
1431 IYAGLDFNSP RIAQLCSQSP SANPMQVSST GNELAIRFKT DSTLNGRGFN
1481 ASWRAVPGGC GGIIQLSRGE IHSPNYPNNY RANTECSWII QVERHHRVLL
        *
1531 NITDFDLEAP DSCLRLMDGS SSTNARVASV CGRQQPPNSI IASGNSLFVR
                                                                  *
1581 FRSGSSSQNR GFRAEFREEC GGRIMTDSSD TIFSPLYPHN YLHNQNCSWI
                                       *
1631 IEAQPPFNHI TLSFTHFQLQ NSTDCTRDFV EILDGNDYDA PVQGRYCGFS
1681 LPHPIISFGN ALTVRFVTDS TRSFEGFRAI YSASTSSCGG SFYTLDGIFN
1731 SPDYPADYHP NAECVWNIAS SPGNRLQLSF LSFNLENSLN CNKDFVEIRE
        *                    *
1781 GNATGHLIGR YCGNSLPGNY SSAEGHSLWV RFVSDGSGTG MGFQARFKNI
1831 FGNNNIVGTH GKIASPFWPG KYPYNSNYKW VVNVDAYHII HGRILEMDIE
1881 PTTNCFYDSL KIYDGFDTHS RLIGTYCGTQ TESFSSSRNY LTFQFSSDSS
1931 VSGRGFLLEW FAVDVSDSTP PTIAPGACGG FMVTGDTPVH IFSPGWPREY
1981 ANGADCIWII YAPDSTVELN ILSLDIEPQQ SCNYDKLIVK DGDSDLSPEL
                                                     *
2031 AVLCGVSPPG PIRSTGEYMY IRFTSDTSVA GTGFNASFHK SCGGYLHADR
                                *
2081 GVITSPKYPD TYLPNLNCSW HVLVQTGLTI AVHFEQPFQI QNRDSFCSQG
2131 DYLVLRNGPD NHSPPLGPSG RNGRFCGMYA PSTLFTSGNE MFVQFISDSS
2181 NGGQGFKIRY EAKSLACGGT VYIHDADSDG YLTSPNYPAN YPQHAECIWI
                                                     *
2231 LEAPPGRSIQ LQFEDQFNIE DTPNCSVSYL ELRDGANSNA RLVSKLCGHT
2281 LPHSWVSSRE RIYLKFHTDG GSSYMGFKAK YSIASCGGTV SGDSGVIESI
                                                                  *
2331 GYPTLPYANN VFCQWFIRGL PGHYLTLSFE DFNLQSSPGC TKDFVEIWEN
2381 HTSGRVLGRY CGNSTPSSVD TSSNVASVKF VTDGSVTASG FRLQFKSSRQ
2431 VCGGDLHGPT GTFTSPNYPN PNPHARICEW TITVQEGRRI VLTFTNLRLS
                                                     *
2481 TQPSCNSEHL IVFNGIRSNS PLLQKLCSRV NVTNEFKSSG NTMKVVFFTD
```

Fig. 3B

```
                                           *
2531 GSRPYGGFTA SYTSTEDAVC GGFLPSVSGG NFSSPGYNGI RDYARNLDCE
             *
2581 WTLSNPNREN SSISIYFLEL SIESHQDCTF DVLEFRVGDA DGPLIEKFCS
2631 LSAPTAPLVI PYPQVWIRFV SNERVEYTGF YIEYSFTDCG GIRTGDNGVI
2681 SSPNYPNLYS AWTHCSWLLK APEGHTITLT LSDFLLEAHP TCTSDSVTVR
2731 NGDSPGSPVI GRYCGQSVPR PIQSGSNQLI VTFNTNNQGQ TRGFYATWTT
                      *
2781 NALGCGGTFH SANGTIKSPH WPQTFPENSR CSWTVITHDS KHWEISFDSN
                                              *
2831 FRIPSSDSQC QNSFVKVWGG RLMINKTLLA TSCGDVAPSP IVTSGNIFTA
                                                         *
2881 VFQSEEMAAQ GFSASFISRC GRTFNTSPGD IISPNFPKQY DNNMNCTYLI
                                                *
2931 DADPQSLVIL TFVSFHLEDR SAITGTCDHD GLHIIKGRNL SSTPLVTICG
                                                         *
2981 SETLRPLTVD GPVLLNFYSD AYTTDFGFKI SYRAITCGGI YNESSGILRS
3031 PSYSYSNYPN NLYCVYSLHV RSSRVIIIRF NDFDVAPSNL CAHDFLEVFD
              *                    *
3081 GPSIGNRSLG KFCGSTRPQT VKSTNSSLTL LFKTDSSQTA RGWKIFFRET
                       *
3131 IGPQQGCGGY LTEDNQSFVS PDSDSNGRYD KGLSCIWYIV APENKLVKLT
3181 FNVFTLEGPS SAGSCVYDYV QIADGASINS YLGGKFCGSR MPAPFISSGY
                      *                        *         *
3231 FLTFQFVSDV TVEMRGFNAT YTFVDMPCGG TYNATSTPQN ASSPHLSNIG
3281 RPYSTCTWVI AAPPQQQVQI TVWDLQLPSQ DCSQSYLELQ DSVQTGGNRV
             *                                            *
3331 TQFCGANYTT LPVFYSSMST AVVVFKSGVL NRNSQVQFSY QIADCNREYN
                                          *
3381 QTFGNLKSPG WPQNYDNNLD CTIILRAPQN HSISLFFYWF QLEDSRQCMN
3431 DFLEVRNGGS STSPLLDKYC SNLLPNPVFS QSNELYLHFH SDHSVTNNGY
                                                 *
3481 EIIWTSSAAG CGGTLLGDEG IFTNPGFPDS YPNNTHCEWT IVAPSGRPVS
3531 VGFPFLSIDS SGGCDQNYLI VFNGPDANSP PFGPLCGINT GIAPFYASSN
3581 RVFIRFHAEY TTRLSGFEIM WSS    SEQ ID NO: 2
```

Fig. 3C

| # | Name | Sequence | |
|---|---|---|---|
| 1 | Cubilin-egf1 | RKV..CS.....SNPC..LNGGTCVNL..H..DSF | |
| 2 | Cubilin-egf2 | EDVNECVVYSGTPFGCQ..SGSTCVNT..V..GSF | |
| 3 | Cubilin-egf3 | SKYNDCE..QGSKQLCKH...GICEDLQRVHHGQP | |
| 4 | Cubilin-egf4 | EDKDECSL.Q..PSPCSEH..AQCFNT...Q..GSF | |
| 5 | Cubilin-egf5 | ~DINKCEI.N..NGGCSQAPLVPCLNT..P..GSF | |
| 6 | Cubilin-egf6 | ~PVDICSIHN...GGC..HPEATCSSSPVL..GSF | |
| 7 | Cubilin-egf7 | RLSNICS.....RHPC..VN.GQCIET..V..SSY | |
| 8 | Cubilin-egf8 | ENINDCS.....SNPC..LNGGTCIDG..I..NGF | |
| 9 | Bmp-1-egf1 | ~EVDECSRPN..RGGCEQR....CLNT..L..GSY | |
| 10 | Tolloid-egf1 | ~DVDECKF.T..DHGCQHL....CINT..L..GSY | |
| 11 | Tolloid-egf2 | ~DVDECSM.N..NGGCQHR....CRNT..F..GSY | |
| 12 | C1s-egf1 | ~DINECT..DFVDVPCSH....FCNNF..I..GGY | |
| 13 | Fibrillin-egf5 | ~DIDECSTIPGI...CE..GGE.CTNT..V..SSY | |
| 14 | Fibrillin-egf13 | ~DIDEC.E.SSP....CI..NGV.CKNS..P..GSF | |
| 15 | Fibrillin-egf26 | ~DVNECLD.PTT...CI..SGN.CVNT..P..GSY | |

| # | Name | Sequence | SEQ ID NO |
|---|---|---|---|
| 1 | Cubilin-egf1 | ..VC.ICPSQW....KGLF.CS | SEQ ID NO 6 |
| 2 | Cubilin-egf2 | ..RC.DCTPDTY.GPQ....CA | SEQ ID NO 7 |
| 3 | Cubilin-egf3 | NFHC.ICDAGWTTPPNGI.SCT | SEQ ID NO 8 |
| 4 | Cubilin-egf4 | ..YCGACPKGW..QGNGYE.CQ | SEQ ID NO 9 |
| 5 | Cubilin-egf5 | ..SCGNCPAGF..SGDGRV.CT | SEQ ID NO 10 |
| 6 | Cubilin-egf6 | LPVCT.CPPGYTGNGYGSNGCV | SEQ ID NO 11 |
| 7 | Cubilin-egf7 | ..FC.KCDSGW....SGQN.CT | SEQ ID NO 12 |
| 8 | Cubilin-egf8 | ..TC.DCTSSW....TGYY.CQ | SEQ ID NO 13 |
| 9 | Bmp-1-egf1 | ..KCS.CDPGYELAPDKRR.CE | SEQ ID NO 14 |
| 10 | Tolloid-egf1 | ..QCG.CRAGYELQANGKT.CE | SEQ ID NO 15 |
| 11 | Tolloid-egf2 | ..QCS.CRNGYTLAENGHN.CT | SEQ ID NO 16 |
| 12 | C1s-egf1 | ..FCS.CPPEYFLHDDMKN.CG | SEQ ID NO 17 |
| 13 | Fibrillin-egf5 | ..FC.KCPPGFYTSPDGTR.CI | SEQ ID NO 18 |
| 14 | Fibrillin-egf13 | ..IC.ECSSESTLDPTKTI.CI | SEQ ID NO 19 |
| 15 | Fibrillin-egf26 | ..IC.DCPPDFELNPTRVG.CV | SEQ ID NO 20 |

| Residues for | D DE | | D | Y |
|---|---|---|---|---|
| Ca²⁺ binding | N NQ | | N | F |

Fig. 6A

| | | | | |
|---|---|---|---|---|
| 1 Cubilin-CUB2 | CGGIL....TDNYGSITSPGYPGN.YPP.GRDCVWQVLVNPNSLI |
| 2 Cubilin-CUB5 | CGEVL....TASTGIIESPGHPNV.YPR.GVNCTWHVVQRGQLI |
| 3 Cubilin-CUB6 | C...LYDYTDNFGMLSSPNFPN.NYPS.NWECIYRITVGLNQQI |
| 4 Cubilin-CUB9 | CGG....EMSGTAGSFSSPGYPNS.YPH.NKECIWNIRVAPGSSI |
| 5 Cubilin-CUB12 | CGGSF....YTLDGIFNSPDYPA.DYHP.NAECVWNIASSPGNRL |
| 6 Cubilin-CUB17 | CGGTV....SGDSGVIESIGYPTLPYAN.NVFCQWFIRGLPGHYL |
| 7 Cubilin-CUB20 | CGG....IRTGDNGVISSPNYPNL.YSA.WTHCSMLLKAPEGHTI |
| 8 Bmp-1-CUB1 | CGETLQDSTGNF..SSPEYPN.GYSA.HMHCVWRISVTPGEKI |
| 9 Bmp-1-CUB2 | CGGDV.K..KDYGHIQSPNYP.DDYRP.SKVCIWRIQVSEGFHV |
| 10 Tolloid-CUB2 | CGGDL.KLTKDQS.IDSPNYP.MDYMP.DKECVWRITAPDNHQV |
| 11 Tolloid-CUB3 | CGGVV.DATKSNGSLYSPSYPDV.YPN.SKQCVWEVVAPPNHAV |
| 12 Tolloid-CUB4 | C...KF.EITTSYGVLQSPNYP.EDYPR.NIYCYWHFQTVLGHRI |
| 13 Uvs-2-CUB2 | CGGAFYSSPKT....FTSPNYPG.NYTT.NTNCTWTITAPAGFKV |
| 14 C1s-CUB1 | ~~~~~~EPTMYGEILSPNYPQA.YPS.EVEKSWDIEVPEGYGI |
| 15 Tsg6-CUB | CGGVF..TDPKRIFKSPGFPN.EYED.NQICYWHIRLKYGQRI |
| 16 Aqn-3-CUB | CGGFLKNYS....GWIS..Y......YKALTTNCVWTIEMKPGHKI |

Fig. 6B

| | | | | |
|---|---|---|---|---|
| 1 | Cubilin-CUB2 | TFTFGTLSLE | ...SH... | NDCSKDYLEIRDGPFHQD..PVLGKFCTS |
| 2 | Cubilin-CUB5 | RLEFSSFYLE | ..FH... | YNCTNDYLEIYDTA..AQ.TFLGRYCG. |
| 3 | Cubilin-CUB6 | ALHFTDFTLE | .DYFGSQC. | VDFVEIRDGGYETS..PLVGIYCG. |
| 4 | Cubilin-CUB9 | QLTIHDFDVE | ..YHTS... | CNYDSLEIYAGLDFNS..PRIAQLCSQ |
| 5 | Cubilin-CUB12 | QLSFLSFNLE | .NSLN... | CNKDFVEIREGNATGH..LIGRYCG. |
| 6 | Cubilin-CUB17 | TLSFEDFNLQ | .SSPG... | CTKDFVEIWENHTSGR..VLGRYCG. |
| 7 | Cubilin-CUB20 | TLTLSDFLLE | .AHPT... | CTSDSVTVRNGDSPGS..PVIGRYCGQ |
| 8 | Bmp-1-CUB1 | ILNFT..SLD | .LYRSRL | CWYDYVEVRDGFWRKA..PLRGRFCG. |
| 9 | Bmp-1-CUB2 | GLTFQSFEIE | ..RHDS... | CAYDYLEVRDGHSESS..TLIGRYCG. |
| 10 | Tolloid-CUB2 | ALKFQSFELE | ..KHDG... | CAYDFVEIRDGNHSDS..RLIGRFCG. |
| 11 | Tolloid-CUB3 | FLNFSHFDLE | GTRFHYTK | CNYDYLIYSKMRDNRLKKIGIYCG. |
| 12 | Tolloid-CUB4 | QLTFHDFEVE | ..SHQE... | CIYDYVAIYDGRSENS..STLGIYCG. |
| 13 | Uvs-2-CUB2 | SLRITDFELEI | .GASCRYDYLNIYNS...TLGAVMGPYCGP |
| 14 | C1s-CUB1 | HLYFTHLDIEL | .SENCAYDSVQIISGDTEE......GRLCGQ |
| 15 | Tsg6-CUB | HLSFLDFDLE | ..DDPG... | CLADYVEIYDSYDDVH.GFVGRYCG. |
| 16 | Aqn-3-CUB | ILQILPLNL. | ......... | TCGKEYLEVRDQRAGPDNFL..KVCGG |

Fig. 6C

| | | | | | |
|---|---|---|---|---|---|
| 1 | Cubilin-CUB2 | L..STP.P.LKTTGP..... | AARIHFHSDSETSDK.. | GFHITY | SEQ ID NO. 21 |
| 2 | Cubilin-CUB5 | K...SIP.PSLTSNSN.... | SIKLIFVSDSALAHE.. | GFSINY | SEQ ID NO. 22 |
| 3 | Cubilin-CUB6 | ...SVLP.PTIISHSN.... | KLWLKFKSDAALTAK.. | GFSAYW | SEQ ID NO. 23 |
| 4 | Cubilin-CUB9 | SPSANP.MQVSSTGN..... | ELAIRFKTDSTLNGR.. | GFNASW | SEQ ID NO. 24 |
| 5 | Cubilin-CUB12 | ...NSLP.GNYSSAEGH... | SLWVRFVSDGSGTGM.. | GFQARF | SEQ ID NO. 25 |
| 6 | Cubilin-CUB17 | ...NSTP.SSVDTSSNV... | AS..VKFVTDGSVTAS. | GFRLQF | SEQ ID NO. 26 |
| 7 | Cubilin-CUB20 | SV.....P.RPIQSGSN.... | QLIVTFNTNNQGQTR.. | GFYATW | SEQ ID NO. 27 |
| 8 | Bmp-1-CUB1 | ..SKLP.EPIVSTDS..... | RLWVEFRSSNWVGK... | GFFAVY | SEQ ID NO. 28 |
| 9 | Bmp-1-CUB2 | .YEKP.DDIKSTSS..... | RLWLKFVSDGSINKA.. | GFAVNF | SEQ ID NO. 29 |
| 10 | Tolloid-CUB2 | ...DKLP.PNIKTRSN.... | QMYIRFVSDSSVQKL.. | GFSAAL | SEQ ID NO. 30 |
| 11 | Tolloid-CUB3 | ...HELP.PVVNSEQSI... | LRLEFYSDRTVQRS... | GFVAKF | SEQ ID NO. 31 |
| 12 | Tolloid-CUB4 | ..GREP.YAVIASTN.... | EMFMVLATDAGLQRK.. | GFKATF | SEQ ID NO. 32 |
| 13 | Uvs-2-CUB2 | IDFH...SAIVSKSN..... | SMMITMNSDFSKQYK.. | GFSATY | SEQ ID NO. 33 |
| 14 | C1s-CUB1 | RSSNNPHSPIVEEFQVPYNKLQVIFKSDFSNEERFTGFAAYY | | | SEQ ID NO. 34 |
| 15 | Tsg6-CUB | ..DELP.DDIISTGNV... | MTLKFLSDASVTAG.. | GFQIKY | SEQ ID NO. 35 |
| 16 | Aqn-3-CUB | TGF......VYQSHNVAT.. | VKYSRDS...HHPASSFNVYF | | SEQ ID NO. 36 |

Fig. 6D

CUBILIN PROTEIN, DNA SEQUENCES ENCODING CUBILIN AND USES THEREOF

CROSS-REFERENCE TO RELATED APPLICATION

This patent application is the national stage of PCT/US99/01259 Jan. 21, 1999 claims benefit of provisional patent application U.S. Serial No. 60/072,197, filed Jan. 22, 1998, now abandoned.

FEDERAL FUNDING NOTICE

The present invention was funded in part by NIH grant DK46117. Consequently, the United States government has certain rights in this invention.

BACKGROUND OF THE INVENTION

1. Field of the Invention

The present invention relates generally to the fields of molecular biology, biochemistry and medical therapy. More specifically, the present invention relates to major renal receptors for low molecular weight proteins and potential uses of the receptors for therapy to prevent renal toxicity.

2. Description of the Related Art

Countless proteins of small or intermediate molecular weight, filtered freely or partially through the renal glomerulus, are bound by scavenger pathway receptors on the luminal surface of proximal tubular cells for reuptake (Batuman et al., 1990; Birn et al., 1997; Christensen et al., 1995; Saito et al., 1994). These proteins are then transcytosed back into the circulation, or degraded, releasing amino acids for fresh protein synthesis. The scavenger pathway receptors of the proximal tubular are an essential physiological defense against the urinary loss of a diverse array of plasma proteins essential to homeostatic functions from coagulation to lipid metabolism. Unfortunately, exposure of the scavenger receptors to unusually high concentrations of ligands due to overproduction of a ligand such as myeloma light chains introduction of a freely filtered drug such a s gentamicin, or increased glomerular permeability can disrupt the physiological balance, resulting in severe nephrotoxicity.

The relative contribution of proximal and distal elements to the development of protein nephrotoxicity remains controversial and ill-defined. For light chain nephrotoxicity if they fail to be reabsorbed proximally, the ligands are delivered into the distal tubular segments of the nephron, where they precipitate as casts in combination with Tamm-Horsfall protein (Huang et al., 1997; Weiss et al., 1981; Winearls, 1995), the severity of the renal dysfunctional correlates with the degree of (distal) cast formation (Myatt, 1994; Winearls, 1995). However, some light chains are associated with a pure (proximal) Fanconi syndrome. Myoglobin on the other hand is associated with little (distal) cast formation, but marked proximal tubular damage, with clinical acute tubular necrosis (Paller, 1988; Zager, 1991).

Immunoglobulin light chains are filtered at the glomerulus and endocytosed in the proximal tubule (Batuman et al., 1990; Batuman et al., 1997). In overproduction states, such as multiple myeloma, light chains, also known as Bence-Jones proteins, may produce nephrotoxicity. It was shown previously that free κ- and λ-light chain isotypes bind to a single class of renal proximal tubular receptors which facilitate internalization and degradation (Batuman et al., 1997). To date, however, the receptor(s) which mediate endocytosis of light chains in the proximal tubule have not been characterized.

It has long been postulated that glycoproteins expressed at the apical pole of proximal tubule cells of the kidney acted as scavenger pathway receptors. The only known and cloned receptor until now is megalin, a fairly abundant proximal tubule protein, also known as gp330 or the "Heymann antigen". Megalin is a classic single transmembrane domain giant glycoprotein receptor (Saito et al., 1994), which belongs to the LDLR family (Yamamoto, 1984), and is closely related to the $\alpha_2$-macrogilobulin receptor, which is not expressed in the kidney (Moestrup, 1994). Characterization of megalin revealed that, like the $\alpha_2$M receptor, it was a multiligand receptor. Of particular interest for the renal pathology, megalin binds tPA and urokinase in complex with the corresponding inhibitor, but is also a polybasic drug receptor, binding ligands such as the aminoglycoside antibiotics (Moestrup et al., 1995).

Thus the prior art is deficient in the lack of renal receptors for toxic, physiological, and pathological proteins and drugs (such as myeloma light chains) and more generally, components that may gain access to the proximal tubule fluid. Further, the prior art is deficient in the lack of effective means of preventing renal toxicity by utilizing renal binding proteins or fragments thereof for such components. The present invention fulfills these long-standing needs and desires in the art.

SUMMARY OF THE INVENTION

The present invention discloses renal binding proteins for ligands. Also disclosed are the potential uses of these proteins for therapy to prevent renal toxicity or other types of toxicity.

In one embodiment of the present invention, there is provided a DNA encoding a cubilin protein selected from the group consisting of: (a) isolated DNA which encodes a cubilin protein; (b) isolated DNA which hybridizes to isolated DNA of (a) and which encodes a cubilin protein; and (c) isolated DNA differing from the isolated DNAs of (a) and (b) in codon sequence due to the degeneracy of the genetic code, and which encodes a cubilin protein. Preferably, the DNA has the sequence shown in SEQ ID No. 1, and cubilin protein has the amino acid sequence shown in SEQ ID No. 2. Still preferably, the DNA is expressed in the tissues like kidney, spleen, brain, liver, heart and thyroid.

In one embodiment of the present invention, there is a vector capable of expressing the DNA adapted for expression in a recombinant cell and regulatory elements necessary for expression of the DNA in the cell. Specifically, the DNA encodes a cubilin protein.

In another embodiment of the present invention, there is a host cell transfected with the vector expressing a cubilin protein. Specifically, the host cell is selected from the group consisting of bacterial cells, mammalian cells, plant cells and insect cells. More specifically, the bacterial cell is *E. coli*.

In another embodiment of the present invention, there is provided isolated and purified cubilin protein or fragment coded for by DNA selected from the group consisting of: (a) isolated DNA which encodes a cubilin protein or fragment; (b) isolated DNA which hybridizes to isolated DNA of (a) and which encodes a cubilin protein or fragment; and (c) isolated DNA differing from the isolated DNAs of (a) and (b) in codon sequence due to the degeneracy of the genetic code, and which encodes a cubilin protein or fragment. Preferably, the protein has the amino acid sequence shown in SEQ ID No. 2, and the fragment has amino acid sequence consisting of one or more of the sequences selected from the group consisting of SEQ ID Nos. 21–27.

In another embodiment of the present invention, there is provided a method of detecting expression of the cubilin protein or fragment in a sample, comprising the steps of: (a) contacting mRNA obtained from the sample with a labeled hybridization probe; and (b) detecting hybridization of the probe with the mRNA.

In another preferred embodiment of the present invention, there is provided a pharmaceutical composition comprising the cubilin protein or fragment and a pharmaceutically acceptable carrier. Such composition can be used for treating or reducing nephrotoxicity or other types of toxicity in an in-need individual.

In still another embodiment of the present invention, there is provided a receptor for a variety of ligands, comprising a cluster of EGF repeats and a cluster of CUB domains. Specifically, the receptor is cubilin and the ligand is selected from the group consisting of immunoglobulin light chain, myoglobin, intrinsic factor-vitamin $B_{12}$, metallothionein, β-2-microglobulin, amyloid, hemoglobin, haptoglobin, interferon, insulin, cytochrome c, lysozyme, transferrin, transthyretin, polybasic drugs, apolipoprotein AI, high density lipoprotein and receptor related protein. More specifically, a representative example of polybasic drug is gentamicin. Representative examples of immunoglobulin light chain include κ-light chain and λ-light chain.

In still yet another embodiment of the present invention, there is provided a method of detecting renal damage by measuring the level of cubilin in the urine of an individual suspected to have such damage. If the urinary cubilin level is lower than that of a normal individual, the test individual might have chronic renal damage. On the other hand, the test individual might have renal damage of acute origin if the urinary cubilin level is higher than that of a normal individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 3A–3C show amino acid sequence of rat cubilin (SEQ ID NO. 2) as deduced by cDNA cloning. The predicted 20 amino acid endoplasmatic import signal sequence is shown in italic type. Potential glycosylation sites are indicated by asterisks. The sequence verified by protein sequencing of tryptic peptides are shown in boldface type. The estimated mass of the peptide backbone is 396,953 kDa and pI is 5.6.

FIG. 5A shows schematic representation of the 460 kDa receptor (designated cubilin) and related developmental control proteins, human bone morphogenic protein-1 (BMP-1), human tumor necrosis factor stimulating gene 6 (TSG-6), pig spermadhesin aqn3, and the Drosophila protein tolloid. The EGF repeats and CUB domains encode the whole protein except the 110 residues after the signal peptide. FIG. 5B shows a dot plot display of the high internal homology of the CUB domains in cubilin.

FIG. 6A shows alignment of the EGF repeats in cubilin and homologous repeats in CUB domain-containing proteins (Bmp-1, tolloid protein, C1s) and in human fibrillin-1 (SEQ ID Nos. 6–20). The consensus residues for calcium binding are indicated at the bottom of the figure. FIGS. 6B–6D show alignment of cubilin CUB domains and CUB domains in the development control proteins shown in FIG. 5, *Xenopus laevis* Uvs-2 and human C1s (SEQ ID Nos. 21–36).

FIG. 10A shows sensorgram of the binding of cubilin to megalin. The binding curves in the presence of 10 mM EDTA or after prebinding of RAP to megalin are also shown. FIG. 10B demonstrates the formation of an IF-$B_{12}$-cubilin megalin complex by subsequent flow with cubilin, running buffer and IF-$B_{12}$. Evaluation of the binding data suggests a complex binding. By fitting the binding data to a one-binding-site model a $K_d$ of 7 nM was measured.

FIG. 11A shows Western blot analysis with a holo-gp280 polyclonal antiserum (left gel) and SDS-PAGE result (right gel). Cubilin at 460 kDa is accompanied by a prominent band at the region of 56 kDa. FIG. 11B shows coomassie-stained two-dimensional gel with pH gradient from 4–8 on abscissa and molecular weight on the ordinate which demonstrates relative protein abundance.

FIG. 12A shows binding of cubilin to immobilized κ-light chains is dose dependent with rapid low affinity association and dissociation kinetics. FIG. 12B shows competition experiment which further demonstrates the specificity of binding of cubilin to immobilized κ-light chains. A sample of cubilin (100 nM) was incubated with κ-light chains (10 or 490 μM), or κ-light chains (10 or 490 μM) prior to injecting the sample over the κ-light chain surface. The binding of cubilin to the immobilized surfaces was reduced in the presence of κ- or λ-light chains in a dose-response fashion. Data are representative of experiments with 4 light chains on 3 chips. FIG. 12C shows effect of temperature on binding of cubilin (110 nM) to λ-light chains surface. LC, light chains: RU, response units.

FIG. 13A shows that anti-cubilin polyclonal antiserum (•) inhibits $^{125}$I-labeled λ-light chain binding to rat renal brush-border membrane vesicles, but megalin antiserum (o) had no effect. FIG. 13B shows vesicle-by-vesicle analysis of FITC-light chain binding by flow cytometry. Each panel depicts 2,000 vesicles, and each dot represents one vesicle. FITC-fluorescence on the abscissa is displayed against vesicle size on the ordinate. Representative of n=8. Note most but not all vesicles bind FITC-light chains in the left panel, and anti-cubilin antiserum reduces binding (right panel).

FIG. 14A shows FITC-κ-light chain endocytosis by yolk sac epithelial cells (BN/MSV) at 30 min. FIG. 14B shows time course of the endocytosis of FITC-λ-light chain in BN/MSV cells in the presence and absence of anti-cubilin antibody over 40 min. LC, light chain; Ab, antibody.

FIG. 17A shows RT-PCR with 2 sets of primers. Lanes 1, 3, 5, 7 and 9 used a primer (tgcctaccacagcccaaatga, SEQ ID No. 37) located in one of the 3' CUB domains; and lanes 2, 4, 6, 8 and 10 used another primer (agagccacaatgactgcag, SEQ ID No. 38) located in the end of the EGF regions. Lanes 1–2: RNA from spleen; lanes 3–4: RNA from brain; lanes 5–6: RNA from liver; lanes 7–8: RNA from heart; lanes 9–10: RNA from Brown Norway (BN) rat immortalized yolk sac epithelial cells; lane 11: RNA from immortalized opossum kidney (OK) cells with megalin primers (SEQ ID Nos. 39–40). FIG. 17B shows RT-PCR with cubilin primers (SEQ ID Nos. 37–38). Lane 1: kidney; lane 2: thyroid.

DETAILED DESCRIPTION OF THE INVENTION

Figure 1:
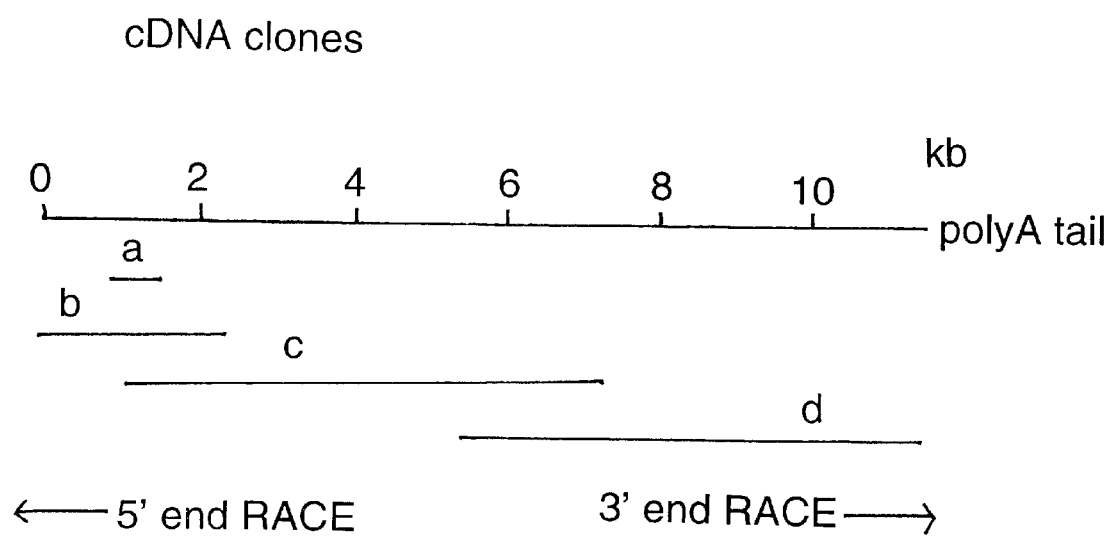
FIG. 1 shows cDNA cloning of the rat yolk sac cubilin. The 11.6 kb cDNA sequence was encoded by three clones (b–d) from a rat yolk sac cell cDNA library. The ends of the cDNA were confirmed by sequencing 3'- and 5'-RACE products from a rat kidney cDNA library with end-ligated adaptors. A polyadenylation signal followed by a poly(A) tail is present 0.4 kb downstream the open reading frame (0.4–11.2 kb). The position of the initially identified clone is indicated (a).

The present invention discloses the molecular characterization of the 460 kDa epithelial glycoprotein that functions as the receptor facilitating uptake of intrinsic factor-vitamin $B_{12}$ complexes in the intestine and kidney. The 3603 amino acid rat sequence has one cluster of 8 EGF-type domains followed by a cluster of 27 CUB domains accounting for 88% of the protein mass. The receptor, cubilin, has no similarity to known endocytic receptors. Instead, it displays homology to EGF and CUB domain-containing proteins involved in fetal development. Cubilin is a peripheral membrane protein which can be released from renal cortex membranes by non-enzymatic and non-solubilizing procedures. Electron microscopic immuno-gold labeling of rat yolk sac and renal proximal tubules revealed that the endocytic receptor megalin and cubilin strictly colocalize in the endocytic apparatus. Megalin-affinity chromatography and surface plasmon analysis demonstrated a calcium-dependent high affinity binding of cubilin to the extracellular part of megalin which thereby may assist the intracellular trafficking of this novel type of receptor.

Myeloma light chains are known to undergo receptor-mediated endocytosis in the kidney, however, the molecular identity of the receptor has not been characterized. The present studies provide several lines of evidence to identify cubilin (gp280), a giant glycoprotein receptor, which is preferentially expressed in endocytic scavenger pathways and which has potent effects on endosomal trafficking, as an endocytic receptor for immunoglobulin light chains. Binding showed dose and time-dependent saturability with low-affinity, high-capacity equilibrium binding parameters. The data demonstrate that cubilin plays a role in the endocytosis and trafficking of light chains in renal proximal tubule cells.

Agents that inhibit binding of light chains are ligands of cubilin. More generally, the proteins present in the urine of patients or dogs deficient in cubilin contain a variety of proteins including albumin which constitute ligands.

Independent evidence also suggests that light chains are ligands for megalin. These studies are important, both to understand the complex interactions of toxic and physiological ligands on proximal tubule scavenger pathway receptors, as well as the eventual development of clinical protective agents for nephrotoxic damage mediated by ligands for cubilin and/or megalin.

If appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as improvements now known in the art.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $90Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes cubilin protein of the present invention can be used to transform a host using any of the techniques commonly known to those of ordinary skill in the art. Especially preferred is the use of a vector containing coding sequences for the gene which encodes cubilin protein of the present invention for purposes of prokaryote transformation.

Prokaryotic hosts may include *E. coli, S. typhimurium, Serratia marcescens* and *Bacillus subtilis.* Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a cubilin protein, a strand of which DNA will hybridize at high stringency to a probe containing a sequence of at least 15 consecutive nucleotides of SEQ ID NO:1. The protein encoded by the DNA of this invention may share at least 80% sequence identity (preferably 85%, more preferably 90%, and most preferably 95%) with the amino acids listed in SEQ ID NO. 2. More preferably, the DNA includes the coding sequence of the nucleotides of SEQ ID NO:1, or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID NO. 1 or the complement thereof. Such a probe is useful for detecting expression of cubilin in a human cell by a method such as a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the nucleotides listed in SEQ ID NO. 1.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO. 1 encoding an alternative splice variant of cubilin.

The DNA may have at least about 70% sequence identity to the coding sequence of the nucleotides listed in SEQ ID NO:1, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence of 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence coding for a human cubilin protein and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No. 1. A "vector" may be defined as a replicable nucleic acid construct, e.g., a plasmid or viral nucleic acid. Vectors may be used to amplify and/or express nucleic acid encoding cubilin protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure cubilin protein may be obtained, for example, by extraction from a natural source; by expression of a recombinant nucleic acid encoding an cubilin polypeptide; or by chemically synthesizing the protein. Purity can be measured by any appropriate method, e.g., column chromatography such as immunoaffinity chromatography using an antibody specific for cubilin, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the cubilin protein (SEQ ID No. 2). As used herein, "fragment," as applied to a polypeptide, will ordinarily be at least 10 residues, more typically at least 20 residues, and preferably at least 30 (e.g., 50) residues in length, but less than the entire, intact sequence. Fragments of the cubilin protein can be generated by methods known to those skilled in the art, e.g., by enzymatic digestion of naturally occurring or recombinant cubilin protein, by recombinant DNA techniques using an expression vector that encodes a defined fragment of cubilin, or by chemical synthesis. The ability of a candidate fragment to exhibit a characteristic of cubilin (e.g., binding to an antibody specific for cubilin, or binding to a known ligand of cubilin) can be assessed by methods described herein. Purified cubilin or antigenic fragments of cubilin can be used to generate new antibodies or to test existing antibodies (e.g., as positive controls in a diagnostic assay) by employing standard protocols known to those skilled in the art. Included in this invention are polyclonal antisera generated by using cubilin or a fragment of cubilin as the immunogen in, e.g., rabbits. Standard protocols for monoclonal and polyclonal antibody production known to those skilled in this art are employed. The monoclonal antibodies generated by this procedure can be screened for the ability to identify recombinant cubilin cDNA clones, and to distinguish them from known cDNA clones.

Further included in this invention are cubilin proteins or fragments which are encoded at least in part by portions of SEQ ID NO. 2, e.g., products of alternative mRNA splicing or alternative protein processing events, or in which a section of cubilin sequence has been deleted. The fragment, or the intact cubilin polypeptide, may be covalently linked to another polypeptide, e.g. which acts as a label, a ligand or a means to increase antigenicity. The lack of cross inhibition of a number of ligands suggests that specific therapeutic components can be produced.

Also within the invention is a method of detecting cubilin protein or fragment in a biological sample, which includes the steps of contacting the sample with the labelled antibody, e.g., radioactively tagged antibody specific for cubilin, and determining whether the antibody binds to a component of the sample.

A standard Northern blot assay can be used to ascertain the relative amounts of cubilin mRNA in a cell or tissue obtained from a patient, in accordance with conventional Northern hybridization techniques known to those persons of ordinary skill in the art. This Northern assay uses a hybridization probe, e.g. radiolabelled cubilin cDNA, either containing the full-length, single stranded DNA having a sequence complementary to SEQ ID NO. 1, or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art. RNA probes can also be similarly utilized.

The present invention is also directed to a vector capable of expressing the DNA of the present invention adapted for expression in a recombinant cell and regulatory elements necessary for expression of the DNA in the cell. Preferably, the vector contains DNA encoding a cubilin protein having the amino acid sequence shown in SEQ ID No. 2.

The present invention is also directed to a host cell transfected with the vector described herein, said vector expressing a cubilin protein. Representative host cells include consisting of bacterial cells, mammalian cells and insect cells.

The present invention is also directed to a isolated and purified cubilin protein or fragment coded for by DNA selected from the group consisting of: (a) isolated DNA which encodes a cubilin protein or fragment; (b) isolated DNA which hybridizes to isolated DNA of (a) and which encodes a cubilin protein or fragment; and (c) isolated DNA differing from the isolated DNAs of (a) and (b) in codon sequence due to the degeneracy of the genetic code, and which encodes a cubilin protein or fragment. Preferably, the isolated and purified cubilin protein has the amino acid sequence shown in SEQ ID No. 2, and the fragment has amino acid sequence consisting of one or more of the sequences selected from the group consisting of SEQ ID Nos. 21–27.

The present invention is also directed to a method of detecting expression of the cubilin protein or fragment, comprising the steps of: (a) contacting mRNA obtained from a sample with a labeled hybridization probe; and (b) detecting hybridization of the probe with the mRNA.

The present invention is further directed to a pharmaceutical composition comprising the cubilin protein or fragment and a pharmaceutically acceptable carrier. Such composition can be used for treating or reducing nephrotoxicity or other types of toxicity in an in-need individual.

In an additional embodiment, the present invention is directed to a receptor for a variety of ligands, comprising a cluster of EGF repeats and a cluster of CUB domains. Specifically, the receptor is cubilin and ligand selected from the group consisting of immunoglobulin light chain, myoglobin, intrinsic factor-vitamin $B_{12}$, metallothionein, β-2-microglobulin, amyloid, hemoglobin, haptoglobin, interferon, insulin, cytochrome c, lysozyme, transferrin, transthyretin, polybasic drugs, low density lipoprotein, high density lipoprotein and receptor related protein. A representative example of a polybasic drug is gentamicin. Representative examples of immunoglobulin light chain include κ-light chain and λ-light chain.

In still yet another embodiment of the present invention, there is provided a method of detecting renal damage by measuring the level of cubilin in the urine of an individual suspected to have such damage. If the urinary cubilin level is lower than that of a normal individual, the test individual might have chronic renal damage, on the other hand, the test individual might have renal damage of acute origin if the urinary cubilin level is higher than that of a normal individual.

The following examples are given for the purpose of illustrating various embodiments of the invention and are not meant to limit the present invention in any fashion.

EXAMPLE 1

Animals, Reagents and Antibodies

Male Sprague Dawley rats (200–250 gm) were from Sasco, Omaha, NE, and all other reagents were from Sigma Chemical company (St. Louis Mo.) unless otherwise stated. Polyclonal antibodies were raised against proteins purified by immuno-affinity chromatography using reported monoclonal antibodies coupled to Sepharose 4B (Baricault et al., 1995; Sahali et al., 1988; Sahali et al., 1993). These antibodies are monospecific by immunoblotting on whole brush border preparations and by immuno precipitation of biosynthetically labeled yolk sac epithelial cells in culture (Sahali et al., 1993), and bind the cytosolic domains of the protein (Hammond et al., 1993). Control antisera included normal rabbit antiserum, and polyclonal rabbit antiserum to the neurokinin-1/substance P, NK1, receptor (from Professor Jean-Yves Courard, Gif.-Sur-Yvette, France).

EXAMPLE 2

Sequencing and Estimation of N-Linked Carbohydrate of Cubilin

CNBr fragments and tryptic digests of a 100 kDa CNBr fragment of purified rat cubilin were purified by reverse phase HPLC and seven isolated peptides subjected to Edmann degradation using an Applied Biosystems 477 A sequencer equipped with a 120 A on-line chromatograph. A cross-flow reaction and the Doublot reaction and conversion cycles were used. Deglycosylation with peptide N-glycosidase F (PGNase F) of 5 μg of purified rabbit intrinsic factor was carried out as described (Jensen et al. 1992).

EXAMPLE 3 cDNA Cloning, Sequencing and Northern Blotting

Total RNA was extracted from renal cortex and BN cells using Trizol (Gibco, Life Sciences) as described by the manufacturer. mRNA required for library construction was isolated using the Qiagen Oligotex kit. Northern blots were made with 1 μg of mRNA and revealed with $^{32}$P labeled riboprobes (bp 1205 to 1645 and bp 1702 to 2175).

Four libraries were used. Two conventional libraries were constructed in the laboratory using cDNAs synthesized by oligo dT and random priming of polyA-selected RNA from yolk sac derived BN/MSV epithelial cells using the superscript Kit (Gibco Life Sciences). After ligation to EcoR1 adaptors and size fractionation, they were introduced in λZap or λgt11 EcoR1 site. Subsequently screening was performed on a commercial λZap cDNA library (Stratagene) prepared from yolk sac derived L2 epithelial cells. Finally to identify the 5' end, a library was constructed in λgt11 using the 5' Cap Finder library from Clontech. Immunoscreening was carried out on the λZap-BN library using previously reported polyclonal antibodies to gp280. cDNA probes were constructed from known sequences by PCR using a 1/19 mixture of digoxygenin labeled nucleotide (Boehringer) and used to identify overlapping clones.

RACE was carried out using Marathon ready cDNA prepared from rat renal cortex (Clontech). Specific primers were from bp 838–859 (SEQ ID NO. 3) for 5' RACE and bp 6872–6891 (SEQ ID NO. 4) and bp 7152–7172 (SEQ ID NO. 5) for 3' RACE. Inserts were prepared by the ex vivo excision system for λzap clones (Stratagene). cDNAs from λgt11 clones were isolated by EcoR1 digestion and inserted in Bluescript. Sequencing was carried out by cycle sequencing in both directions with IRD-41 labeled primers and the sequence reaction were analyzed on a LICOR 4000 automatic sequencer.

EXAMPLE 4

Release of Cubilin from Renal Cortex Membranes

Rat renal cortex (0.6 g) was suspended in 3 ml PBS, pH 7.4, containing 0.1 mM phenylmethylsulfonylfluoride and Pefablock (Boehringer) and homogenized on ice using an ultrathorax homogenizer (23,000 rpm/min) for 20 sec. The homogenate was centrifuged at 20,800×g for 20 min. The saline soluble and saline insoluble samples were analyzed by immunoblotting with anti-cubilin and anti-megalin monoclonal antibodies (Birn et al. 1997). The amounts loaded on the gels were adjusted so that both fractions were derived from 20 μg of original cortex. IF-$B_{12}$ affinity chromatography of the fluid phase was performed as described (Birn et al. 1997) except that the buffer contained no detergent.

Rabbit renal membranes were prepared as described (Moestrup et al. 1993). For release of cubilin, 2 mg of membranes were incubated in 525 μl of PBS, 250 units/ml heparin (LEO, Denmark), 20 mM EDTA or 5 mM phosphatidylethanolamine (Sigma) for 1 h at 22° C. followed by centrifugation at 20,800×g for 20 min.

EXAMPLE 5

Immunocytochemistry

Rat kidneys were fixed by retrograde perfusion through the abdominal aorta with 8% paraformaldehyde in 0.1 M sodium carcodylate buffer, pH 7.2. The tissue was trimmed into small blocks, further fixed by immersion for 1 hour in the same fixative, infiltrated with 2.3 M sucrose containing 2% paraformaldehyde for 30 minutes and frozen in liquid nitrogen. Rat embryos at day 12 of gestation were dissected free of the decidua and parietal layer to expose yolk sac epithelial cells. The tissue was then fixed by immersion and further processed as described above. For electron microscopy, 70 to 90 nm cryosections were obtained at −100° C. with an FCS Reichert Ultracut S cryoultramicrotome as described (Christensen et al. 1995). For double immunolabeling, the sections were incubated with the two primary antibodies overnight at 4° C. after preincubation in PBS containing 0.05 M glycine and 1% bovine serum albumin. Sheep anti-rat megalin serum (Moestrup et al. 1993) was diluted 1:200,000 and mouse monoclonal MAB75 (2 μg/ml) against cubilin (Sahali et al 1988). The sections were then incubated for 30 minutes with rabbit anti-sheep serum 1:20,000 (Dako A/S, Glostrup, Denmark), and finally incubated with 10 nm goat anti-rabbit gold particles and 5 nm goat anti-mouse gold particles (BioCell, Cardiff, UK). The sections were embedded in methylcellulose and studied in a Philips CM100 electron microscope. As controls, sections were incubated with secondary antibodies alone or with non-specific monoclonal antibodies or sheep antiserum.

EXAMPLE 6

Binding of $^{125}$I-Cubilin to Megalin

Megalin was immobilized to CNBr-Sepharose 4B (Pharmacia, Uppsala, Sweden) at a density of 0.5 mg megalin/ml gel. Cubilin was iodinated ($10^6$ Bq/μg) by the iodogen method (Pierce). The $^{125}$I-labeled cubilin was purified by S-300 (Pharmacia) gel filtration and $10^6$ cpm was loaded on the megalin-column. After wash with binding buffer (20 mM Hepes, 150 mM NaCl, 2 mM $CaCl_2$, pH 7.8), bound radioactivity was eluted with the same buffer supplemented with 10 mM EDTA, counted and analyzed by SDS-PAGE.

EXAMPLE 7

Megalin-Cubilin Interaction Analysis by Surface Plasmon Resonance

Surface plasmon resonance measurements were performed on a BIAcore 2000 instrument (Pharmacia, Sweden). BIAcore sensor chips (type CM5, Pharmacia) were activated with 1:1 mixture of 0.2 M N-ethyl-N'-(3-dimethylaminopropyl) carbodiimide and 0.05 M N-hydroxysuccimine in water. Rabbit megalin was immobilized as described (Moestrup et al., 1996) at a concentration of 40 μg/ml in 10 mM sodium acetate, pH 4.5 and the remaining binding sites were blocked with 1 M ethanolamine, pH 8.5. The flow buffer was 10 mM Hepes, 150 mM NaCl and 1.5 M $CaCl_2$, 1 mM EDTA, pH 7.4. The binding data were analyzed using the BIAevaluation program.

EXAMPLE 8

Preparation of Light Chains

Four species of light chains, two κ and two λ, were isolated and purified from the urine of four different patients with myeloma, as described (Batuman et al., 1990; Batuman et al., 1997). The purity and the immunologic identity of light chains were confirmed by SDS-PAGE and Western blotting. One of the λ-light chains and the κ-light chain used here were the same light chains used to demonstrate receptor-mediated endocytosis by radioisotope techniques. Competition experiments were initially conducted using radioiodinated λ-light chain, iodinated by the Iodobead method as reported (Batuman et al., 1990; Batuman et al., 1997). It was later switched to competition experiments with fluorescein isothiocyanate (FITC) conjugated κ-light chain. FITC conjugation was performed using FluoroTag FITC Conjugation Kit (Sigma ImmunoChemicals, St. Louis, Mo.).

EXAMPLE 9

Preparation of Renal Brush-Border Membrane Vesicles and Cortical Intermicrovillar Clefts Rat renal cortical brush border membrane vesicles, inside/in, were isolated by magnesium precipitation technique as described (Batuman et al., 1990; Hammond et al., 1985). Rat renal cortical intermicrovillar clefts were prepared from kidneys harvested from anesthetized rats, utilizing differential Percoll gradient centrifugation and magnesium precipitation. It was also shown that the intermicrovillar clefts form vesicles "oriented inside out" in vitro during homogenization and can capture internally components added to the homogenization buffer.

EXAMPLE 10

Preparation of Cubilin

Intermicrovillar clefts prepared from renal cortices were biotinylated on the cytosolic facade using NHS-biotin (Winearls, 1995). Cubilin and the associated proteins were purified by immunoaffinity chromatography MAb 75 was coupled to CNBr-activated Sepharose 4B (Pharmacia, Saint Quentin en Yvelines, France) as previously described (Sahali et al., 1988; 1993). Protease inhibitors were added at all steps.

EXAMPLE 11

Competition Between Light Chains and Anti-Cubilin and Megalin Anti-Sera for Rat Renal Brush Border Membrane Binding Binding of either [$^{125}$I]-labeled or FITC conjugated light chain was investigated in the presence of up to 100,000 fold serial dilutions of anti-cubilin antibodies (Baricault et al., 1995). Equal dilutions of bovine serum albumin served as controls. With the radio-labeled light chain, binding was assayed in a gamma counter as described (Batuman et al., 1990; 1997). Binding of FITC-conjugated light chain was assayed by flow cytometry using small particle techniques on a Becton-Dickinson FACStar flow cytometry with a Consort 30 computer and WinMidi software (Hammond et al., 1994; Sahali et al., 1988; 1993). The analog-to-digital conversion of fluorescence measurements on each particle passes through a logarithmic amplifier such that florescence is expressed on a log scale.

EXAMPLE 12

Surface Plasmon Resonance Analysis of Light Chain/Cubilin Interaction

κ- or λ-light chains were immobilized via free amine groups to the dextran matrix of CM5 sensor chips activated by a 1/1 mixture of NHS and EDC. Unreacted sites were blocked with 1M ethanolamine, pH 8.5, (Jonsson et al., 1991; Sanders et al., 1988). The immobilization was conducted at 25° C. using 10 mM HEPES, 2 mM CaCl$_2$, 150 mM NaCl, 0.005% NP-40, pH 7.4 as the flow buffer. Then 10 mM acetate pH 4.8 was used for electrostatic preconcentration of the protein. Different densities of κ- or λ-light chains were immobilized to three of the four flow cells; the remaining flow cell was activated and blocked with no light chains immobilized for use as a control surface. Binding experiments were carried out using a BIACORE 2000 instrument.

EXAMPLE 13

Identification by Two-dimensional Gel Electrophoresis and Microsequencing of Proteins Associated with Immunopurified Cubilin The approach used involved three steps: 1) biotinylation of intermicrovillar membranes, 2) immunoisolation of cubilin, and 3) identification of bound proteins by microsequencing. Two-dimensional electrophoresis w as performed according to the method of O'Farrell (O'Farrell, 1975) by Kendrick Labs, Inc. (Madison, Wis.). Proteins other than cubilin observed on two-dimensional gels prepared from the eluate of detergent solubilization of intermicrovillar clefts were identified by microsequencing. For this purpose, three gels were run in parallel, and stained with Coomassie D. The two most abundant spots at MW 56 and 24 kDa from each gel were cut out and the material pooled. The peptides derived from the eluted proteins by C-leu digestion were separated by HPLC, and internal peptides sequenced (Ferrara et al., 1993).

EXAMPLE 14

Effect of Light Chains on Endosomal Fusion

To determine if light chains had a direct effect on membrane fusion, rat renal cortical intermicrovillar clefts were prepared as described (Hammond et al., 1997; 1994) and loaded with 400 mM light chains by addition of the light chains to the homogenization buffer. Fusion of these light chain loaded membranes was compared to control membranes loaded with the same concentration of albumin. All fluorescence measurements were corrected per mg of protein, and fusion reconstituted in vitro in cuvettes (Hammond et al., 1994). Data are expressed as mean +standard error of the mean throughout the application. Statistical analysis was performed by analysis of variance and Bonferroni or Scheffe's post hoc comparison.

EXAMPLE 15

Culture of Rat Visceral Yolk Sac Cells and Internalization Experiments

The yolk sac epithelial cell line (BN/MSV) was derived from yolk sac teratocarcinoma induced by fetectomy and placental injection of mouse sarcoma virus (Sahali et al., 1988). When grown under conventional conditions in modified Eagle's medium, supplemented with 2.5 mM L-glutamine, 10% fetal calf serum, and an antibiotic cocktail (penicillin, streptomycin, and Fungizone), the cells form a domed monolayer and express abundant cubilin (Sahali et al., 1988).

EXAMPLE 16

Effect of Anti-Cubilin Antiserum on Endocytosis of Light Chains

Internalization experiments were conducted by exposing confluent yolk sac cells in 24-cell plates to 50 µm FITC-conjugated light chain. These cells were selected for endocytosis experiments because cubilin expression is 100-fold greater than cultured proximal tubule cells (Sahali et al., 1988). Cells were allowed to endocytose FITC-light chain at various intervals for up to 40 minutes at 37° C. with and without polyclonal anticubilin antibody at 1:1,000 dilution (added at time 0). This concentration is selected because it is 10-fold higher than the half-maximal inhibitory concentration of the antibody determined from the brush border binding inhibition experiments. Endocytosis is stopped by washing twice with PBS and removing light chain from medium. Cells are then trypsininzed, fixed in 1% formaldehyde, and suspended in PBS, and FITC incorporated into each cell is read in a Becton-Dickinson flow cytometer as described previously. Endocytosis curves are generated by plotting fluorescence units corrected for background against time. Excess unlabeled light chain was used to test for specificity, and bovine serum albumin was used as nonspecific protein control.

EXAMPLE 17 cDNA Cloning of Cubilin

Figure 2:
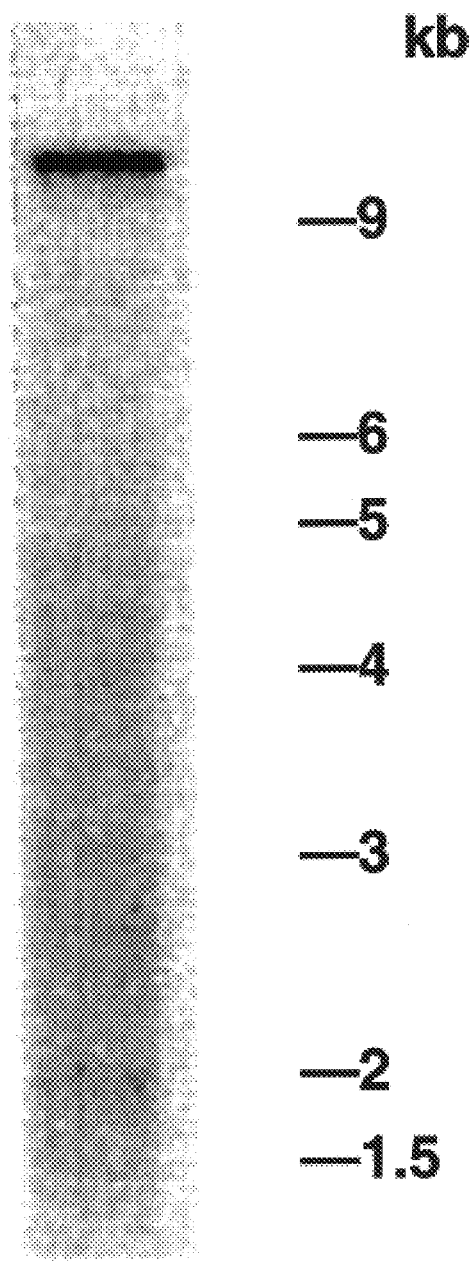
FIG. 2 shows a Northern blot of yolk sac RNA using a cubilin RNA probe.

By immunoscreening of the λ-Zap cDNA library from rat yolk sac BN cells (Le Panse et al. 1995), an initial 0.7 kb clone encoding a portion of cubilin was identified. The 5' sequence of this clone was used to design two nested primers to perform 5' RACE on kidney cDNA allowing identification of the 5' end of cubilin. Using PCR-generated probes for further screening of yolk sac libraries a number of clones were identified. FIG. 1 schematizes three overlapping clones completely sequenced and used to construct the final cDNA. The last clone contained a polyadenylation signal and a poly A tail. The 3' and 5' ends of the 11.8 kb sequence were further confirmed respectively by sequencing a 3' end RACE product and a λgtll clone selected from a Cap Finder library. Northern blot analysis of yolk sac mRNA (FIG. 2) identified a mRNA of the size as the cDNA.

EXAMPLE 18

Primary Structure of Cubilin

Figure 4:
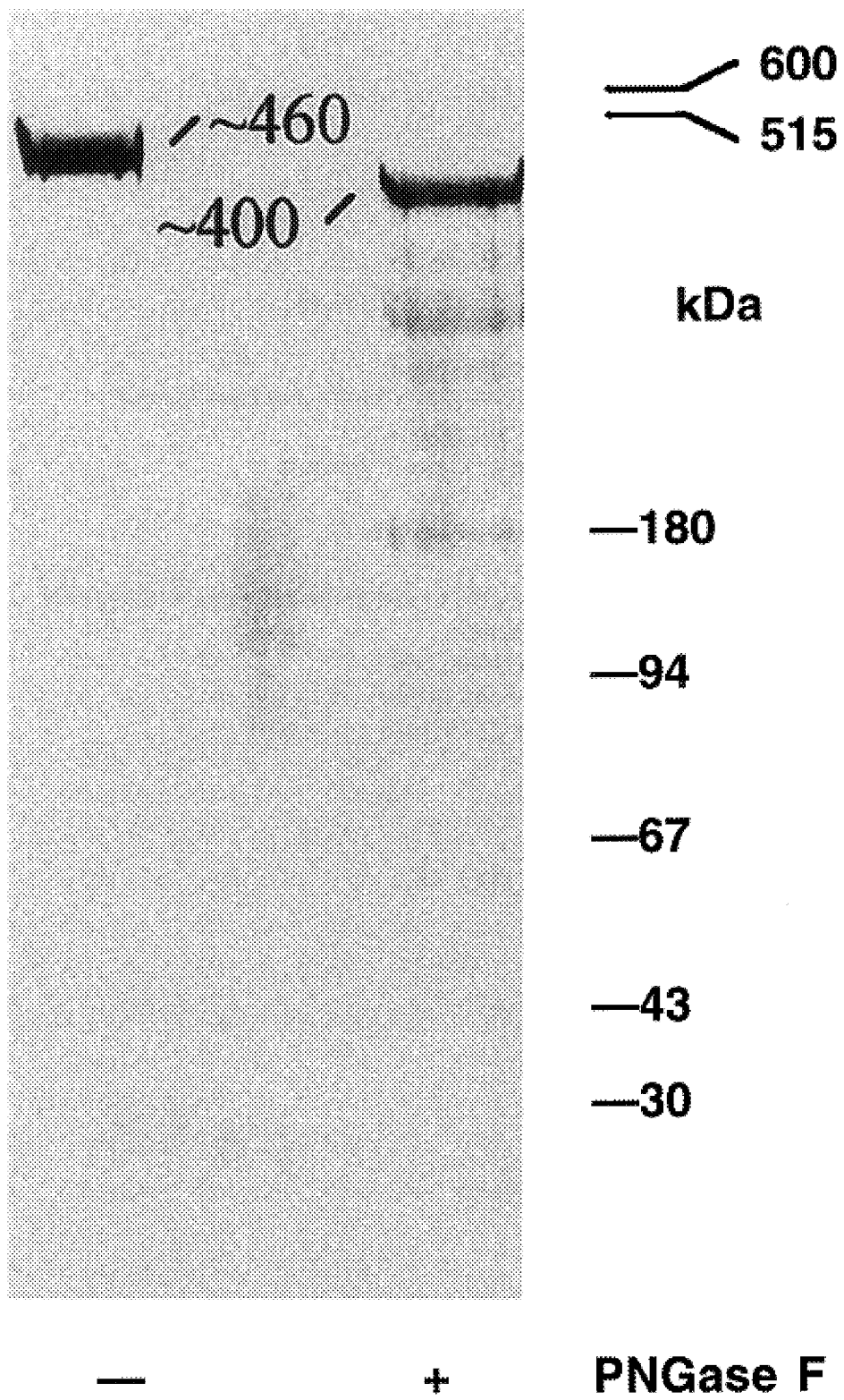
FIG. 4 shows deglycosylation of cubilin purified by IF-$B_{12}$ affinity chromatography of rabbit renal cortex membranes. Reducing SDS-PAGE shows a reduction from 460 kDa (left lane) to approximately 400 kDa (right lane) after treatment with peptide N-glycosidase F (PNGase F).
Figure 5A:
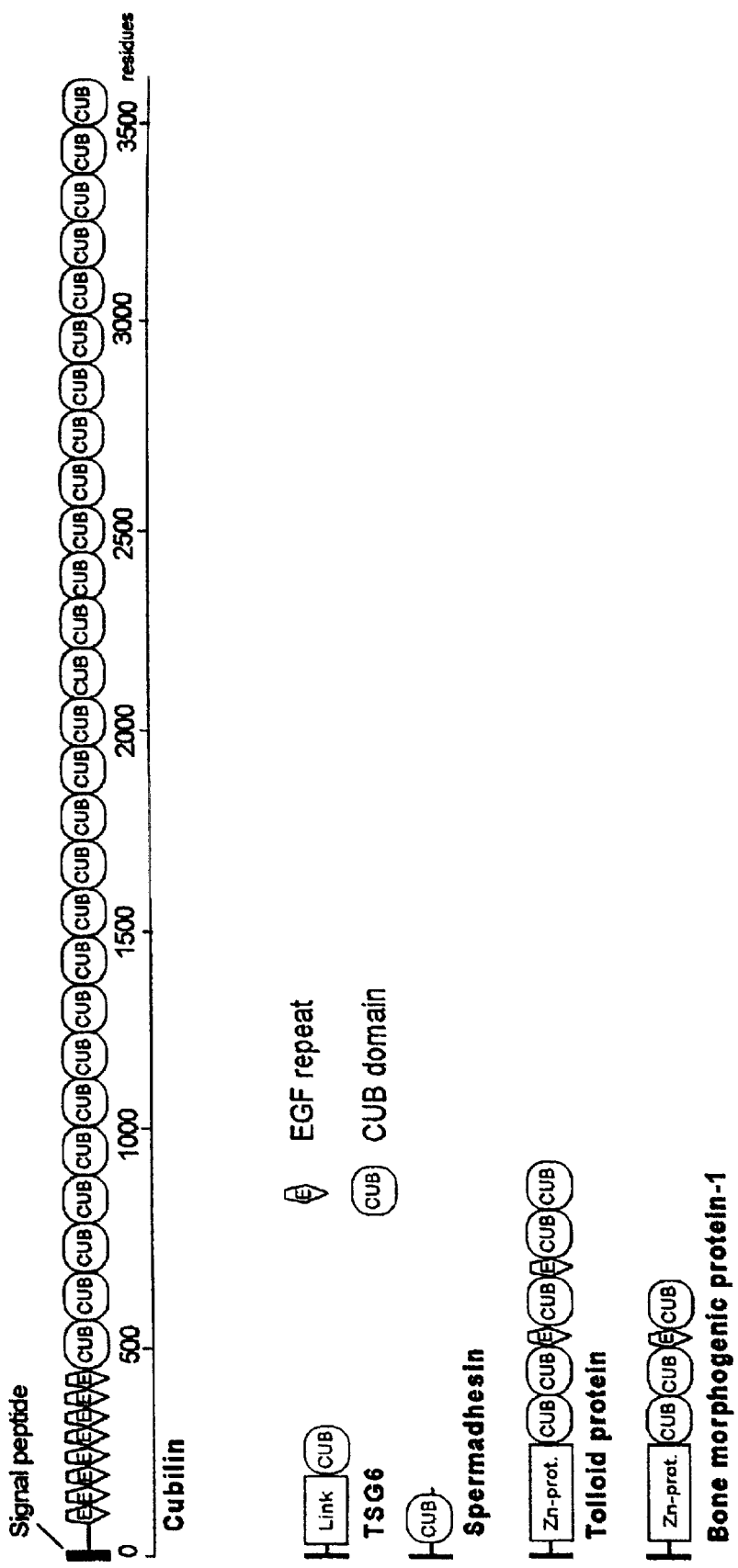
FIGS. 5A–B shows the extracellular modules of cubilin.
Figure 5B:
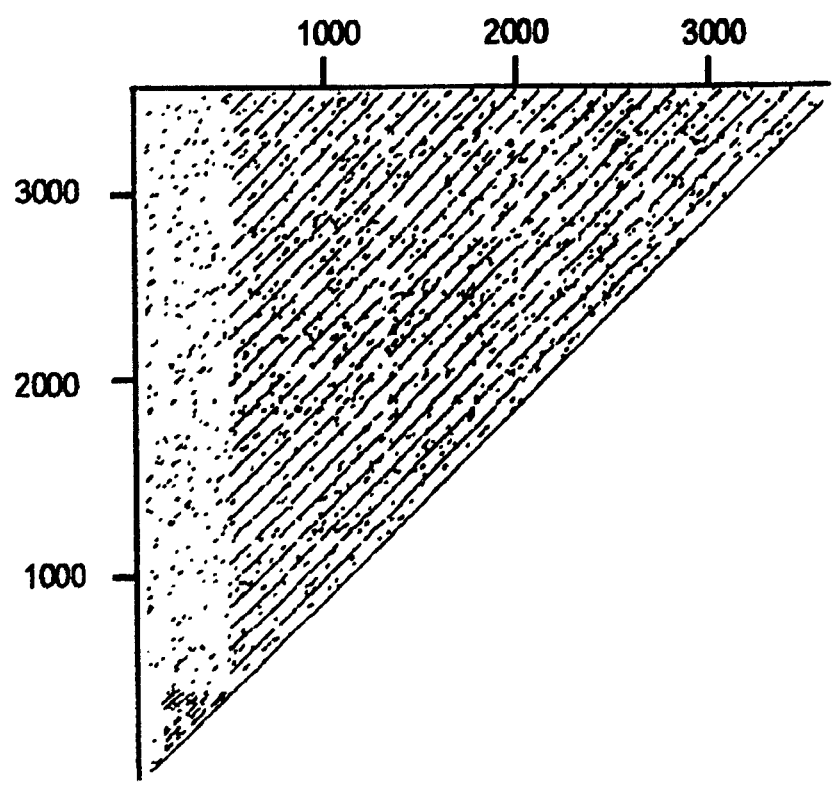

The assembled cDNA (SEQ ID no. 1) revealed an uninterrupted open reading. frame of 10.8 kb encoding a 20 amino acid signal peptide (in italic type) and a 3603 amino acid protein (SEQ ID NO. 2) with 42 potential N-glycosylation sites (FIGS. 3A–3C). The molecular size of the protein backbone was calculated to 397 kDa. The seven amino acid sequences determined by N-terminal microsequencing of tryptic and CNBr peptides were all identified in the translated sequence (bolded letters in FIGS. 3A–3C). The size of the protein was confirmed by SDS-PAGE (FIG. 4). Deglycosylation of the receptor by PNGase F increased its electrophoretic mobility corresponding to a size of 400 kDa. Compared to the 460 kDa size of the untreated protein this indicates a carbohydrate content of ~13% of the receptor mass. FIG. 5A shows the predicted domain organization of the receptor. A stretch of approximately 110 amino acids with no apparent homology to known proteins is followed by a cluster of 8 EGF type B repeats which precedes 27 contiguous CUB domains accounting for 88% of the protein mass. The high degree of internal homology (overall similarity of 45%) between the CUB domains is evident from the dot plot display shown in FIG. 5B. A total of 76 disulfide bridges is predicted if all the extracellular modules fold normally. The only cysteine outside the CUB domains and EGF repeats, is located in the 110 amino acid N-terminal sequence. This cysteine might account for the partial, disulfide bond dependent dimerization of a minor part of purified receptor (Le Panse et al., 1995; Birn et al. 1997).

FIGS. 6A–6D show alignment of the EGF repeats and CUB domains of some of the most homologous regions of other proteins. Two of the EGF repeats (Nos. 2 and 4) contain the consensus sequence for $Ca^{2+}$ binding and β-hydroxylation of Asp/Asn (Selander-Sunnerhagen et al. 1992). The 110 amino acids CUB domains contain 4 cysteines except for CUB domain 13 which is missing the first two cysteines suggested to form the upstream disulfide bond (Bork and Beckmann 1993). The high homology of the CUB domains of bone morphogenic factor, the Drosophila dorsalventral patterning gene product tolloid, the embryonic protein Uvs2 in *Xenopus Laevis,* tumor necrosis factor stimulating gene 6 (Tsg6), C1r/C1s and spermadhesin is seen in the two lower panels (FIGS. 6A–6D).

Save for the leader peptide, no sequence compatible with a transmembrane domain could be identified. This excludes the protein as a type 1 membrane protein or a glycosylphosphatidylinositol-anchored protein, which is synthesized with a cleavable hydrophobic C-terminal. Furthermore, since almost the entire protein sequence consists of extracellular modules it is very unlikely that the protein is a type II or III protein with a non-cleaved hydrophobic signal peptide inserted in the membrane (Levy 1996).

EXAMPLE 19

Cubilin is a Peripheral Membrane Protein

Figure 7:
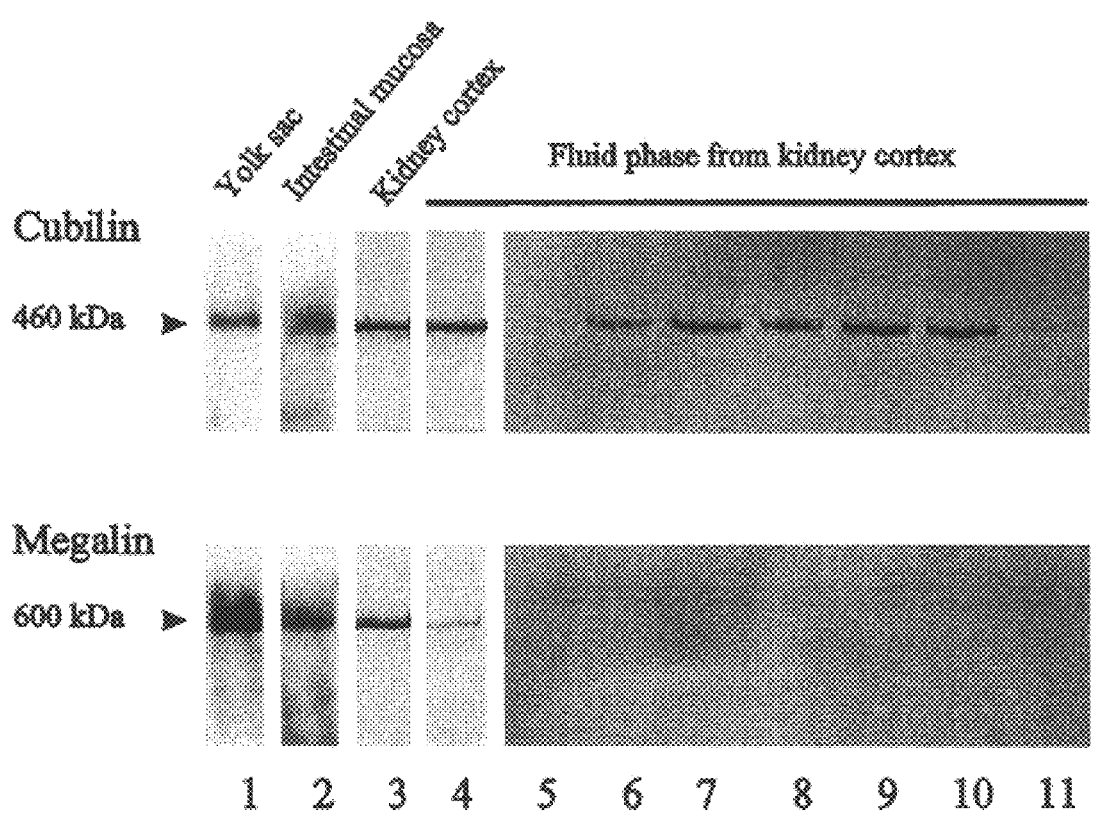
FIG. 7 shows release of membrane-associated cubilin by non-enzymatic and non-solubilizing procedures. Western blot analysis with anti-cubilin antibody (top panel) and anti-megalin antibody (bottom panel). Lane 1: yolk sac BN cells; lane 2: ileal mucosa; lane 3: membrane phase after mechanical grinding of renal cortex; lane 4: fluid phase after mechanical grinding of renal cortex membranes, lanes 5–11: fluid phase of renal cortex membranes after a 1-h incubation in PBS (lane 5), PBS, phosphorylethanolamine, and heparin (lane 6), PBS, phosphorylethalolamine, heparine, and EDTA (lane 7), PBS and heparin (lane 8), PBS and EDTA (lane 9), PBS, heparin, and EDTA (lane 10), PBS and phosphorylethanolamine (lane 11).

In order to verify that cubilin is a peripheral membrane protein, as predicted by the lack of a transmembrane segment and cytoplasmic tail, its release from renal cortex membranes by procedures which do not involve solubilization of the membranes or enzymatic treatment was investigated. FIG. 7 shows the identical size of the renal receptor and the receptor in yolk sac and intestinal mucosa (lanes 1–3). As seen in lane 4 vs. lane 3, approximately 50% of cubilin was released into the fluid phase by mechanical grinding of renal cortex in PBS, whereas megalin, the 600 kDa transmembrane protein expressed in the same tissues (Saito et al. 1994), was released in minimal amounts. Cubilin, which remained membrane-associated, was tightly bound but could be released partly by EDTA, heparin and, to a low extent phosphorylethanolamine (FIG. 7, lanes 5–11). Heparin and phosphorylethanolamine have been reported to bind to the spermadhesin CUB domains (Calvete et al. 1996; Dostolova et al., 1995). The same treatments released virtually no megalin (FIG. 7). The size of the released cubilin, as estimated by SDS-PAGE, was not different from the membrane associated cubilin.

EXAMPLE 20

Cubilin Traffics with and Binds Megalin

Figure 8A:
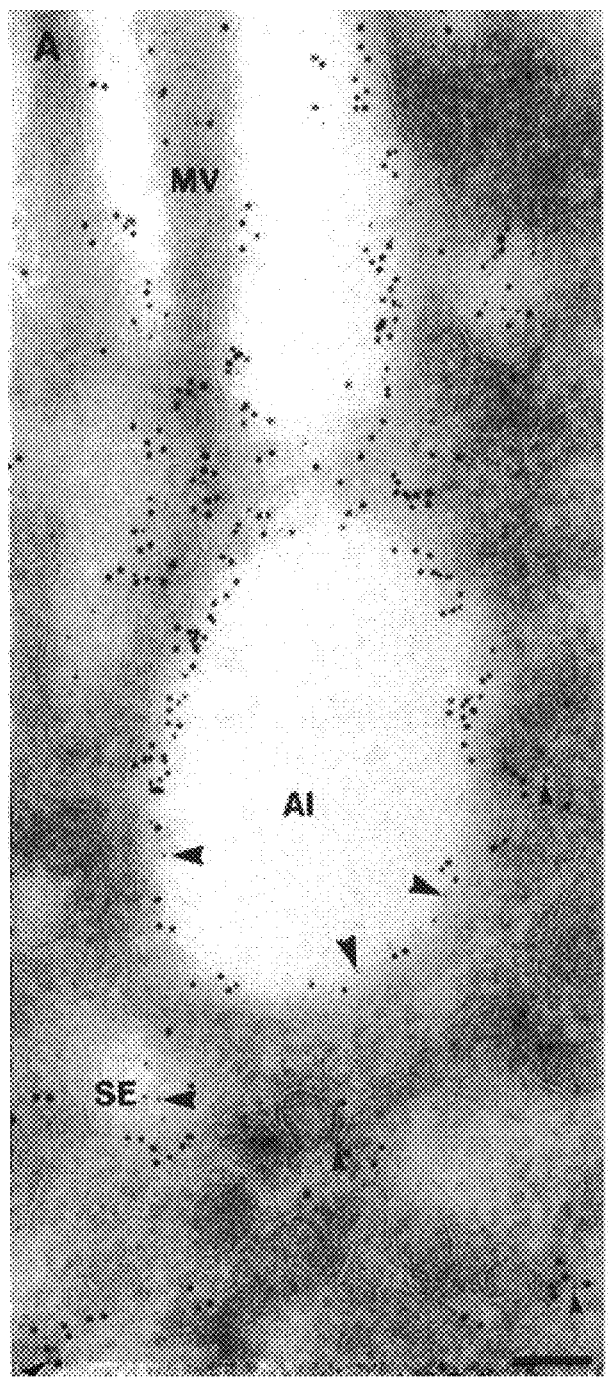
FIG. 8 shows immunocytochemical localization of megalin (10 nm gold) and cubilin (5 nm gold) in the apical part of rat renal proximal tubule cell (FIG. 8A) and epithelial cell of rat yolk sac (FIG. 8B). The two proteins are colocalized in apical endocytic invaginations (AI), small (SE) and large (LE) endosomes, the small gold-particles (cubilin) being indicated by large arrowheads. Colocalization is also seen in dense apical tubules (cubilin, small arrowheads). Microvilli (MV) of the proximal tubule are labeled for both proteins, whereas very little labeling is seen on yolk sac microvilli. Bars, 0.1 μm.
Figure 8B:
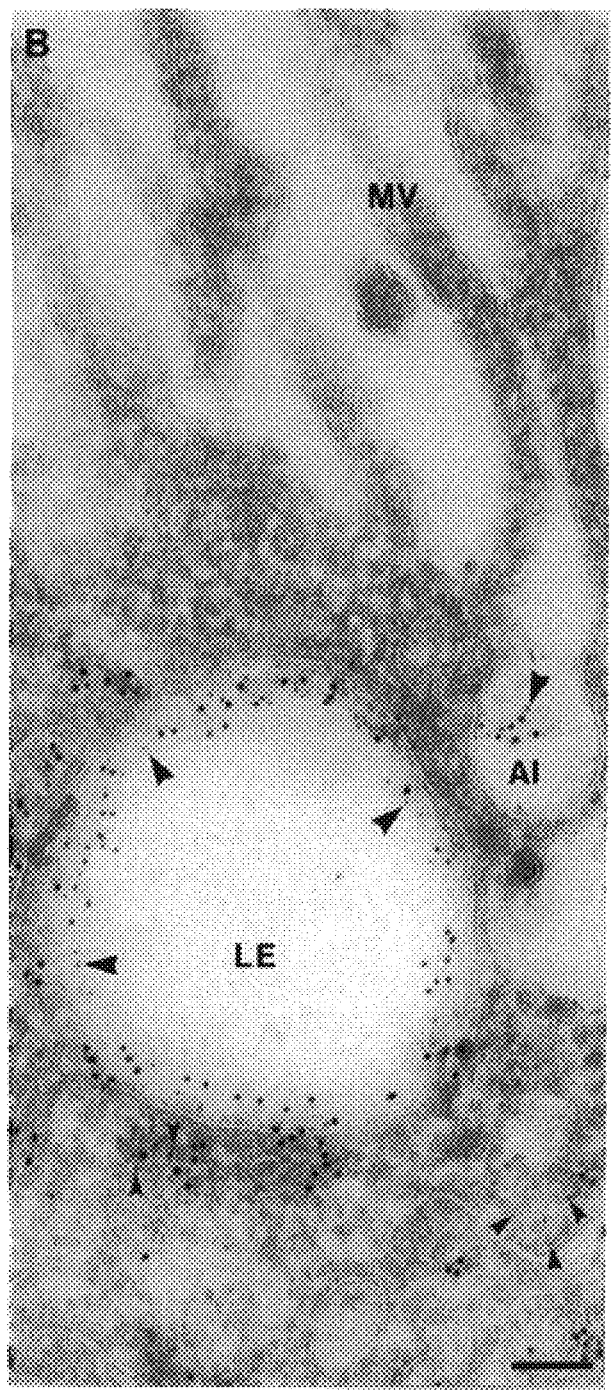

Previous studies have demonstrated megalin and cubilin in endocytic vesicles of the same absorptive epithelia in the intestine, kidney and yolk sac. FIG. 8 shows electron microscopic examination of rat yolk sac and kidney section subjected to double gold-labeling of megalin and cubilin using a sheep anti-megalin polyclonal antibody and a mouse anti-cubilin monoclonal antibody. The large gold particles label megalin antibody and the small particles label cubilin antibody. An almost identical localization of the two sizes of gold particles was seen. Formation of cubilin/megalin complexes was tested next.

Figure 9:
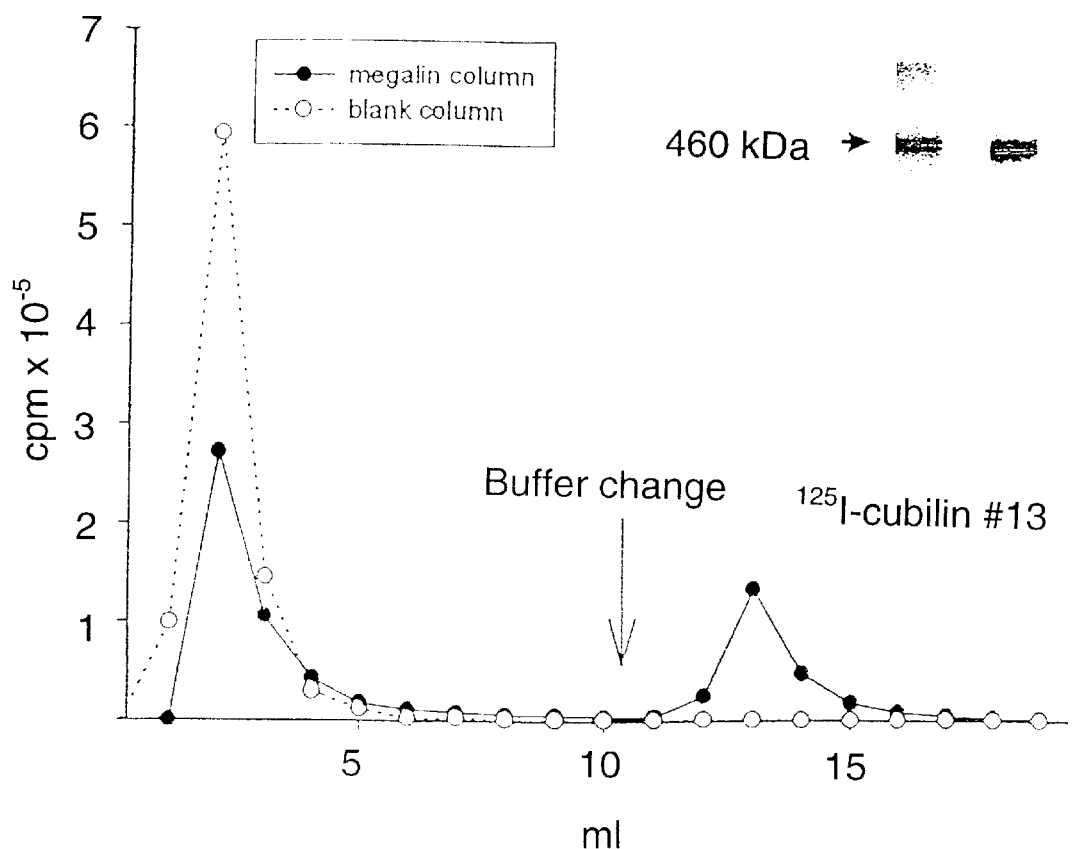
FIG. 9 shows binding of cubilin to megalin as determined by affinity chromatography. $^{125}$I-cubilin was applied to a megalin-Sepharose-4B column (•) or a blank Sepharose-4B column (o). The inset demonstrates autoradiography of SDS-PAGE of $^{125}$I-cubilin and the eluted fraction 13 (#13). Bound radioactivity was eluted by the addition (arrow) of 10 mM EDTA to the running buffer.
Figure 10A:
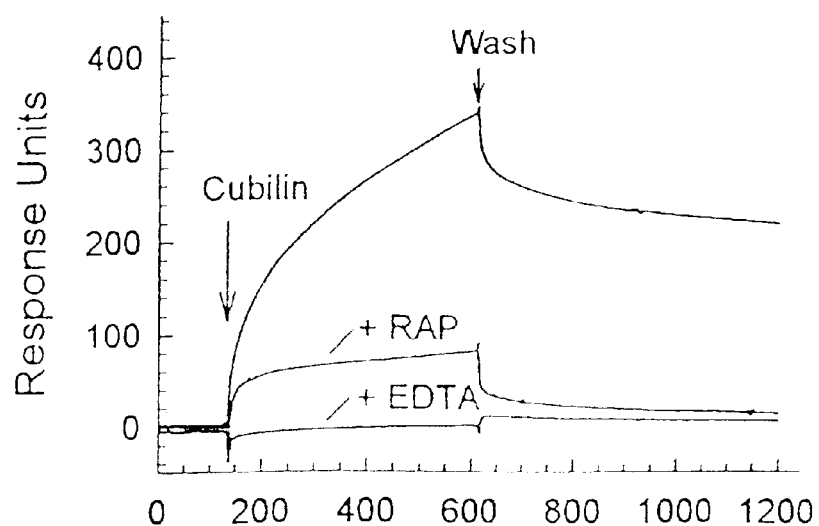
FIGS. 10A–B shows characterization of the cubilin-megalin interaction by surface plasmon reasonance analysis. Rabbit megalin was immobilized to a sensor chip and the on rates and off rates for the binding of cubilin was recorded by flow of 20 nM purified cubilin along the chip surface. For control, cubilin was subjected to a blank chip. The values displayed are the recordings from the megalin-chip subtracted from the recordings from the blank chip.
Figure 10B:
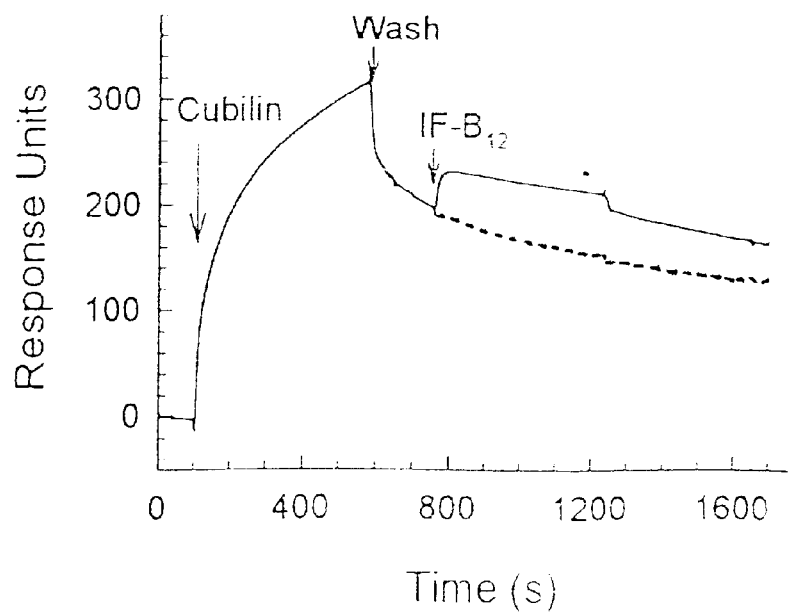

FIG. 9 shows $^{125}I$ cubilin binds megalin covalently linked to Sepharose 4B. Bound radiolabel was released from the column by EDTA. Surface plasmon analysis (FIG. 10A) confirmed this binding. No difference in the dissociation of cubilin to megalin was seen in the pH interval 4–8. Binding of cubilin to megalin was reduced (75%) when RAP was prebound to megalin indicating that cubilin binds to the extracellular domain of megalin. Megalin-bound cubilin was still capable of binding IF-$B_{12}$ as shown by subjecting the megalin-chip to flow with IF-$B_{12}$ after the binding of cubilin (FIG. 10B). Thus, the response after adding IF-$B_{12}$ represents the formation of a megalin-cubilin-IF-$B_{12}$ complex. Control experiments showed no binding of IF-$B_{12}$ to megalin.

EXAMPLE 21

Light Chains are Ligands for Cubilin

Figure 11A:
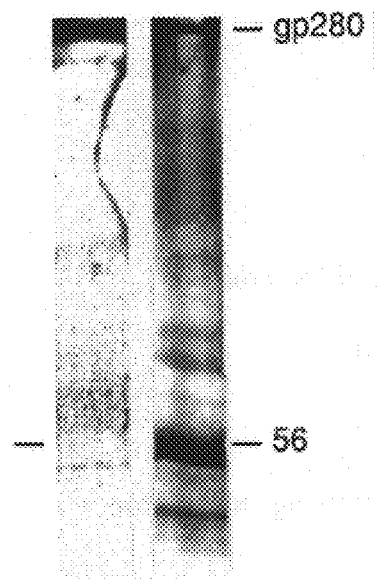
FIGS. 11A–B shows multiple lines of evidence suggesting that cubilin binds light chains.
Figure 11B:
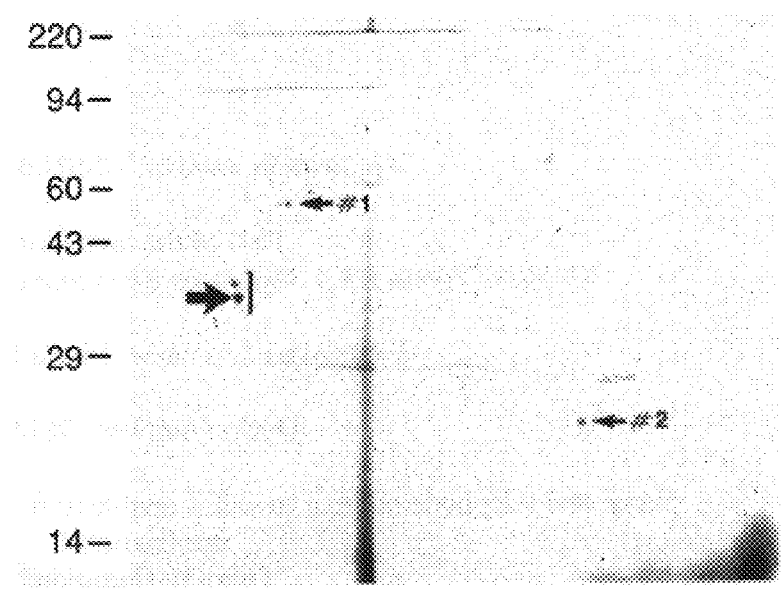

To identify candidate ligands with which cubilin interacts, a detergent extract of rat renal apical intermicrovillar clefts biotinylated on their cytosolic facade to affinity chromatography was subjected. The extract was passed through an immunoaffinity raised against the whole molecule. Western blot analysis of the eluate using the same antibody showed a single band at the region of 460–540 kDa, consistent with cubilin (FIG. 11A, left lane). Coomassie staining of a parallel gel revealed several additional bands (FIG. 11A, right lane). For further characterization, the proteins eluted from the column were separated by two-dimensional gel electrophoresis and transferred, and the spots were cut of the gels (FIG. 11B). Pooled material representing the same spot from multiple gels was C-leu digested, fragments separated by HPLC and microsequenced (Ferrara, et al., 1993). Proteins eluted from the column included cubilin (FIG. 11A, left at top of gel), a 56-kDa protein identified as the β-subunit of the H+-ATPase by the sequence VVDLLAPYA (FIG. 11B, #1), a 24-kDa protein identified as κ-light chains by the sequence (I/S)PQLLVYNA (FIG. 11B, #2), and an internal tropomycin control protein added exogenously to the gel (FIG. 11B, solid arrow). The 56 kDa protein was biotinylated suggesting cytosolic residence, and hence was not pursued as a ligand. The 24-kDa protein was not biotinylated, suggesting exofacial residence (Table 1).

TABLE 1

Analysis of Anti-gp280 Affinity Column Eluate

| Protein W.M. (kDa) | Commassie Stain | Anti-gp280 Western | Cytosolic Biotinylation |
| --- | --- | --- | --- |
| 540 | + | + | + |
| 56 | + | − | + |
| 24 | + | − | − |

Figure 12A:
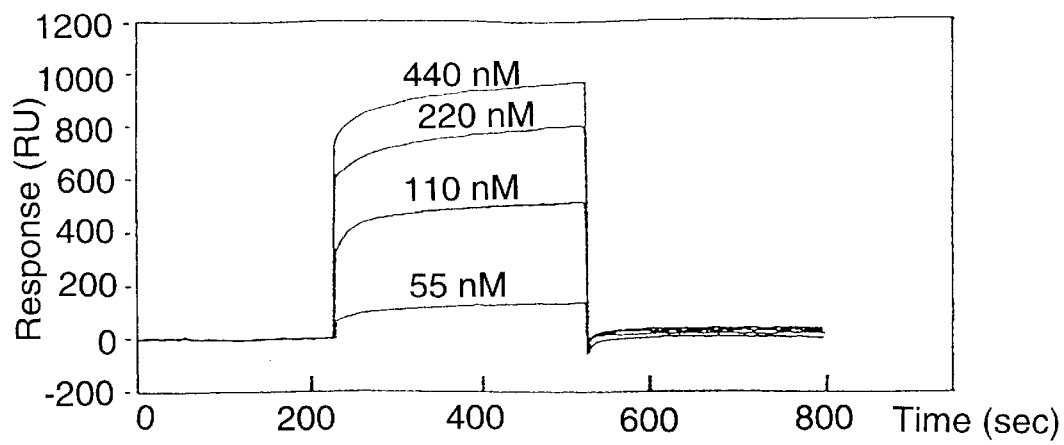
FIGS. 12A–C shows direct binding analysis of cubilin and myeloma light chains by surface plasmon resonance.

Whether light chains are a ligand for cubilin, or were merely eluting from the antibody on the column remained uncertain. Analysis of cubilin binding to κ and λ-light chains using surface plasma resonance techniques provides direct evidence that cubilin binds light chains. A stock solution of cubilin was diluted serially with flow buffer and passed over the immobilized __-light chain surfaces for 5 minutes (50 μl at 10 μl/min., 25° C.), followed by monitoring the dissociation phase induced by introduction of cubilin free-flow buffer for 4 minutes (FIG. 12A). After 4 minutes, the cubilin bound to the surface had dissociated completely, so it was not necessary to regenerate the surface prior to the next injection. The sensorgrams were corrected for bulk refractive index changes by subtracting the response on the blank flowcell from the other flowcells. Cubilin bound to κ-light chains in a dose-dependent fashion (FIG. 12A).

Figure 12B:
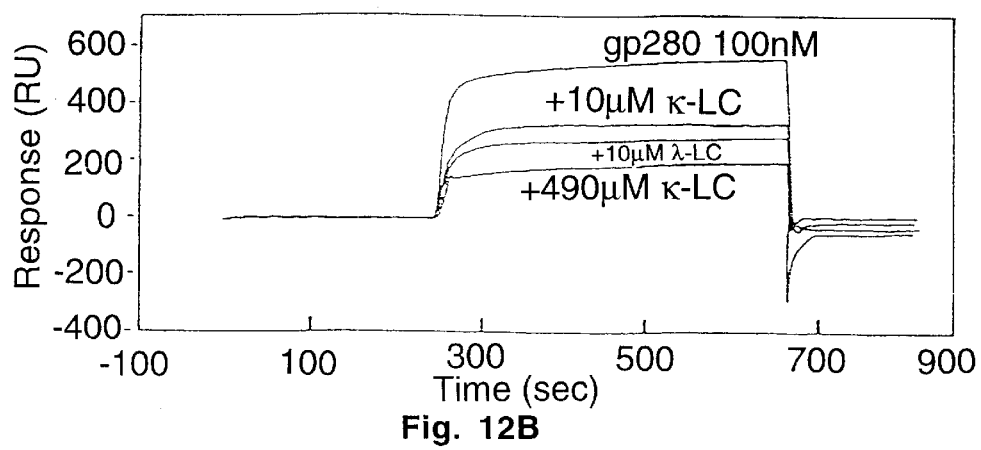

To further demonstrate the binding specificity of the cubilin to the immobilized κ-light chains, a competition experiment was conducted. A sample of cubilin (100 nM) was incubated with κ-light chains (10 or 490 μM), or λ-light chains (10 μM) prior to injecting the sample over the κ-light chain surface. The binding of cubilin to the immobilized surfaces was reduced in the presence of κ-light chains in a dose-response fashion (FIG. 12B). Inhibition of cubilin binding to immobilized κ-light chains with 10 μM λ-light chains suggests κ and λ light chains share a common binding site on cubilin. This series of experiments was repeated with immobilized λ-light chains, and four different light chains competing (two λ and two κ) with similar results (data not shown). These studies showed that cubilin bound λ-light chains in a dose-dependent fashion, and that binding was interfered with in a dose-response fashion by both free λ- and κ-light chains. In these studies, bovine serum albumin neither competed with light chains, nor bound to cubilin.

Figure 12C:
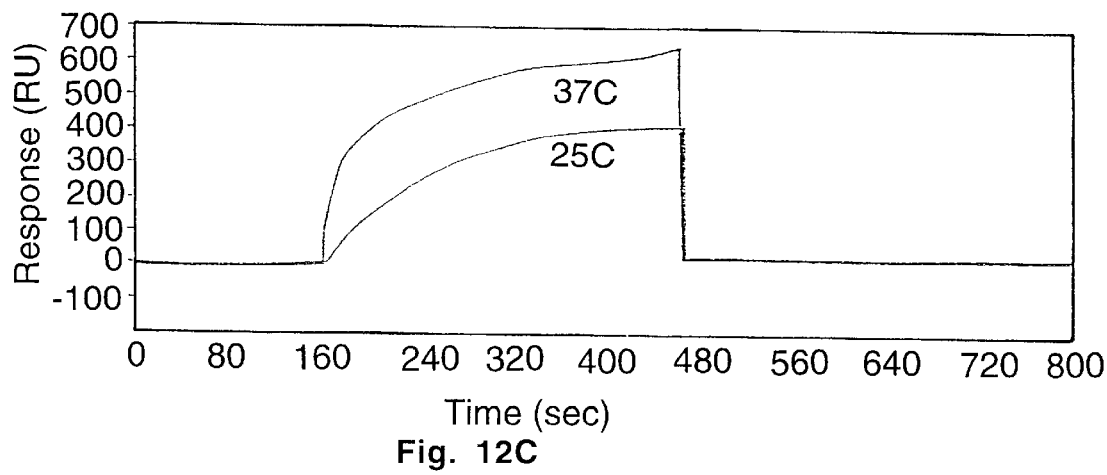

Binding of cubilin to κ-light chains was much greater at 37° C. than 25° C. (FIG. 12C), consistent with known thermal behavior of receptor-ligand interactions (Batuman et al., 1990). Hence, BIACORE surface plasmon resonance analysis allows for direct real time assay of the binding of myeloma light chains to cubilin, providing direct evidence that cubilin is a renal light chain receptor.

Figure 13A:
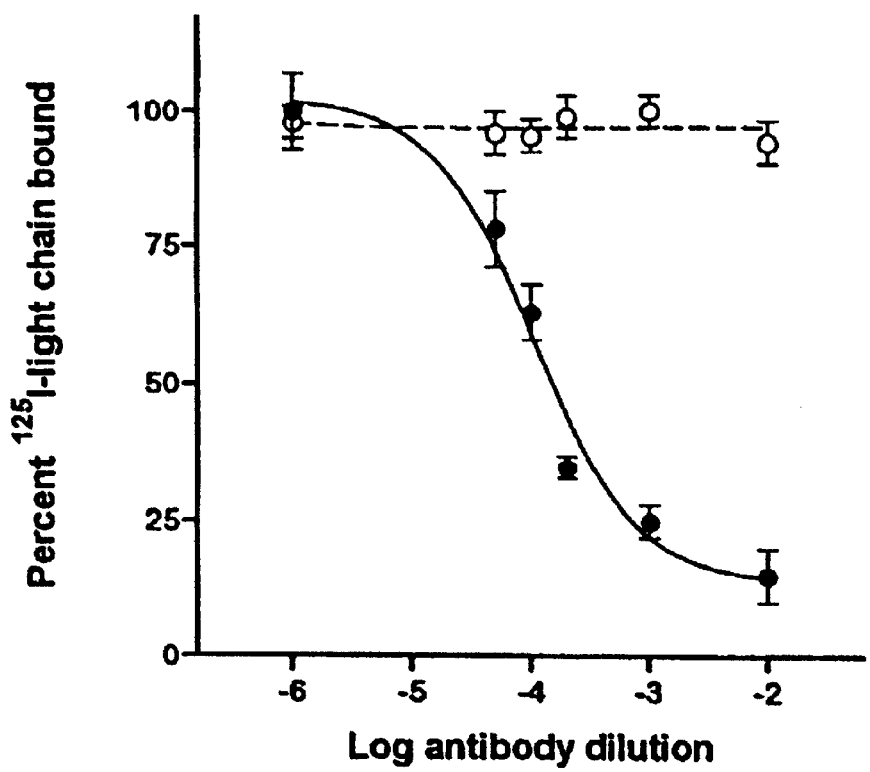
FIGS. 13A–B shows displacement of light chain binding to rat renal cortical brush-border membranes by anti-cubilin and megalin antisera.

To determine whether light chains bind to cubilin present in brush-border membranes in its native membrane-bound form, antibody interference with light chain binding to rat kidney brush-border membrane vesicles, which are known to express cubilin (Sahali et al., 1988), was tested. Binding of [$^{125}$I]-labeled human λ-light chain to rat renal brush-border membrane vehicles is displaced by polyclonal antibodies to cubilin. The half-maximal inhibitory concentration of anti-cubilin antibody was observed at approximately 10,000 dilution (FIG. 13A, solid circles). In contrast, antiserum to megalin, which is known to bind these membranes (Moestrup et al., 1995), had no effect on the binding of this light chain (FIG. 13A, open circles), suggesting that this λ-light chain binds exclusively to cubilin.

Figure 13B:
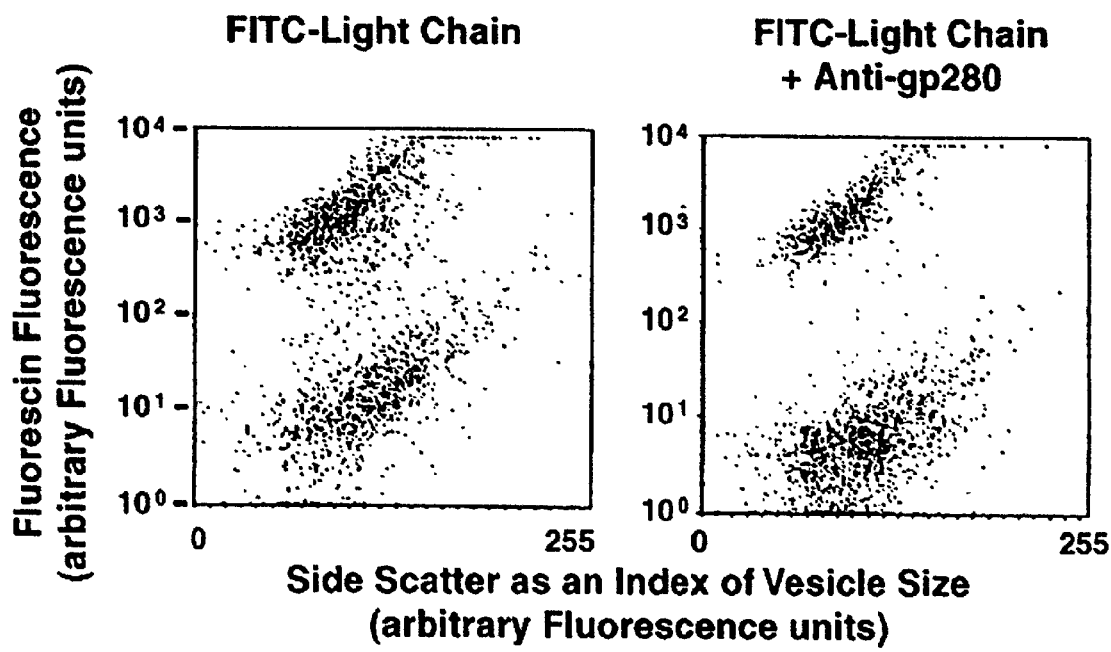

At the maximal inhibitory concentration, the anti-cubilin antiserum displacement of λ-light chain approached 90%, confirming near exclusive binding of this light chain to cubilin. It was also observed that binding of human FITC-conjugated κ-light chain to rat renal brush-border membrane vesicles was displaced by polyclonal antibodies to cubilin as assayed by flow cytometry (FIG. 13B). Light chain binding (45.5±4.3 arbitrary fluorescent units, n=8) increased compared to unstained membranes (5.1±1.2 units, n=8, p<0.05), and was displaced by anti-cubilin (30.2±_1.0 units, n=8, p<0.05). There was no effect on light chain binding by normal rabbit serum (42.9±1.7 units, n=8), or antiserum to the neurokinin-1/substance-P receptor (40.0±1.2 units, n=4), an irrelevant antibody which binds these membranes. This provides additional evidence that the competitive effect of cubilin antiserum on the binding of light chain is specific. Flow cytometry histograms of light chain binding on a vesicle-by-vesicle basis illustrate the effects of cubilin antisera on rat renal brush border binding of FITC-κ-light chains. Each histogram (FIG. 13B) displays 2000 vesicles as individual dots, with FITC fluorescence plotted against vesicle size. FITC-light chains bind most but not all brush borders (FIG. 13B, left panel). Cubilin antiserum displaced FITC light chain binding (FIG. 13B, right panel).

Figure 14A:
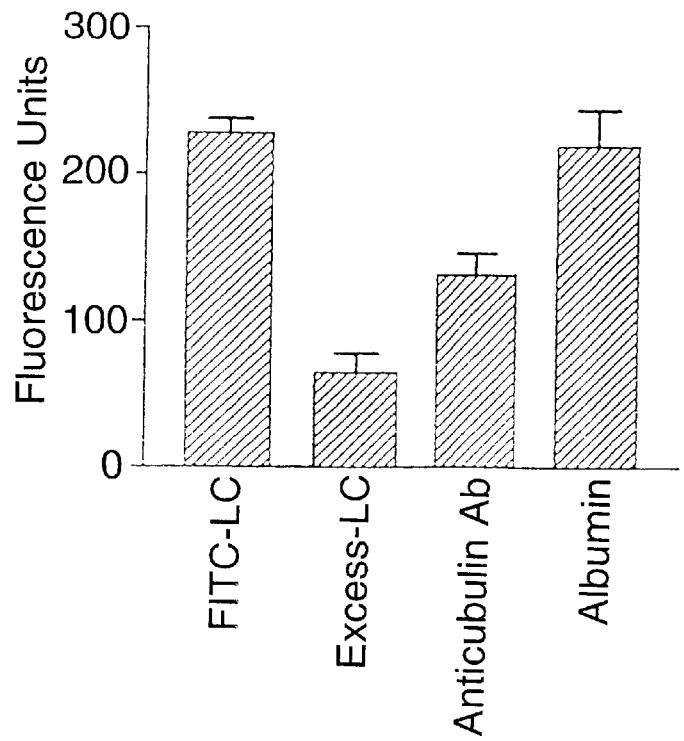
FIGS. 14A–B shows effects of anti-cubilin antibody on light chain endocytosis.
Figure 14B:
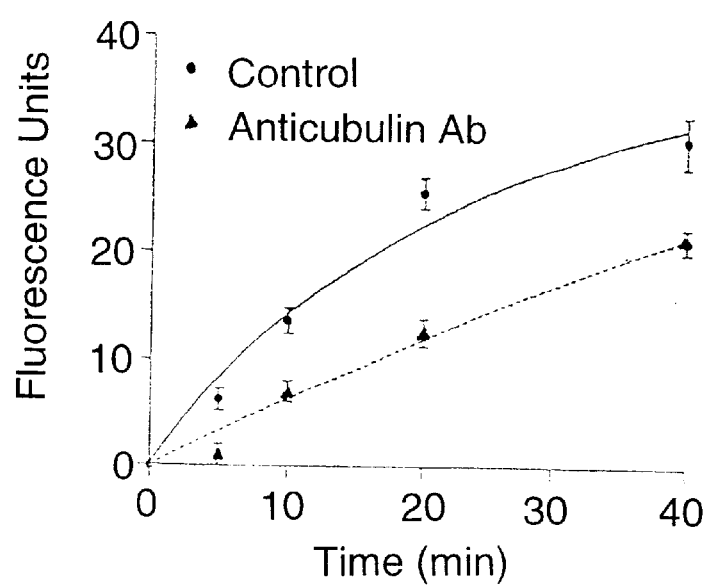

To examine the role of cubilin in light chain endocytosis, yolk sac cells were allowed to endocytose FITC-light chain in the absence and presence of anti-cubilin antiserum. These endocytosis experiments revealed a significant inhibitory effect but not total elimination of endocytosis (FIG. 14). Excess unlabeled light chain and anti-cubilin antibody reduced FITC-light chain endocytosis significantly (n=4, p<0.002, Mann-Whitney-U test), whereas albumin had no effect (FIG. 14A). Furthermore, a time course study showed that anti-cubilin antiserum inhibited light chain endocytosis significantly at all time intervals studied (FIG. 14B, n=3 each time period, p<0.0001). This time course experiment also showed that anti-cubilin antiserum eliminated the saturable pattern of endocytosis with apparent linearization of the uptake curve (FIG. 14B). This observation further supports that cubilin mediates light chain endocytosis in yolk sac cells. Less than complete inhibition of light chain endocytosis in the presence of anti-cubilin antiserum also indicates that, when this pathway is blocked, some light chain endocytosis occurs through alternate pathways, and that the cubilin-facilitated path is not exclusive endocytic pathway for light chains.

EXAMPLE 22

Function of Light Chains on Endosomal Fusion

Figure 15:
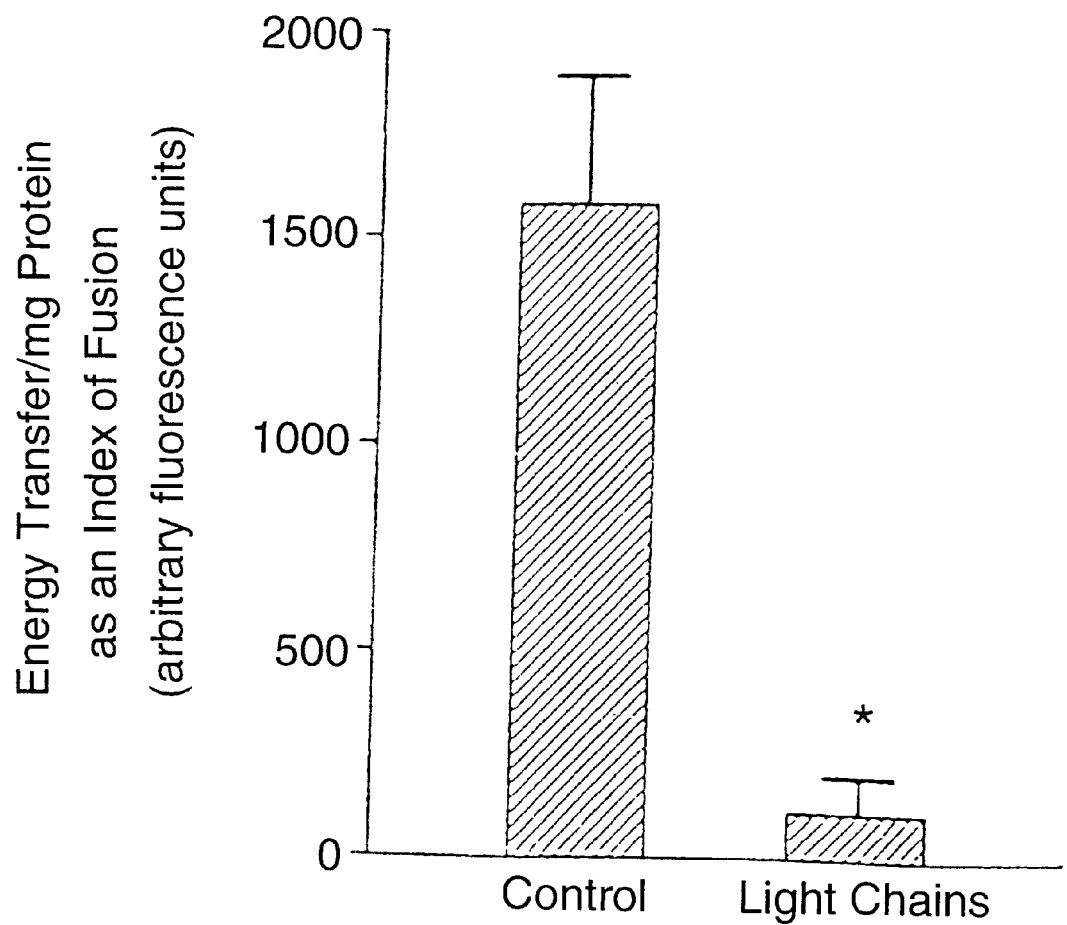
FIGS. 15A–B shows direct effects of light chains on endosomal fusion reconstituted in vitro. The λ_light chains were loaded into rat renal cortical intermicrovillar cleft at 400 _M by addition to the homogenization buffer. Fusion reconstituted in vitro in light chain-loaded membranes was inhibited compared with albumin-loaded control membranes. Values are mean±standard error for n=8, p<0.05 by unpaired t-test.

To test whether myeloma light chains are functionally important in membrane trafficking and fusion events, intermicrovillar clefts were loaded with light chains by adding it to the homogenization buffer (Hammond et al., 1994). Fusion reconstituted in vitro in cuvettes was assayed by energy transfer, and results were normalized per milligram protein (Hammond et al., 1994; Jo et al., 1995). Fusion was significantly inhibited in membranes treated directly with light chains (111±89 arbitrary fluorescence units/mg protein, n=8) compared with albumin entrapped controls (1584±314, n=8, p<0.0003 by unpaired t-test, FIG. 15).

EXAMPLE 23

Myeloma Light Chains Bind Megalin

Figure 16:
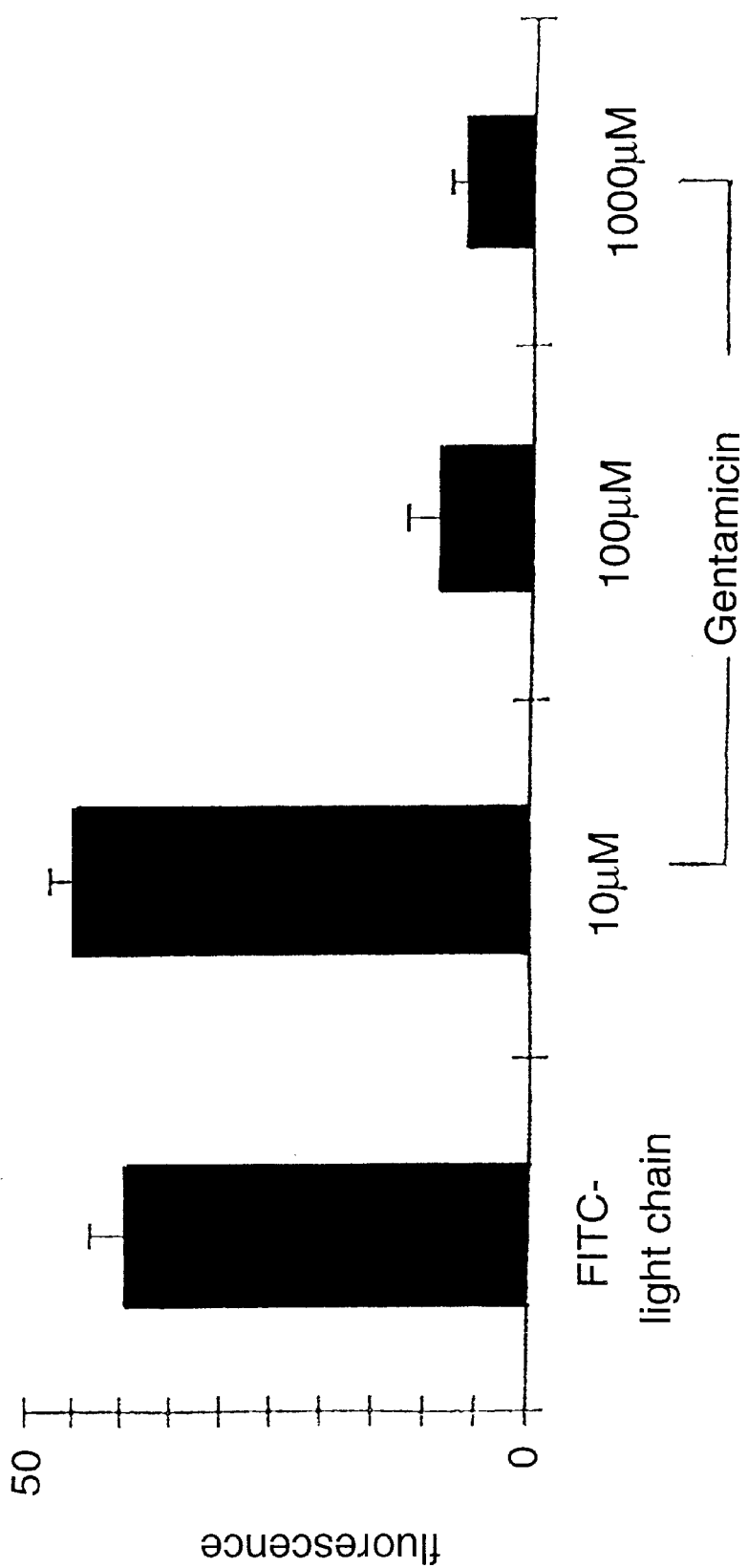
FIG. 16 shows fluorescein-light chain binding to renal brush-border membrane vehicles in the presence of gentamicin by flow cytometry, demonstrating megalin is a light chain receptor.

Given the abundance of megalin on the renal brush border membrane, if megalin is a light chain receptor this would predict that small polybasic drugs, such as gentamicin, which are known ligands for megalin, should compete for light chain binding to renal brush border membrane vesicles. To test this, rat renal brush border membrane vesicles were incubated in fluorescein-conjugated light chains with various concentrations of gentamicin. After washing, fluorescein-light chain binding to the membranes was analyzed by flow cytometry (FIG. 16). Estimate of half maximal binding concentration of gentamicin between 60 and 70 $\mu M$ was placed in the middle of the curve. Gentamicin competes with fluorescent light chain binding to renal brush border membranes in a dose-dependent manner (control FITC-light chain binding 39.6±4.2 arbitrary fluorescence units, 10 $\mu M$ gentamicin 45.1±3.1, 100 $\mu M$ gentamicin 8.9±33.8*, 1000 $\mu M$ gentamicin 6.3±1.9*, n=4, *p<0.05). This demonstrates that gentamicin competes with light chains for brush border membrane binding.

EXAMPLE 24

Extra Renal Expressipon of Cubilin

Figure 17A:
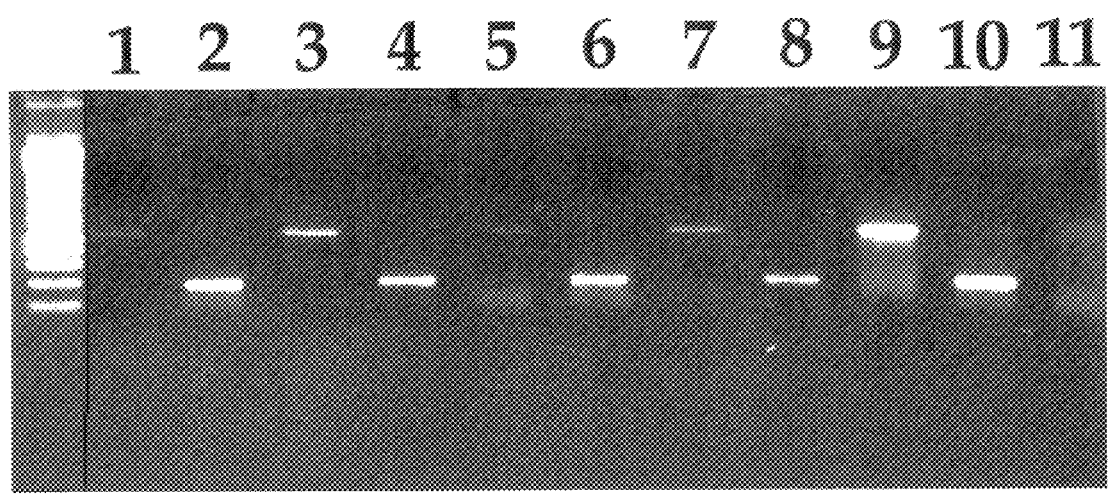
FIGS. 17A–B shows extra renal expression of cubilin.
Figure 17B:
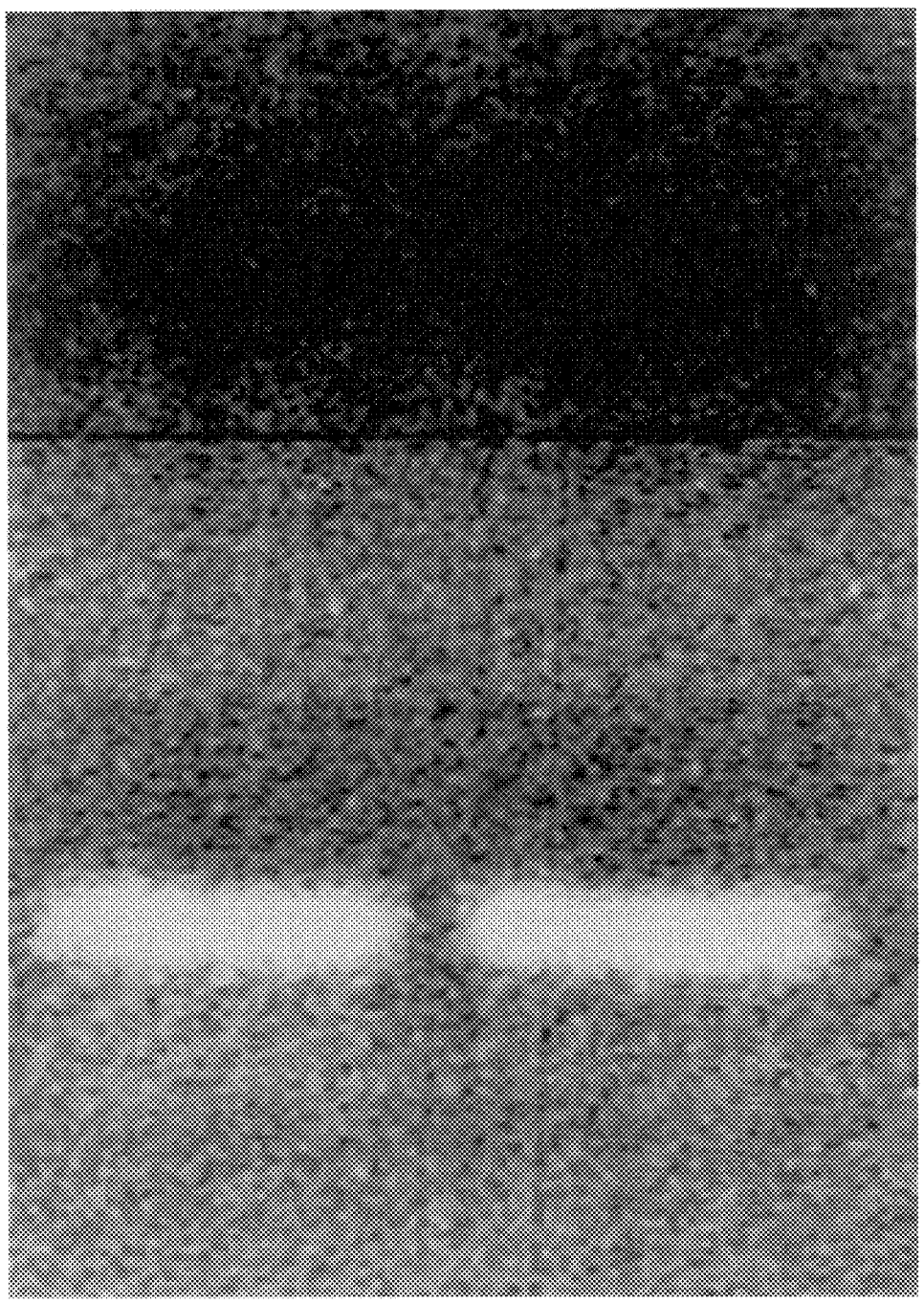

Cubilin was demonstrated to be expressed in extra-renal tissues as well (FIGS. 17A and 17B). Spleen, brain, liver, heart, kidney and thyroid are the possible sites where cubilin is expressed. Administering cubilin in a pharmaceutically acceptable carrier might lead to the reduction of toxicity and therefore protecting those sites.

EXAMPLE 25

Urine Cubilin

Figure 18:
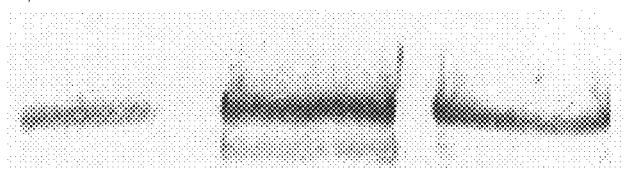
FIG. 18 shows urine cubilin. Normal rat urine (lane 1) and 2 separate preparations of rat renal brush border (lanes 2–3) were separated by PAGE-SDS, transferred onto nitrocellulose and probed with anti-cubilin antibodies.

Cubilin was also detected in the urine (FIG. 18), which indicates that cubilin is released into the urine and the assay of urinary cubilin might be an excellent marker for detecting renal damage. Several conditions can be considered: 1) renal damage of acute origin may increase the excretion of a tubular protein such as cubilin and constitute a more sensitive and specific marker than adenosine deaminase (Iglesias et al., 1994; Parvez et al., 1990; Tolkoff-Rubin et al., 1987); 2) chronic renal damage with tubular atrophy may be associated on the other hand with a reduced expression of cubilin, the assessment/follow up of which may be useful to monitor the evolution of renal fibrosis; 3) because Imerslund Grasbeck (IG) patients do not all have proteinuria, it is likely that the syndrome is associated with various mutations of cubilin (for comparison one or two hundred have been described in familial hypercholesterolemia) which may be associated with variable levels of cubilin excretion. In fact the assay of IF-$B_{12}$ binding activity of the urine of IG patients has been studied (Dugue et al., 1998; Gueant et al., 1995); and 4) some diseases characterized by proteinuria of unknown cause may be due to a defect in cubilin, which may be absent and therefore not detectable in the urine, or excreted in large amounts if it is not gathered adequately to the membrane.

More generally it can be presumed that mutations of key receptors of trophoblastic cells, such as cubilin may account for a variety of pathologies. For instance, the ulk of fetal malformations, not accounted for by the known or suspected hereditary abnormalities, might be related to cubilin defect. Similarly, most cases of poor fetal development or fetal loss, which are of unknown origin up to date, might be caused by cubilin mutations.

The present study provides novel molecular information on cubilin, previously known as the yolk sac target antigen of teratogenic antibodies and the intestinal receptor for IF-$B_{12}$. The primary structure predicts 35 extracellular modules uniquely organized in a cluster of 8 EGF repeats followed by, from a molecular point of view, an huge cluster of 27 CUB domains which account for 88% of the mass of the protein. Northern and western blotting of kidney, yolk sac and intestine indicate no difference in size of the receptor in these organs.

The EGF type B repeats are similar to the carboxyl-terminal extracellular modules of megalin and low density lipoprotein receptor-related protein. Cubilin has otherwise very little homology to these two giant receptors, which also bind RAP and mediate endocytosis of a variety of ligands. Also cubilin does not display homology to sortilin, the 95 kDa putative vesicular sorting receptor, which also binds RAP (Petersen et al., 1997). The CUB domains conform to the description of Bork and Beckmann (1993) based on the analysis of 31 copies of a module initially identified in C1r and C1s components of complement and subsequently in a variety of proteins associated with fetal development. They consist of 110 amino acids defining a characteristic hydrophobicity pattern predicted to form antiparallel beta barrels (Dias et al. 1997). The four conserved cysteines, generally thought to form two S-S bridges (1-2, 3-4), are found in all but domain 13 of cubilin which lacks the first 2 cysteines as already described in the first CUB domains of C1r/s and the homologues MASP1/2. When analyzed individually, the CUB domains of cubilin are more closely related to those seen in developmental control proteins.

On the functional level there is compelling evidence that the CUB domains are involved in the binding of proteins, as described for the $Ca^{2+}$-dependent formation of the C1 complex (Bosby and Ingham 1990), as well as for binding of phospholipids and carbohydrates, as demonstrated for spermadhesins (Calvete et al. 1996a and 1996b, Dostalova et al. 1995). In addition to the CUB domains, the EGF repeats might also account for some of the binding properties of cubilin. EGF repeats are widely expressed and involved in a number of receptor-ligand interactions (Davis 1990). Two of the EGF repeats in cubilin have the consensus sequence for calcium binding (Rao et al. 1995) and may be involved in the calcium-dependent binding of e.g. RAP or IF-$B_{12}$.

The lack of a transmembrane segment was surprising since in previous studies isolation of cubilin relied on the use of detergent solubilized membranes. Furthermore the previous studies showed that cubilin was internalized through clathrin coated organelles and recycled via dense apical tubules (Le Panse et al. 1995). This first suggested to reassess membrane tethering of cubilin. Early results was thus confirmed indicating that an intrinsic factor-$B_{12}$ binding protein (Cotter and Rothenberg 1976) and the target of teratogenic antibodies (Leung 1982) could be released at least in part from intestinal or renal tissue using mechanical dissociation in the absence of detergents. It was further showed that whereas membrane association was stable between pH 4 and 8 cubilin could be released by heparin, phosphorylethanolamine and EDTA. These observations, which indicate nonionic interactions with sugars and phospholipids, are in line with the membrane binding properties of spermadhesins which consist of a single CUB domain, lack a transmembrane segment, but are yet tightly bound to the surface of sperm cells via phospholipids (Dostalova et al. 1995). Another region of the same CUB domain binds to carbohydrates of zona pellucida, the extracellular investment surrounding the mammalian egg. The lectin binding characteristics of the spermadhesins are not fully characterized but include heparin and a variety of carbohydrates including Gal beta (1-4)-GlcNac and Gal beta (1-3)-GlcNac (Calvete et al. 1996,1997). In view of the 27 CUB domains present in cubilin this receptor may have multiple membrane attachments which may account for the inability to release all the membrane associated cubilin.

The identification of the components which link cubilin to the membrane is also essential for understanding its internalization and recycling. The present study suggested that the binding of cubilin to megalin is crucial for this process. Co-internalization of a receptor which lacks internalization signal(s) by means of another receptor has previously been shown. The GPI linked urokinase receptor can thus be endocytosed by coupling of urokinase receptor-bound urokinase/inhibitor complex to the LDL receptor-related protein (Nykjær et al. 1997, Conese et al. 1996). It is likely that a similar process can be mediated by megalin which can also bind the urokinase-inhibitor complex (Moestrup et al. 1993). Based on the strict colocalization of cubilin and megalin at the subcellular level and on the ability of megalin to bind cubilin in vitro, it was proposed that megalin is crucial for the internalization of cubilin and cubilin ligand complexes. After internalization, the ligand IF-$B_{12}$ is segregated from the receptor and directed to lysosomes for degradation of IF (Dan and Cutler 1994, Birn et al. 1997) whereas cubilin is recycled to the membrane. Since the cubilin/megalin complex is stable at pH 5, the two receptors might remain in complex during the entire recycling pathway at variance from the urokinase receptor which recycles to the plasma membrane without being linked to the LDL receptor-related protein (Nykjær et al. 1997).

Upon analysis of the effect of polyclonal megalin antibodies and RAP on the endocytosis of $^{125}$I-IF-$B_{12}$ in cultured yolk sac cell, only a 10 to 15% reduction was found in uptake. This modest effect might be accounted for a short cell surface expression of megalin and cubilin due to rapid recycling of the two proteins and thereby a too short time for the cubilin-megalin to dissociate, a prerequisite for RAP to block binding. Furthermore, a continuous incubation with RAP will probably have no effect on intracellular receptors, since externally receptor-bound RAP is transported to lysosomes for degradation (Iadonato et al., 1993).

In order to further characterize the partnership of these two giant receptors, studies have been initiated to investigate cubilin trafficking in megalin deficient or megalin-mutated cells expressing cubilin. However, such analysis might be complex since recent data on megalin deficient mice indicate a key role of megalin for normal development of the endocytic apparatus in the proximal kidney tubules and for survival of the mice in general (Willnow et al. 1996).

The observation that the target of teratogenic antibodies contains CUB domains is of particular interest in view of the fact that these domains are often observed in developmentally regulated proteins. The mode of action of the teratogenic antibodies is not known but have been shown to inhibit endocytosis, thus reducing the amount of maternal proteins internalized and consequently the amount of protein derived amino acid which can be incorporated into embryonic tissue (Beckman et al., 1997; Lloyd, 1990, Le Panse et al., 1994). However, there is no direct evidence that a decreased amino acid supply is responsible for foetal malformations. Alternatively, the teratogenic effect might relate to a more specific disturbance of the materno-foetal barrier such as an impaired transfer of $B_{12}$ or of other nutrients. Interestingly, the pattern of antibody induced fetal malformations which includes abnormal cranio-facial development, in particular of the eyes and hypophysis (Sahali et al., 1988) resembles to some extent the holoprosencephalic syndrome induced by anti-cholesterol agents (Llirbat et al. 1997), knock out of the cholesterol-depedent Sonic hedgehog (shh) gene (Porter et al., 1996) or of the megalin gene (Willnow et al., 1996). It has been proposed (Herz et al., 1997) that the defective development of the central nervous system in megalin-deficient mice was related to a decreased megalin-mediated uptake of cholesterol-containing lipoproteins which in turn altered the addition of cholesterol to the shh protein. It is therefore possible that anti-cubilin antibodies could interfere with cholesterol uptake either directly or indirectly via binding of cubilin to megalin in the yolk sac.

The present study establishes cubilin as a novel type of peripheral membrane receptor with multiple potential sites for interaction with other proteins and membrane components. Cubilin can bind IF-$B_{12}$, RAP, megalin, and most likely calcium, phospholipids and carbohydrates (Table 2). However a number of ligands may remain to be identified in order to explain the role of the receptor in kidney function and its importance in fetal development.

TABLE 2

Ligands for Cubilin

| Ligand | BN cell uptake | surface plasmon resonance | antibody interference | competition with known ligands |
|---|---|---|---|---|
| light chains* | X | X | X | X |
| myoglobin | | X | X | X |
| metallothionein | | X | X | X |
| haptoglobin | | | X | X |
| polybasic drugs | | X | X | X |
| Intrinsic factor vitamin $B_{12}$ | | X | X | |
| LDL | X | | | X |
| HDL | X | | | X |
| transferrin | X | | | |
| RAP | | X | X | X |
| albumin | X | X | X | X |

*as light chains compete with renal brush border membrane binding with multiple other medically and physiologically important proteins, this suggests that these proteins are also ligands for cubilin. This group of proteins include β2 microglobulin, amyloid, insulin, cytochrome c and interferon.
LDL: Low density lipoprotein; HDL: High density lipoprotein; RAP: Receptor related protein.

Solution structure of spermadhesin PSP-I/PSP (Romero et al. Nat. Struct Biol 1997 10:78–788), a dimer which consists exclusively of two single CUB domains has recently been obtained. It reveals that CUB domains are characterized by 2 layers of 5 beta sheets, the top layer of one of the CUB domains contacting the lower layer of the other CUB domain in a manner that leaves preferentially exposed the less conserved beta turns which carry the ligand binding sites. If such an arrangement prevails in cubilin, it is likely to account for and one would predict a wide variety of ligands binding to distinct CUB domains.

Indeed the fact that RAP binds cubilin but does not inhibit binding of IF-$B_{12}$ complexes indicates that these 2 ligands bind to different sites and probably to different CUB domains. Similarly haptoglobin and light chains both bind cubilin but do not compete for binding. The modular structure of cubilin thus strongly suggests that it may be feasible to produce fragments of small size corresponding to one or a few CUB domains which can be used therapeutically: this type of fragments will bind selected ligands but preserve many/most other functions of cubilin.

The present studies also showed that cubilin, a giant receptor which participates in the endocytic scavenger pathway of the renal proximal tubule cells, binds and facilitates endocytosis of immunoglobulin light chains isolated from the urine of myeloma patients. Evidence that cubilin is a light chain receptor came from the analysis of eluates from an affinity column prepared with anti-cubilin antiserum in which cubilin coeluted with κ-light chain. The κ-light chain was definitively identified by microsequencing after isolation by two-dimensional electrophoresis. Several additional lines of evidence add weight to the hypothesis that cubilin is a light chain receptor. Competition experiments by anti-cubilin antiserum and surface plasmon resonance experiments both showed that all tested light chains bind to cubilin.

Surface plasmon resonance technology allowed direct analysis of the binding of light chains to cubilin. Several characteristics of the observed sensorgrams suggest that light chains bind cubilin specifically. First, cubilin bound to light chains in a temperature- and dose-dependent manner whether κ or λ-light chain is immobilized. Second, four species of non-immobilized light chains all interfered with binding in a dose-dependent manner. Third, the kinetics of binding and displacement were very similar to values reported using radioactive membrane binding techniques (Batuman et al., 1997; Driesbach et al, 1994; Marchalonis et al., 1992). Lastly, λ-light chains interfere with λ-light chain binding to cubilin and vice versa. This data revalidates the use of surface plasmon resonance technology to quantitate low affinity binding (Jonsson et al., 1991; Sanders et al., 1988).

As κ-light chains are 100-fold more abundant than λ-light chains in healthy animals and humans (Riedel et al., 1991), it is not surprising to observe κ-light chains eluting from the cubilin affinity column but not λ-light chains. The current surface plasmon resonance data provides direct evidence confirming and extending the observation made by membrane binding of light chains: both κ- and λ-light chains are ligands for cubilin.

Studies of classic binding kinetics utilizing Scatchard analysis demonstrate several ligands competing with light chain for brush border membrane binding. These ligands include lysozyme, insulin, cytochrome c, myoglobin and $\beta_2$-microglobulin (Batuman et al., 1990; 1997; Driesbach et al., 1994). Competition by low molecular weight proteins raise the probability that cubilin is a multi-ligand receptor responsible for the endocytosis and cellular trafficking of a number of proteins normally filtered in the glomerulus and catabolized in the kidney, extending the role of this scavenger pathway receptor to such diverse phenomena as rhabdomyolysis and insulin metabolism. The multiple putative ligands for cubilin reflect the precedent set by other giant glycoprotein receptors such as the low-density-lipoprotein receptor, megalin, and the $\alpha_2$-macroglobulin receptor, which bind many ligands with a spectrum of affinities at multiple binding sites (Moestrup et al., 1994). Cloning data that reveal multiple EGF repeats and CUB domains strengthens this expectation.

Receptor kinetic studies have demonstrated that light chain binding to receptors in cultured proximal tubule cells is followed by endocytosis and ultimate lysosomal degradation. The present observations suggest that cubilin is a receptor that can mediate endocytosis of light chains in renal proximal tubular cells. Nearly 90% of the λ-light chain binding was displaced by anti-cubilin antibody. In contrast, anti-megalin antibody did not compete with the brush border binding of this light chain at all. This suggests that cubilin is the quantitatively major receptor for this λ-light chain. However, at maximal inhibitory concentration of the anti-cubilin antibody, 10% of light chain remained bound to brush border membranes, suggesting presence of additional binding sites for this light chain.

Anti-cubilin antiserum also inhibited endocytosis of light chain significantly. This further confirms that cubilin binding is followed by endocytosis of light chain. However, less than total inhibition of light chain endocytosis by anti-cubilin antibody indicates that this pathway may not be the exclusive endocytic pathway for light chains and that there may be alternate pathways which can compensate partially when the cubilin-mediated pathway is blocked. The antibodies used in the present study may be less than blocking functionally, and incomplete inhibition of endocytosis may be on this basis.

Importantly, binding of light chains to scavenger pathway receptors is not just a structural observation, as light chains had potent direct effects on endosomal fusion reconstituted in vitro. This raises the novel hypothesis that ligand binding may affect fusion properties of membranes, mediated by the receptors they bind. Select ligands are known to induce endocytosis of the ligand-receptor complex by binding, and the protein components of the final common pathway of fusion have largely been identified and cloned. These mechanisms may provide new insights into nephrotoxicity of myeloma light chains and other nephrotoxic low molecular weight proteins.

There are 13,500 new cases of myeloma annually in the U.S. and 1–4 new cases/100,000 of population worldwide. Although the precipitation of light chains with Tamm-Horsfall protein to form casts in renal distal nephron segments has been defined down to specific peptide sequences, the molecular characteristics of receptors that mediate the endocytosis of light chains in the proximal tubule have not been defined. Identification of the proximal tubular receptor for light chains extends and compliments these observations. The proximal tubule determines the distal delivery of low molecular weight proteins by reabsorbing the bulk of filtered proteins including light chains. Many low-molecular weight proteins induce injury to the proximal tubule, while others precipitate in the distal nephron. Both these mechanisms contribute to the pathogenesis of tubulointerstitial nephropathies associated with low-molecular-weight proteins, such as multiple myeloma. Proximal reabsorption of light chains is associated with tubular atrophy, necrosis and Fanconi syndrome. Taken together with understanding of distal tubular cast formation, identification of major renal binding proteins for myeloma light chains in the proximal tubules will allow detailed characterization of the binding site between cubilin and light chains, as well as other nephrotoxic low-molecular weight proteins. This completes the necessary mechanistic data of all affected nephron sites for the rational design of agents to protect from nephrotoxicity caused by myeloma light chains as well as other low-molecular weight proteins.

The present studies also demonstrate several lines of evidence suggesting that light chains are a ligand for megalin:

anti-megalin antiserum partially displaces brush border light chain binding, and gentamicin displaces brush border light chain binding. Independent evidence suggests that cubilin is a receptor for polybasic drugs as gentamicin directly interferes with light chain binding to cubilin in vitro. These observations are important, both to understand the complex interactions of toxic and physiological ligands on proximal tubule scavenger pathway receptors, as well as the eventual development of clinical protective agents for nephrotoxic damage mediated by ligands for cubilin and/or megalin.

The following references were cited herein.

Baricault et al., *Biochem Biophys Res Commun* 212:353–359, 1995.
Batuman et al., *Am J Physiol* 258 (*Renal Fluid Electrolyte Physiol* 27): F1259–F1265, 1990.
Batuman et al., *Am J Physiol.* 272 (*Renal Fluid Electrolyte Physiol* 41):F521–F530, 1997.
Bennett et al., *Proc. Natl. Acad. Sci. USA* 90: 2559, 1993.
Bork et al., *J Mol Biol.* 231, 539–45, 1993.
Brent et al., *Proc. Soc. Exp Biol. Med.* 106:523–526, 1961.
Busby et al., *Biochemistry* 29, 4613–4618, 1990.
Bu et al., *J. Biol. Chem.* 271, 22218–24, 1996.
Calvete et al., *Biol. Chem* 377, 521–527, 1996.
Conese et al., *J. Cell Biol.* 131, 1609–1622, 1996.
Cotter et al., *J. Haematol.* 34, 477–87, 1976.
Dan et al., *J. Biol. Chem.* 269, 18849–18855, 1994.
Davis, *The New Biologist* 2, 410–419, 1990.
Dias et al., *Protein Sci.* 6, 725–7, 1997.
Dostalova et al., *Biol. Chem. Hoppe Seyler* 376, 237–242, 1995.
Driesbach et al., *Renal Physiology* 17:287–293, 1994.
Dugue et al., *J Pediatr Gastroenterol Nutr* 26(1):21–5, 1998.
Farquhar et al., *J. Am Soc. Nephrol.* 6, 35–47, 1995.
Ferrara, et al., Chemistry IV" (ed. R Angeletti) p 379–387, 1993.
Fyfe et al., *J. Biol. Chem.* 266, 4489–94, 1991.
Grasbeck et al., *Acta Med. Scan.* 167, 289–296, 1960.
Gueant et al., *Gastroenterology* 108,1622–1628, 1995.
Hishida et al., *EMBO J.* 15, 4111–22, 1996.
Hammond et al., *Kidney Int* 42:997–1005, 1992.
Hammond et al., *Am J Physiol* 272 (*Renal Fluid Electrolyte Physiol* 41) :F117–F123, 1997.
Hammond et al., *Cytometry* 14: 411–420, 1993.
Hammond et al., *Am J Physiol* 267 (*Renal Fluid Electrolyte Physiol* 36):F1021–F1033, 1994.
Hammond et al.,*Am J Physiol* 267:F516–F527, 1994.
Hammond et al., *J Clin Invest* 75:1983–1989, 1985.
Huang et al., *J Clin Invest* 99(4):732–736, 1997.
Iglesias et al., *Transplant Proc.* 26(1):75–6, 1994.
Imerslund, *Acta Paediatr. Scand.* 49 (Suppl), 1–115, 1960.
Jensen et al., *FEBS Lett.* 29, 129–32, 1992.
Jo et al., *Proc Natl Acad Sci USA* 92:1876–1880, 1995
Jonsson et al., *Biotechniques* 11:620–627, 1991.
Krieger et al., *Ann. Rev. Biochem.* 63, 601–637, 1994.
Le Panse et al., *Am. J. Pathol.* 145, 1526–36, 1994.
Le Panse et al., *Eur. J. Cell Biol.* 67, 120–9, 1995
Levi, *Essays in Biochemistry* 31, 49–59, 1996.
Llirbat et al., *J. Lipid Res.* 38:1 22–34, 1997.
Leung et al., *J. Exp. Med.* 156, 372–84, 1982.
Marchalonis et al., *J Prot Chem* 11(2):129–137, 1992.
Moestrup et al., *J. Biol. Chem.* 268,16564–16570, 1993.
Moestrup et al., *Biochimica et Biophys. Acta* 1197:197–213, 1994
Moestrup et al., *J Clin Invest* 96:1404–1413, 1995.
Nykjær et al., *EMBO J.* 16, 2610–2620, 1997.
O'Farrel P. H, *J. Biol Chem* 250:4007–4021, 1975.
Parvez et al., *Clin Chim Acta* 190(1-2):111–3, 1990.
Rao et al., *Cell* 82, 131–141, 1995.
Riedel et al., From: "Neoplastic diseases of the blood" Second Ed. Eds: Wiernik et al., Churchill Livingtone, 1991, Chap. 23:347–372.
Rothman et al., *Science* 272:227–234, 1996.
Rothman et al., *Current Biology* 4(3):220–233, 1994.
Sahali et al., *J Exp Med* 167:213–218, 1988.
Sahali et al., *Am J Pathol* 142:1654–1667, 1993.
Saito et al., *Proc Natl Acad Sci USA* 91:9725–9729, 1994.
Sanders et al., J. Clin. Invest. 82:2086–2096, 1988.
Tolkoff-Rubin et al., *Nephrol Dial Transplant* 2(3):143–8, 1987.
van der Merwe et al., *Curr Opin in Immunol* 8:257–261, 1996.
Yamamoto et al., *Cell* 39:27–38, 1984.
Willnow et al., *EMBO J.* 15, 2632–2639, 1996.
Winearls, *Kidney International* 48:1347–1360, 1995.
Zeidel et al., *Am J Physiol* 265:F822–F833, 1993.

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified cubilin protein, where said protein has an amino acid sequence shown in SEQ ID No. 2, and where said protein is encoded by DNA selected from the group consisting of:

(a) an isolated DNA which encodes a cubilin protein; and
   (b) an isolated DNA differing from the isolated DNA of (a) in codon sequence due to the degeneracy of the genetic code.

2. A composition comprising the protein or ligand binding fragment of claim 1 and a pharmaceutically acceptable carrier.

3. A receptor for ligands, where said receptor is the cubilin protein of claim 1 and where said receptor comprises a cluster of EGF repeats and a cluster of CUB domains.

4. The receptor of claim 3, wherein said ligand is selected from the group consisting of immunoglobulin light chain, myoglobin, intrinsic factor-vitamin $B_{12}$, metallothionein, $\beta$-2-microglobulin, amyloid, hemoglobin, haptoglobin, interferon, insulin, cytochrome c, lysozyme, transferrin, transthyretin, polybasic drugs, apolipoprotein Al, high density lipoprotein and receptor related protein.

5. The receptor of claim 4, wherein said immunoglobulin light chain is selected from the group consisting of $\kappa$-light chain and $\lambda$-light chain.

* * * * *

SEQUENCE LISTING

<160> NUMBER OF SEQ ID NOS: 40

<210> SEQ ID NO 1
<211> LENGTH: 11272
<212> TYPE: DNA
<213> ORGANISM: rat
<220> FEATURE:
<223> OTHER INFORMATION: nucleic acid sequence of rat cubilin

<400> SEQUENCE: 1
atgtcctcgc agtttctctg gggttttgtt actttgttga tgatagctga attagatggc      60

-continued

| | | | | | |
|---|---|---|---|---|---|
| aaaactggaa | agccggagca | gaggggacag | aaaaggatcg | ctgacctgca | ccagcctcgg | 120 |
| atgactacgg | aggagggaaa | cttagtattt | cttacaagct | ctacccaaaa | cattgaattt | 180 |
| agaactggat | ccctggggaa | aatcaaatta | aatgatgaag | accttggcga | atgtttacac | 240 |
| cagatccaga | gaaacaaaga | tgatattata | gatttaagaa | agaatacaac | tggcctccct | 300 |
| caaaatatac | ttagtcaagt | ccaccaactt | aactcgaagc | tcgtggatct | ggagagagat | 360 |
| tttcaaaact | tacagcagaa | tgtggagaga | aaagtttgca | gtagcaatcc | ctgccttaat | 420 |
| ggtggcacct | gcgtcaacct | gcacgactcc | tttgtgtgta | tctgcccttc | tcagtggaag | 480 |
| ggtctcttct | gctcagagga | tgtcaacgag | tgtgtagttt | actcaggaac | accctttggc | 540 |
| tgccagagtg | gatccacctg | tgtgaacaca | gtggggagtt | tcagatgtga | ctgcacgccg | 600 |
| gatacgtacg | gacctcagtg | tgcatccaaa | tataatgact | gtgaacaggg | ctctaaacag | 660 |
| ctctgcaagc | acggcatctg | tgaggattta | cagcgagttc | accatggaca | gccgaatttt | 720 |
| cactgcatct | gtgatgctgg | gtggacaaca | ccgccaaatg | gaatctcctg | cacagaggac | 780 |
| aaagacgaat | gcagcctcca | gccttcacct | tgttcggagc | atgcgcagtg | tttcaataca | 840 |
| caaggctcct | tctactgtgg | ggcctgcccc | aaaggttggc | agggaaatgg | ttatgaatgc | 900 |
| caggatatca | tgaatgcgca | gatcaacaat | ggaggctgtt | cccaggcgcc | actggtccca | 960 |
| tgcctgaaca | cacctggatc | attctcctgt | gggaactgtc | cagcaggttt | cagtggtgac | 1020 |
| gggagagtgt | gcactcccgt | ggacatctgt | tcgatccaca | atggaggctg | ccatccagag | 1080 |
| gcaacctgct | cctcatctcc | tgttctaggg | tccttcttgc | ctgtctgcac | ctgtcctccg | 1140 |
| ggatatacag | gaaatggtta | cggtctaat | ggatgtgtac | gcctcagtaa | tatttgctca | 1200 |
| aggcacccgt | gtgtaaatgg | acagtgcata | gaaacagtat | caagttattt | ctgtaagtgt | 1260 |
| gactcaggct | ggtctggaca | gaactgtaca | gaaaacatta | atgactgttc | gagcaacccc | 1320 |
| tgtttgaatg | ggggcacctg | tattgatggc | atcaatggct | tcacctgcga | ctgcacaagc | 1380 |
| tcttggactg | gctattactg | tcagactccc | caggcagctt | gcggagggat | cctctcaggg | 1440 |
| acacaaggaa | cctttgccta | ccacagccca | aatgataccc | atattcacaa | tgtgaactgt | 1500 |
| ttctggattg | tcagaactga | tgaggaaaag | gttctgcatg | tcaccttcac | gtttttttgat | 1560 |
| ttagaatcag | caagcaattg | tcccgggag | taccttcaga | ttcatgatgg | agactcctca | 1620 |
| gcggattcc | cacttggtag | atactgtggc | tccaggcccc | cccagggat | ccacagcagt | 1680 |
| gccaatgctc | tctatttcca | tctctactcc | gagtacataa | ggagtgggag | aggctttaca | 1740 |
| gcaaggtggg | aggcgaagct | gccagagtgt | ggcggcatcc | tgactgataa | ttacggttct | 1800 |
| attacgtctc | cggggtaccc | tggaaactac | cccccaggaa | gagattgtgt | ctggcaggtt | 1860 |
| ttagtcaatc | ctaactcctt | gataacattt | acctttggaa | ccttgagcct | ggagagccac | 1920 |
| aatgactgca | gcaaagacta | tttggagatt | cgagacggtc | cttccacca | agaccctgtt | 1980 |
| cttgggaaat | tctgcacttc | cttgtctacc | ccacccctca | agactaccgg | tcctgcagca | 2040 |
| agaattcatt | tccattctga | ctctgagacc | agtgacaaag | gcttccacat | cacctatcta | 2100 |
| accacacagt | cggatctgga | ctgtggtggg | aactacacag | acacggatgg | cgagctcctc | 2160 |
| cttcctcctt | tgtctggtcc | tttcagtcac | agcagacagt | gtgtctatct | catcacccaa | 2220 |
| gcccagggag | aacaaatagt | tatcaacttc | acccatgtgg | agctggagag | ccagatgggc | 2280 |
| tgttctcaca | cttacatcga | ggttggagac | catgacagct | acttcgaaa | gatctgtggc | 2340 |
| aatgaaacct | tgttccccat | tagatcagtt | tctaataaag | tctggatcag | attgagaata | 2400 |

```
gacgctttag tccagaaggc tagtttcaga gctgactacc aagttgcttg tgggggtatg    2460
ttaagaggag aaggattctt tcgctcacct ttctatccta acgcatatcc tggacgaaga    2520
acctgtaggt ggaccatctc ccaacccaa agacaagttg tccttcttaa cttcactgac     2580
tttcagatcg gaagttctgc ctcctgtgat acagattata ttgagattgg tcccagctct    2640
gtcttgggat ctcctggaaa tgagaagttt tgtagctcaa acataccgtc atttataaca    2700
tctgtataca atattcttta tgttacattt gtgaaaagtt cttccatgga aaatcgtggc    2760
ttcacggcta agttcagcag tgacaaacta gagtgtggag aagttctcac ggcatctaca    2820
ggaattatcg aaagtccagg tcatccaaac gtctacccaa gaggtgtaaa ttgtacttgg    2880
catgtagtag tccaacgcgg ccaactgatc cgtttggagt tcagttcctt ttacctggag    2940
tttcattaca actgcacaaa cgactacctg gaaatttatg acactgccgc tcagacttt    3000 cttgggagat actgtggaaa atccatcccg ccttctctta ccagcaactc taattcaata    3060
aagctgatat ttgtgtctga ctccgccctt gcccacgaag gcttttccat aaattatgag    3120
gcaatcgatg catcatcagt atgtttatat gactatacag ataattttgg gatgctctcc    3180
tccccgaact tccccaataa ttaccccagt aactgggagt gcatctacag aatcactgtg    3240
ggactcaacc aacagattgc attgcatttc acagacttca ccttggagga ctattttggg    3300
tcacagtgtg tagattttgt agaaatcaga gacggaggct acgaaacgtc gccgcttgtt    3360
gggatttact gtggctcagt tttgcctcct acaatcatct cccacagtaa caagctctgg    3420
ctaaagttta agagtgacgc cgcactcacg gcaaaggggt tctcagcgta ctgggacgga    3480
tcatcaacag gctgtggagg taatctcacc accccacagg tgctcacatc gcccaactac    3540
ccgatgccct actaccacag ctccgaatgc tactggcggc tggaagccag tcatggcagc    3600
cctttcgagc tggaattcca agacttccac ctggaacacc accccagctg ctctctggat    3660
tacttgggcc gtgttgatgg cccgactacc aactcccgac tgatagataa attgtgtggg    3720
gatacgacac ctgctcccat ccgttccaat aaagacgtcg tattgttaaa aactgaggaa    3780
ctgatgcaag gtcagctagg ccgtggcttt gagatcaact tccggcagag atgtgacaat    3840
gtggtgatag tgaacaaaac ctttggcatc ctggagagca taaattatcc aaatccctat    3900
gataagaacc aacgttgtaa ctggaccatc caagcaacca ccggcaacac cgtgaactac    3960
acgtttctgg gatttgatgt ggaaagttac atgaactgct ccacagatta tgtagagctc    4020
tatgatggac cacaatggat gggacgctac tgtggaaata acatgccccc accagggggct   4080 acaacaggct cccaactcca cgtactgttc catacagatg ggatcaattc tggggaaaaa    4140
ggatttaaga tgcagtggtt cactcatggc tgtggtggag agatgtctgg aaccgcaggc    4200
tccttcagca gccctgggta ccccaacagc tatcctcaca caaagagtg tatctggaac     4260 attcgcgtgg ccccagggag tagcattcag ctcaccatcc atgactttga tgtgaatat     4320 catacaagct gcaactatga ctccctggag atctatgcag gtcttgattt taactctcca    4380
agaatagccc aactgtgttc ccaatcaccg tcagcgaacc ccatgcaggt ctccagcact    4440
ggcaatgaac tagcaatccg atttaagacg gatagcactt taaatggaag aggtttcaat    4500
gcctcgtggc gagcagtccc tggaggttgt ggtggaatta ccagctttc cagaggagag     4560 attcattctc caaattaccc caacaactac agagctaaca cagagtgctc ctggatcatt    4620
caagttgagc gacatcaccg tgttctcttg aatatcactg actttgacct tgaagctcca    4680
gattcttgct tacgacttat ggatggctca agttccacaa acgcccgtgt cgccagtgtg    4740
tgtggaagac agcagccccc taactctatc atcgcttcag gaaacagcct ctttgtgaga    4800
```

```
ttccggtctg gatcttccag ccagaacagg ggcttccggg ctgaattcag ggaagagtgc   4860
ggaggccgca tcatgaccga ctcttccgat actatcttct ctccactgta ccctcacaac   4920
tatctacaca accagaactg ttcctggata attgaagctc agcctccatt caatcacatt   4980
actctctcct ttactcactt tcaacttcaa aacagcacag actgtacacg ggactttgta   5040
gaaattttgg atggcaacga ctatgacgca cctgtccaag gccgttactg tggtttctcc   5100
ctgccccacc ccatcatatc atttggcaat gccctaaccg tgaggtttgt cactgattcc   5160
acacgcagtt ttgagggttt ccgtgccatc tattctgcat cgacatcatc ttgtggtgga   5220
agcttctaca cacttgatgg catcttcaat agccccgact acccagcaga ctaccatcca   5280
aatgcagaat gtgtctggaa cattgccagc tcccctggca accgcctgca actgtccttc   5340
ctatccttca atttggagaa ttctctaaac tgtaacaagg attttgtgga atccgagaa    5400 ggaaatgcca cggccacttt gattggacga tactgtggaa actccctccc tgggaattat   5460
tcgtcagctg aggacatag tctatgggtc cgatttgtct ctgatggctc aggcactggc    5520
atgggcttcc aggccaggtt caaaaatata tttggcaata ataatattgt gggaactcat   5580
gggaaaatcg catctcccctt ctggcctgga aaatacccct acaactccaa ttacaaatgg   5640
gtggtaaatg tggacgcata tcatattatc cacggtagaa tcttagagat ggacatagaa   5700
cccacaacga actgctttta tgacagttta aagatttatg atggatttga cactcattcc   5760
cgtctcattg gcacttactg tggtacccag acagaatcct ttagctccag tagaaactat   5820
ctgacattcc agttttcttc cgactcttct gtgtcaggaa ggggattcct tctggagtgg   5880
tttgcagtag atgtttctga tagcacccct cccaccatcg ctccaggagc ttgtggaggg   5940
tttatggtga cgggagacac tcctgtccat attttctccc cgggttggcc tagagagtat   6000
gctaatggtg ctgactgtat ctggatcatc tatgctcctg actctactgt ggaactcaac   6060
attctctcct tggacatcga accgcagcag tcatgcaatt atgacaagct gatcgtaaaa   6120
gacggagaca gtgacttatc cccagagctg gctgttctgt gtggcgtaag ccctcctggg   6180
cccatccggt caactggaga atacatgtac atccgcttca cttcagacac cagcgtcgcg   6240
gggacaggct tcaacgcctc cttttcacaag agctgtggtg gatatttgca tgcagatcga   6300
ggagttatca catccccccaa gtatccagac acctaccttc ccaacctcaa ctgctcctgg   6360
catgttctgg tccagactgg tctgaccatc gccgtccatt ttgagcagcc tttccagatt   6420
caaaacagag actcttttg cagtcagggg gattacttgg tgctaagaaa cggaccagat   6480
aaccattctc caccactggg accttctgga agaaatggtc gtttctgcgg aatgtacgca   6540
ccgtccactc tgttcacctc aggcaatgaa atgtttgttc agttcatctc ggacagtagt   6600
aatggtggac aagggtttaa gatcagatat gaggcaaaga gtttagcctg cggggcact    6660 gtctacatcc atgatgctga ctctgacgga tacctgacct cccccaacta ccctgctaat   6720
tatccccaac atgccgaatg catttggatc ttagaggcgc ctccagggag aagcatacag   6780
ctccaatttg aagatcaatt caatattgaa gacacaccca actgttctgt gagctatctt   6840
gaattgcgtg acggagccaa ctcgaatgca cgtctggttt ccaagttgtg tggccacact   6900
ctgcctcata gctgggtatc ctcgagagaa cgaatatact tgaagtttca cactgacggt   6960
ggttccagct acatgggatt caaggccaag tactctatag cttcctgtgg aggaacagtc   7020
tcaggggaca gtggagtcat cgagagcatt ggctacccga cccttccgta tgcaaacaat   7080
gtgttttgtc agtggtttat ccgaggcctc ccaggacact acctcactct cagttttgaa   7140
```

```
gattttaacc ttcagagctc tcctggttgt acaaaagact ttgtggagat ctggaaaaac    7200
catacctctg gaagagttct ggggagatat tgtggaaact ccactcctag cagtgttgac    7260
acttccagca atgttgcttc cgtcaagttt gtcacagatg gctctgtcac tgcctcagga    7320
tttaggctgc agtttaagtc cagcagacaa gtgtgtggtg gggatttaca tggccctact    7380
ggcacattta cttctcccaa ctacccaaac ccaaatcctc atgcccggat ctgtgagtgg    7440
acgatcactg tacaagaagg aaggcggatc gtcctgacgt ttaccaactt gaggctgagt    7500
acccagccat cttgtaacag tgagcacctc atcgtattca atggcattag aagcaactcg    7560
cccctactac agaaactgtg cagccgtgtg aatgtgacca atgaattcaa atcttcagga    7620
aacaccatga aagtggtatt tttcactgat ggctcccggc cgtatggagg cttcactgct    7680
tcctacacct ctactgaaga tgcagtgtgt ggtggatttc ttccaagtgt ctccggtgga    7740 aactttctt ctcctggcta taatggaatc cgtgattatg ccagaaacct agactgtgaa    7800
tggactctca gtaatccaaa tcgggaaaat tcatccataa gtatctattt tctagaactt    7860
tccattgaaa gtcatcaaga ctgtacattt gatgtccttg agtttcgagt agggatgct    7920 gatgggcccc tgatagagaa gttctgtagc ctgtcagcac caacagcgcc cttggtcatc    7980 ccctacctc aggtgtggat acgcttcgtc agcaatgagc gtgtagaata tactggattc    8040
tatatagagt actcctttac agattgtggt ggaatacgga caggtgacaa tggagtgatc    8100
tcaagtccta actatccaaa cttgtacagt gcatggaccc actgttcatg gctgctgaaa    8160
gccccagaag ggcacaccat cactctcaca ctcagtgact ttcttctcga ggctcatcca    8220
acttgcactt cagactccgt cactgtcagg aatggtgact ccccaggatc gcccgtcata    8280
ggacgatact gtggacagtc agtcccaagg ccgatacagt ctggttccaa ccaacttata    8340
gtgactttta acacaaacaa tcaagggcaa actcgtggat tttatgcaac atggaccaca    8400
aacgctttag gttgtgggg aacattccac tcagctaatg gtacaatcaa atctcctcac    8460
tggcctcaga cattcccaga aaacagcaga tgctcctgga cagtgatcac tcacgatagt    8520
aaacactggg agattagctt tgacagcaat ttccgaatcc ccagcagtga cagccagtgt    8580
cagaacagct tcgtgaaggt ttggggaggc aggttgatga tcaataagac cctgttagcc    8640
acgagctgtg gagatgtggc tccaagtccc attgtcacat cagggaacat tttcactgct    8700
gtcttccaat ctgaggagat ggcagcccag ggcttctctg catccttcat tagccggtgc    8760
ggacgcacat tcaatacctc ccctggtgac atcatctctc caaacttccc gaagcaatac    8820
gacaacaaca tgaactgcac ctacctcata gacgctgacc ctcagtctct ggtcatcctg    8880
acttttgtgt cctttcattt ggaagatcgc tcagctatca ccggaacctg tgatcatgat    8940
ggcttgcaca tcatcaaagg tcgtaacctc tcttccactc ctctcgtgac catatgtggt    9000
tctgaaactt tgcgtcccct cactgtggac ggcccagtgt tgctcaactt ctattctgat    9060
gcatacacca cagactttgg cttcaagatt tcctacagag ccatcacctg tggtgggatc    9120
tacaatgaat cctctggaat ccttaggagc ccttcctact catacagcaa ctaccccaac    9180
aacctctact gtgtctacag cctccatgtt agaagcagca gagtgataat aattaggttc    9240
aatgatttcg atgtggctcc ttccaacctt tgtgcacatg acttcctgga ggtgtttgat    9300
ggtcccagca ttggaaatcg atctcttgga aagttctgtg gttccacgcg tccacaaact    9360
gttaagagca ccaatagcag cctgaccctc tgttcaaga cagattcttc tcaaacagca    9420
agaggttgga aaatatttt ccgggagaca atagggccac agcagggatg tggtggatac    9480
ctgaccgagg acaaccagag ctttgtgtct cctgattctg attcgaatgg acgctatgac    9540
```

```
aagggtctca gctgcatatg gtacatagtt gcacctgaaa acaaactggt taagctcacc    9600
ttcaatgtgt tcactctgga gggaccatcg tcagctggga gctgcgtcta tgattatgtg    9660
cagatagcag atggcgcaag cataaactca tatttaggtg gaaaattctg tggctcccgt    9720
atgcctgccc catttatctc ttccggctac ttccttacgt ttcagtttgt ctctgacgta    9780
actgttgaaa tgaggggatt taatgcaaca tatacctttg tggacatgcc ttgcggggga    9840
acatataacg caacctcgac acctcaaaat gcgtcatcac ctcatttatc caacatcgga    9900
cggccatact ccacctgtac ttgggtcatc gcagctcccc cacagcagca ggttcagata    9960
actgtgtggg acttacagct gccctcacaa gactgctcac aaagctactt agaacttcag   10020
gattcagtac agactggtgg aaaccgggtg actcagttct gcggtgcgaa ctatacaacc   10080
ttgccagtgt tctactcctc aatgagcact gcggttgtcg ttttcaagtc tggagttata   10140
aacagaaact cgcaagtgca attctcctat cagattgcag attgcaacag agaatacaac   10200
caaacgtttg gcaatctgaa gagtcctggg tggcctcaga actatgacaa taacctggac   10260
tgcaccatca ttctcagagc cccgcagaac cacagcattt ccctcttttt ctattggttt   10320
cagctggaag attcaagaca atgcatgaat gatttcttgg aggtaagaaa cggcggcagc   10380
agcacctcac cactgcttga caagtactgt agcaacctgc tgcccaaccc ggtcttctct   10440
cagagcaacg aactgtatct gcactttcac agcgaccact cagtcaccaa caatggctat   10500
gaaattattt ggacctcctc tgctgctggc tgtggaggga ctcttttggg cgacgaaggg   10560
atattcacca accctggctt tcctgacagt tacccgaaca cactcattg tgaatggacc    10620
attgttgctc cttctggaag gcctgtctct gtcgggtttc cctttctcag tatcgactct   10680
tctggtggct gtgaccagaa ctacctcata gtctttaatg gtccagacgc caactcccca   10740
cccttttggac cgttgtgtgg catcaacact gggatagcgc ccttctatgc ttcatcaaat   10800
cgggtctttta taaggtttca tgctgagtat acgacacgtc tttcagggtt tgaaataatg   10860
tggagcagct gaatcaggag agctgtgtat aaccccagga ctctggttct gcccagtgct   10920
gtcagatgca accctgccca gtactcattc tgctgttctc atccccgtct ctgcctgcgt   10980
catcaaacat ggactgagct tctacagcct tgaccagaga aagtgcacga ctgacttcat   11040
acattaggcg ttctgaaggc tttgatctac tcagctgtgc acaccatctt tactggatgc   11100
cctgtttagc cgacatcttc taaaatgttc tttaaagggt ggaagttatc ctggcacatt   11160
gatgtacggt tttaaaactt ggtgatacaa atggatgtat tgttccacta caaaagtcaa   11220
agtgcaggta ataacattc ttcacatgta aaaaaaaaa aaaaaaaaa aa              11272
```

<210> SEQ ID NO 2
<211> LENGTH: 3623
<212> TYPE: PRT
<213> ORGANISM: rat
<220> FEATURE:
<223> OTHER INFORMATION: amino acid sequence of rat cubilin protein
<400> SEQUENCE: 2

```
Met Ser Ser Gln Phe Leu Trp Gly Phe Val Thr Leu Leu Met Ile
              5                  10                  15

Ala Glu Leu Asp Gly Lys Thr Gly Lys Pro Glu Gln Arg Gly Gln
             20                  25                  30

Lys Arg Ile Ala Asp Leu Gly Gln Pro Arg Met Thr Thr Glu Glu
             35                  40                  45

Gly Asn Leu Val Phe Leu Thr Ser Ser Thr Gln Asn Ile Glu Phe
```

```
                        50                  55                  60
Arg Thr Gly Ser Leu Gly Lys Ile Lys Leu Asn Asp Glu Asp Leu
                65                  70                  75
Gly Glu Cys Leu Gly Gln Ile Gln Arg Asn Lys Asp Asp Ile Ile
                80                  85                  90
Asp Leu Arg Lys Asn Thr Thr Gly Leu Pro Gln Asn Ile Leu Ser
                95                  100                 105
Gln Val Gly Gln Leu Asn Ser Lys Leu Val Asp Leu Glu Arg Asp
                110                 115                 120
Phe Gln Asn Leu Gln Gln Asn Val Glu Arg Lys Val Cys Ser Ser
                125                 130                 135
Asn Pro Cys Leu Asn Gly Gly Thr Cys Val Asn Leu Gly Asp Ser
                140                 145                 150
Phe Val Cys Ile Cys Pro Ser Gln Trp Lys Gly Leu Phe Cys Ser
                155                 160                 165
Glu Asp Val Asn Glu Cys Val Val Tyr Ser Gly Thr Pro Phe Gly
                170                 175                 180
Cys Gln Ser Gly Ser Thr Cys Val Asn Thr Val Gly Ser Phe Arg
                185                 190                 195
Cys Asp Cys Thr Pro Asp Thr Tyr Gly Pro Gln Cys Ala Ser Lys
                200                 205                 210
Tyr Asn Asp Cys Glu Gln Gly Ser Lys Gln Leu Cys Lys Gly Gly
                215                 220                 225
Ile Cys Glu Asp Leu Gln Arg Val Gly Gly Gln Pro Asn Phe
                230                 235                 240
Gly Cys Ile Cys Asp Ala Gly Trp Thr Thr Pro Pro Asn Gly Ile
                245                 250                 255
Ser Cys Thr Glu Asp Lys Asp Glu Cys Ser Leu Gln Pro Ser Pro
                260                 265                 270
Cys Ser Glu Gly Ala Gln Cys Phe Asn Thr Gln Gly Ser Phe Tyr
                275                 280                 285
Cys Gly Ala Cys Pro Lys Gly Trp Gln Gly Asn Gly Tyr Glu Cys
                290                 295                 300
Gln Asp Ile Asn Glu Cys Glu Ile Asn Asn Gly Gly Cys Ser Gln
                305                 310                 315
Ala Pro Leu Val Pro Cys Leu Asn Thr Pro Gly Ser Phe Ser Cys
                320                 325                 330
Gly Asn Cys Pro Ala Gly Phe Ser Gly Asp Gly Arg Val Cys Thr
                335                 340                 345
Pro Val Asp Ile Cys Ser Ile Gly Asn Gly Gly Cys Gly Pro Glu
                350                 355                 360
Ala Thr Cys Ser Ser Pro Val Leu Gly Ser Phe Leu Pro Val
                365                 370                 375
Cys Thr Cys Pro Pro Gly Tyr Thr Gly Asn Gly Tyr Gly Ser Asn
                380                 385                 390
Gly Cys Val Arg Leu Ser Asn Ile Cys Ser Arg Gly Pro Cys Val
                395                 400                 405
Asn Gly Gln Cys Ile Glu Thr Val Ser Ser Tyr Phe Cys Lys Cys
                410                 415                 420
Asp Ser Gly Trp Ser Gly Gln Asn Cys Thr Glu Asn Ile Asn Asp
                425                 430                 435
Cys Ser Ser Asn Pro Cys Leu Asn Gly Gly Thr Cys Ile Asp Gly
                440                 445                 450
```

-continued

```
Ile Asn Gly Phe Thr Cys Asp Cys Thr Ser Ser Trp Thr Gly Tyr
            455                 460                 465
Tyr Cys Gln Thr Pro Gln Ala Ala Cys Gly Gly Ile Leu Ser Gly
            470                 475                 480
Thr Gln Gly Thr Phe Ala Tyr Gly Ser Pro Asn Asp Thr Tyr Ile
            485                 490                 495
Gly Asn Val Asn Cys Phe Trp Ile Val Arg Thr Asp Glu Glu Lys
            500                 505                 510
Val Leu Gly Val Thr Phe Thr Phe Phe Asp Leu Glu Ser Ala Ser
            515                 520                 525
Asn Cys Pro Arg Glu Tyr Leu Gln Ile Gly Asp Gly Asp Ser Ser
            530                 535                 540
Ala Asp Phe Pro Leu Gly Arg Tyr Cys Gly Ser Arg Pro Pro Gln
            545                 550                 555
Gly Ile Gly Ser Ser Ala Asn Ala Leu Tyr Phe Gly Leu Tyr Ser
            560                 565                 570
Glu Tyr Ile Arg Ser Gly Arg Gly Phe Thr Ala Arg Trp Glu Ala
            575                 580                 585
Lys Leu Pro Glu Cys Gly Gly Ile Leu Thr Asp Asn Tyr Gly Ser
            590                 595                 600
Ile Thr Ser Pro Gly Tyr Pro Gly Asn Tyr Pro Pro Gly Arg Asp
            605                 610                 615
Cys Val Trp Gln Val Leu Val Asn Pro Asn Ser Leu Ile Thr Phe
            620                 625                 630
Thr Phe Gly Thr Leu Ser Leu Glu Ser Gly Asn Asp Cys Ser Lys
            635                 640                 645
Asp Tyr Leu Glu Ile Arg Asp Gly Pro Phe Gly Gln Asp Pro Val
            650                 655                 660
Leu Gly Lys Phe Cys Thr Ser Leu Ser Thr Pro Pro Leu Lys Thr
            665                 670                 675
Thr Gly Pro Ala Ala Arg Ile Gly Phe Gly Ser Asp Ser Glu Thr
            680                 685                 690
Ser Asp Lys Gly Phe Gly Ile Thr Tyr Leu Thr Thr Gln Ser Asp
            695                 700                 705
Leu Asp Cys Gly Gly Asn Tyr Thr Asp Thr Asp Gly Glu Leu Leu
            710                 715                 720
Leu Pro Pro Leu Ser Gly Pro Phe Ser Gly Ser Arg Gln Cys Val
            725                 730                 735
Tyr Leu Ile Thr Gln Ala Gln Gly Glu Gln Ile Val Ile Asn Phe
            740                 745                 750
Thr Gly Val Glu Leu Glu Ser Gln Met Gly Cys Ser Gly Thr Tyr
            755                 760                 765
Ile Glu Val Gly Asp Gly Asp Ser Leu Leu Arg Lys Ile Cys Gly
            770                 775                 780
Asn Glu Thr Leu Phe Pro Ile Arg Ser Val Ser Asn Lys Val Trp
            785                 790                 795
Ile Arg Leu Arg Ile Asp Ala Leu Val Gln Lys Ala Ser Phe Arg
            800                 805                 810
Ala Asp Tyr Gln Val Ala Cys Gly Gly Met Leu Arg Gly Glu Gly
            815                 820                 825
Phe Phe Arg Ser Pro Phe Tyr Pro Asn Ala Tyr Pro Gly Arg Arg
            830                 835                 840
```

-continued

```
Thr Cys Arg Trp Thr Ile Ser Gln Pro Gln Arg Gln Val Val Leu
                845                 850                 855

Leu Asn Phe Thr Asp Phe Gln Ile Gly Ser Ser Ala Ser Cys Asp
                860                 865                 870

Thr Asp Tyr Ile Glu Ile Gly Pro Ser Ser Val Leu Gly Ser Pro
                875                 880                 885

Gly Asn Glu Lys Phe Cys Ser Ser Asn Ile Pro Ser Phe Ile Thr
                890                 895                 900

Ser Val Tyr Asn Ile Leu Tyr Val Thr Phe Val Lys Ser Ser Ser
                905                 910                 915

Met Glu Asn Arg Gly Phe Thr Ala Lys Phe Ser Ser Asp Lys Leu
                920                 925                 930

Glu Cys Gly Glu Val Leu Thr Ala Ser Thr Gly Ile Ile Glu Ser
                935                 940                 945

Pro Gly Gly Pro Asn Val Tyr Pro Arg Gly Val Asn Cys Thr Trp
                950                 955                 960

Gly Val Val Val Gln Arg Gly Gln Leu Ile Arg Leu Glu Phe Ser
                965                 970                 975

Ser Phe Tyr Leu Glu Phe Gly Tyr Asn Cys Thr Asn Asp Tyr Leu
                980                 985                 990

Glu Ile Tyr Asp Thr Ala Ala Gln Thr Phe Leu Gly Arg Tyr Cys
                995                 1000                1005

Gly Lys Ser Ile Pro Pro Ser Leu Thr Ser Asn Ser Asn Ser Ile
                1010                1015                1020

Lys Leu Ile Phe Val Ser Asp Ser Ala Leu Ala Gly Glu Gly Phe
                1025                1030                1035

Ser Ile Asn Tyr Glu Ala Ile Asp Ala Ser Ser Val Cys Leu Tyr
                1040                1045                1050

Asp Tyr Thr Asp Asn Phe Gly Met Leu Ser Ser Pro Asn Phe Pro
                1055                1060                1065

Asn Asn Tyr Pro Ser Asn Trp Glu Cys Ile Tyr Arg Ile Thr Val
                1070                1075                1080

Gly Leu Asn Gln Gln Ile Ala Leu Gly Phe Thr Asp Phe Thr Leu
                1085                1090                1095

Glu Asp Tyr Phe Gly Ser Gln Cys Val Asp Phe Val Glu Ile Arg
                1100                1105                1110

Asp Gly Gly Tyr Glu Thr Ser Pro Leu Val Gly Ile Tyr Cys Gly
                1115                1120                1125

Ser Val Leu Pro Pro Thr Ile Ile Ser Gly Ser Asn Lys Leu Trp
                1130                1135                1140

Leu Lys Phe Lys Ser Asp Ala Ala Leu Thr Ala Lys Gly Phe Ser
                1145                1150                1155

Ala Tyr Trp Asp Gly Ser Ser Thr Gly Cys Gly Gly Asn Leu Thr
                1160                1165                1170

Thr Pro Gln Val Leu Thr Ser Pro Asn Tyr Pro Met Pro Tyr Tyr
                1175                1180                1185

Gly Ser Ser Glu Cys Tyr Trp Arg Leu Glu Ala Ser Gly Gly Ser
                1190                1195                1200

Pro Phe Glu Leu Glu Phe Gln Asp Phe Gly Leu Glu Gly Gly Pro
                1205                1210                1215

Ser Cys Ser Leu Asp Tyr Leu Gly Arg Val Asp Gly Pro Thr Thr
                1220                1225                1230

Asn Ser Arg Leu Ile Asp Lys Leu Cys Gly Asp Thr Thr Pro Ala
```

-continued

```
            1235                1240                1245

Pro Ile Arg Ser Asn Lys Asp Val Val Leu Leu Lys Thr Glu Glu
            1250                1255                1260

Leu Met Gln Gly Gln Leu Gly Arg Gly Phe Glu Ile Asn Phe Arg
            1265                1270                1275

Gln Arg Cys Asp Asn Val Val Ile Val Asn Lys Thr Phe Gly Ile
            1280                1285                1290

Leu Glu Ser Ile Asn Tyr Pro Asn Pro Tyr Asp Lys Asn Gln Arg
            1295                1300                1305

Cys Asn Trp Thr Ile Gln Ala Thr Thr Gly Asn Thr Val Asn Tyr
            1310                1315                1320

Thr Phe Leu Gly Phe Asp Val Glu Ser Tyr Met Asn Cys Ser Thr
            1325                1330                1335

Asp Tyr Val Glu Leu Tyr Asp Gly Pro Gln Trp Met Gly Arg Tyr
            1340                1345                1350

Cys Gly Asn Asn Met Pro Pro Gly Ala Thr Thr Gly Ser Gln
            1355                1360                1365

Leu Gly Val Leu Phe Gly Thr Asp Gly Ile Asn Ser Gly Glu Lys
            1370                1375                1380

Gly Phe Lys Met Gln Trp Phe Thr Gly Gly Cys Gly Gly Glu Met
            1385                1390                1395

Ser Gly Thr Ala Gly Ser Phe Ser Ser Pro Gly Tyr Pro Asn Ser
            1400                1405                1410

Tyr Pro Gly Asn Lys Glu Cys Ile Trp Asn Ile Arg Val Ala Pro
            1415                1420                1425

Gly Ser Ser Ile Gln Leu Thr Ile Gly Asp Phe Asp Val Glu Tyr
            1430                1435                1440

Gly Thr Ser Cys Asn Tyr Asp Ser Leu Glu Ile Tyr Ala Gly Leu
            1445                1450                1455

Asp Phe Asn Ser Pro Arg Ile Ala Gln Leu Cys Ser Gln Ser Pro
            1460                1465                1470

Ser Ala Asn Pro Met Gln Val Ser Ser Thr Gly Asn Glu Leu Ala
            1475                1480                1485

Ile Arg Phe Lys Thr Asp Ser Thr Leu Asn Gly Arg Gly Phe Asn
            1490                1495                1500

Ala Ser Trp Arg Ala Val Pro Gly Gly Cys Gly Gly Ile Ile Gln
            1505                1510                1515

Leu Ser Arg Gly Glu Ile Gly Ser Pro Asn Tyr Pro Asn Asn Tyr
            1520                1525                1530

Arg Ala Asn Thr Glu Cys Ser Trp Ile Ile Gln Val Glu Arg Gly
            1535                1540                1545

Gly Arg Val Leu Leu Asn Ile Thr Asp Phe Asp Leu Glu Ala Pro
            1550                1555                1560

Asp Ser Cys Leu Arg Leu Met Asp Gly Ser Ser Thr Asn Ala
            1565                1570                1575

Arg Val Ala Ser Val Cys Gly Arg Gln Gln Pro Pro Asn Ser Ile
            1580                1585                1590

Ile Ala Ser Gly Asn Ser Leu Phe Val Arg Phe Arg Ser Gly Ser
            1595                1600                1605

Ser Ser Gln Asn Arg Gly Phe Arg Ala Glu Phe Arg Glu Glu Cys
            1610                1615                1620

Gly Gly Arg Ile Met Thr Asp Ser Ser Asp Thr Ile Phe Ser Pro
            1625                1630                1635
```

-continued

```
Leu Tyr Pro Gly Asn Tyr Leu Gly Asn Gln Asn Cys Ser Trp Ile
            1640                1645                1650
Ile Glu Ala Gln Pro Pro Phe Asn Gly Ile Thr Leu Ser Phe Thr
            1655                1660                1665
Gly Phe Gln Leu Gln Asn Ser Thr Asp Cys Thr Arg Asp Phe Val
            1670                1675                1680
Glu Ile Leu Asp Gly Asn Asp Tyr Asp Ala Pro Val Gln Gly Arg
            1685                1690                1695
Tyr Cys Gly Phe Ser Leu Pro Gly Pro Ile Ile Ser Phe Gly Asn
            1700                1705                1710
Ala Leu Thr Val Arg Phe Val Thr Asp Ser Thr Arg Ser Phe Glu
            1715                1720                1725
Gly Phe Arg Ala Ile Tyr Ser Ala Ser Thr Ser Ser Cys Gly Gly
            1730                1735                1740
Ser Phe Tyr Thr Leu Asp Gly Ile Phe Asn Ser Pro Asp Tyr Pro
            1745                1750                1755
Ala Asp Tyr Gly Pro Asn Ala Glu Cys Val Trp Asn Ile Ala Ser
            1760                1765                1770
Ser Pro Gly Asn Arg Leu Gln Leu Ser Phe Leu Ser Phe Asn Leu
            1775                1780                1785
Glu Asn Ser Leu Asn Cys Asn Lys Asp Phe Val Glu Ile Arg Glu
            1790                1795                1800
Gly Asn Ala Thr Gly Gly Leu Ile Gly Arg Tyr Cys Gly Asn Ser
            1805                1810                1815
Leu Pro Gly Asn Tyr Ser Ser Ala Glu Gly Gly Ser Leu Trp Val
            1820                1825                1830
Arg Phe Val Ser Asp Gly Ser Gly Thr Gly Met Gly Phe Gln Ala
            1835                1840                1845
Arg Phe Lys Asn Ile Phe Gly Asn Asn Ile Val Gly Thr Gly
            1850                1855                1860
Gly Lys Ile Ala Ser Pro Phe Trp Pro Gly Lys Tyr Pro Tyr Asn
            1865                1870                1875
Ser Asn Tyr Lys Trp Val Val Asn Val Asp Ala Tyr Gly Ile Ile
            1880                1885                1890
Gly Gly Arg Ile Leu Glu Met Asp Ile Glu Pro Thr Thr Asn Cys
            1895                1900                1905
Phe Tyr Asp Ser Leu Lys Ile Tyr Asp Gly Phe Asp Thr Gly Ser
            1910                1915                1920
Arg Leu Ile Gly Thr Tyr Cys Gly Thr Gln Thr Glu Ser Phe Ser
            1925                1930                1935
Ser Ser Arg Asn Tyr Leu Thr Phe Gln Phe Ser Ser Asp Ser Ser
            1940                1945                1950
Val Ser Gly Arg Gly Phe Leu Leu Glu Trp Phe Ala Val Asp Val
            1955                1960                1965
Ser Asp Ser Thr Pro Pro Thr Ile Ala Pro Gly Ala Cys Gly Gly
            1970                1975                1980
Phe Met Val Thr Gly Asp Thr Pro Val Gly Ile Phe Ser Pro Gly
            1985                1990                1995
Trp Pro Arg Glu Tyr Ala Asn Gly Ala Asp Cys Ile Trp Ile Ile
            2000                2005                2010
Tyr Ala Pro Asp Ser Thr Val Glu Leu Asn Ile Leu Ser Leu Asp
            2015                2020                2025
```

-continued

```
Ile Glu Pro Gln Gln Ser Cys Asn Tyr Asp Lys Leu Ile Val Lys
            2030                2035                2040

Asp Gly Asp Ser Asp Leu Ser Pro Glu Leu Ala Val Leu Cys Gly
            2045                2050                2055

Val Ser Pro Pro Gly Pro Ile Arg Ser Thr Gly Glu Tyr Met Tyr
            2060                2065                2070

Ile Arg Phe Thr Ser Asp Thr Ser Val Ala Gly Thr Gly Phe Asn
            2075                2080                2085

Ala Ser Phe Gly Lys Ser Cys Gly Gly Tyr Leu Gly Ala Asp Arg
            2090                2095                2100

Gly Val Ile Thr Ser Pro Lys Tyr Pro Asp Thr Tyr Leu Pro Asn
            2105                2110                2115

Leu Asn Cys Ser Trp Gly Val Leu Val Gln Thr Gly Leu Thr Ile
            2120                2125                2130

Ala Val Gly Phe Glu Gln Pro Phe Gln Ile Gln Asn Arg Asp Ser
            2135                2140                2145

Phe Cys Ser Gln Gly Asp Tyr Leu Val Leu Arg Asn Gly Pro Asp
            2150                2155                2160

Asn Gly Ser Pro Pro Leu Gly Pro Ser Gly Arg Asn Gly Arg Phe
            2165                2170                2175

Cys Gly Met Tyr Ala Pro Ser Thr Leu Phe Thr Ser Gly Asn Glu
            2180                2185                2190

Met Phe Val Gln Phe Ile Ser Asp Ser Ser Asn Gly Gly Gln Gly
            2195                2200                2205

Phe Lys Ile Arg Tyr Glu Ala Lys Ser Leu Ala Cys Gly Gly Thr
            2210                2215                2220

Val Tyr Ile Gly Asp Ala Asp Ser Asp Gly Tyr Leu Thr Ser Pro
            2225                2230                2235

Asn Tyr Pro Ala Asn Tyr Pro Gln Gly Ala Glu Cys Ile Trp Ile
            2240                2245                2250

Leu Glu Ala Pro Pro Gly Arg Ser Ile Gln Leu Gln Phe Glu Asp
            2255                2260                2265

Gln Phe Asn Ile Glu Asp Thr Pro Asn Cys Ser Val Ser Tyr Leu
            2270                2275                2280

Glu Leu Arg Asp Gly Ala Asn Ser Asn Ala Arg Leu Val Ser Lys
            2285                2290                2295

Leu Cys Gly Gly Thr Leu Pro Gly Ser Trp Val Ser Ser Arg Glu
            2300                2305                2310

Arg Ile Tyr Leu Lys Phe Gly Thr Asp Gly Gly Ser Ser Tyr Met
            2315                2320                2325

Gly Phe Lys Ala Lys Tyr Ser Ile Ala Ser Cys Gly Gly Thr Val
            2330                2335                2340

Ser Gly Asp Ser Gly Val Ile Glu Ser Ile Gly Tyr Pro Thr Leu
            2345                2350                2355

Pro Tyr Ala Asn Asn Val Phe Cys Gln Trp Phe Ile Arg Gly Leu
            2360                2365                2370

Pro Gly Gly Tyr Leu Thr Leu Ser Phe Glu Asp Phe Asn Leu Gln
            2375                2380                2385

Ser Ser Pro Gly Cys Thr Lys Asp Phe Val Glu Ile Trp Glu Asn
            2390                2395                2400

Gly Thr Ser Gly Arg Val Leu Gly Arg Tyr Cys Gly Asn Ser Thr
            2405                2410                2415

Pro Ser Ser Val Asp Thr Ser Ser Asn Val Ala Ser Val Lys Phe
```

-continued

```
                    2420                2425                2430
Val Thr Asp Gly Ser Val Thr Ala Ser Gly Phe Arg Leu Gln Phe
                2435                2440                2445
Lys Ser Ser Arg Gln Val Cys Gly Gly Asp Leu Gly Gly Pro Thr
                2450                2455                2460
Gly Thr Phe Thr Ser Pro Asn Tyr Pro Asn Pro Asn Pro Gly Ala
                2465                2470                2475
Arg Ile Cys Glu Trp Thr Ile Thr Val Gln Glu Gly Arg Arg Ile
                2480                2485                2490
Val Leu Thr Phe Thr Asn Leu Arg Leu Ser Thr Gln Pro Ser Cys
                2495                2500                2505
Asn Ser Glu Gly Leu Ile Val Phe Asn Gly Ile Arg Ser Asn Ser
                2510                2515                2520
Pro Leu Leu Gln Lys Leu Cys Ser Arg Val Asn Val Thr Asn Glu
                2525                2530                2535
Phe Lys Ser Ser Gly Asn Thr Met Lys Val Val Phe Phe Thr Asp
                2540                2545                2550
Gly Ser Arg Pro Tyr Gly Gly Phe Thr Ala Ser Tyr Thr Ser Thr
                2555                2560                2565
Glu Asp Ala Val Cys Gly Gly Phe Leu Pro Ser Val Ser Gly Gly
                2570                2575                2580
Asn Phe Ser Ser Pro Gly Tyr Asn Gly Ile Arg Asp Tyr Ala Arg
                2585                2590                2595
Asn Leu Asp Cys Glu Trp Thr Leu Ser Asn Pro Asn Arg Glu Asn
                2600                2605                2610
Ser Ser Ile Ser Ile Tyr Phe Leu Glu Leu Ser Ile Glu Ser Gly
                2615                2620                2625
Gln Asp Cys Thr Phe Asp Val Leu Glu Phe Arg Val Gly Asp Ala
                2630                2635                2640
Asp Gly Pro Leu Ile Glu Lys Phe Cys Ser Leu Ser Ala Pro Thr
                2645                2650                2655
Ala Pro Leu Val Ile Pro Tyr Pro Gln Val Trp Ile Arg Phe Val
                2660                2665                2670
Ser Asn Glu Arg Val Glu Tyr Thr Gly Phe Tyr Ile Glu Tyr Ser
                2675                2680                2685
Phe Thr Asp Cys Gly Gly Ile Arg Thr Gly Asp Asn Gly Val Ile
                2690                2695                2700
Ser Ser Pro Asn Tyr Pro Asn Leu Tyr Ser Ala Trp Thr Gly Cys
                2705                2710                2715
Ser Trp Leu Leu Lys Ala Pro Glu Gly Gly Thr Ile Thr Leu Thr
                2720                2725                2730
Leu Ser Asp Phe Leu Leu Glu Ala Gly Pro Thr Cys Thr Ser Asp
                2735                2740                2745
Ser Val Thr Val Arg Asn Gly Asp Ser Pro Gly Ser Pro Val Ile
                2750                2755                2760
Gly Arg Tyr Cys Gly Gln Ser Val Pro Arg Pro Ile Gln Ser Gly
                2765                2770                2775
Ser Asn Gln Leu Ile Val Thr Phe Asn Thr Asn Asn Gln Gly Gln
                2780                2785                2790
Thr Arg Gly Phe Tyr Ala Thr Trp Thr Asn Ala Leu Gly Cys
                2795                2800                2805
Gly Gly Thr Phe Gly Ser Ala Asn Gly Thr Ile Lys Ser Pro Gly
                2810                2815                2820
```

```
Trp Pro Gln Thr Phe Pro Glu Asn Ser Arg Cys Ser Trp Thr Val
            2825                2830                2835

Ile Thr Gly Asp Ser Lys Gly Trp Glu Ile Ser Phe Asp Ser Asn
            2840                2845                2850

Phe Arg Ile Pro Ser Ser Asp Ser Gln Cys Gln Asn Ser Phe Val
            2855                2860                2865

Lys Val Trp Gly Gly Arg Leu Met Ile Asn Lys Thr Leu Leu Ala
            2870                2875                2880

Thr Ser Cys Gly Asp Val Ala Pro Ser Pro Ile Val Thr Ser Gly
            2885                2890                2895

Asn Ile Phe Thr Ala Val Phe Gln Ser Glu Glu Met Ala Ala Gln
            2900                2905                2910

Gly Phe Ser Ala Ser Phe Ile Ser Arg Cys Gly Arg Thr Phe Asn
            2915                2920                2925

Thr Ser Pro Gly Asp Ile Ile Ser Pro Asn Phe Pro Lys Gln Tyr
            2930                2935                2940

Asp Asn Asn Met Asn Cys Thr Tyr Leu Ile Asp Ala Asp Pro Gln
            2945                2950                2955

Ser Leu Val Ile Leu Thr Phe Val Ser Phe Gly Leu Glu Asp Arg
            2960                2965                2970

Ser Ala Ile Thr Gly Thr Cys Asp Gly Asp Gly Leu Gly Ile Ile
            2975                2980                2985

Lys Gly Arg Asn Leu Ser Ser Thr Pro Leu Val Thr Ile Cys Gly
            2990                2995                3000

Ser Glu Thr Leu Arg Pro Leu Thr Val Asp Gly Pro Val Leu Leu
            3005                3010                3015

Asn Phe Tyr Ser Asp Ala Tyr Thr Thr Asp Phe Gly Phe Lys Ile
            3020                3025                3030

Ser Tyr Arg Ala Ile Thr Cys Gly Gly Ile Tyr Asn Glu Ser Ser
            3035                3040                3045

Gly Ile Leu Arg Ser Pro Ser Tyr Ser Tyr Ser Asn Tyr Pro Asn
            3050                3055                3060

Asn Leu Tyr Cys Val Tyr Ser Leu Gly Val Arg Ser Ser Arg Val
            3065                3070                3075

Ile Ile Ile Arg Phe Asn Asp Phe Asp Val Ala Pro Ser Asn Leu
            3080                3085                3090

Cys Ala Gly Asp Phe Leu Glu Val Phe Asp Gly Pro Ser Ile Gly
            3095                3100                3105

Asn Arg Ser Leu Gly Lys Phe Cys Gly Ser Thr Arg Pro Gln Thr
            3110                3115                3120

Val Lys Ser Thr Asn Ser Ser Leu Thr Leu Leu Phe Lys Thr Asp
            3125                3130                3135

Ser Ser Gln Thr Ala Arg Gly Trp Lys Ile Phe Phe Arg Glu Thr
            3140                3145                3150

Ile Gly Pro Gln Gln Gly Cys Gly Gly Tyr Leu Thr Glu Asp Asn
            3155                3160                3165

Gln Ser Phe Val Ser Pro Asp Ser Asp Ser Asn Gly Arg Tyr Asp
            3170                3175                3180

Lys Gly Leu Ser Cys Ile Trp Tyr Ile Val Ala Pro Glu Asn Lys
            3185                3190                3195

Leu Val Lys Leu Thr Phe Asn Val Phe Thr Leu Glu Gly Pro Ser
            3200                3205                3210
```

-continued

```
Ser Ala Gly Ser Cys Val Tyr Asp Tyr Val Gln Ile Ala Asp Gly
            3215                3220                3225

Ala Ser Ile Asn Ser Tyr Leu Gly Gly Lys Phe Cys Gly Ser Arg
            3230                3235                3240

Met Pro Ala Pro Phe Ile Ser Ser Gly Tyr Phe Leu Thr Phe Gln
            3245                3250                3255

Phe Val Ser Asp Val Thr Val Glu Met Arg Gly Phe Asn Ala Thr
            3260                3265                3270

Tyr Thr Phe Val Asp Met Pro Cys Gly Gly Thr Tyr Asn Ala Thr
            3275                3280                3285

Ser Thr Pro Gln Asn Ala Ser Ser Pro Gly Leu Ser Asn Ile Gly
            3290                3295                3300

Arg Pro Tyr Ser Thr Cys Thr Trp Val Ile Ala Ala Pro Pro Gln
            3305                3310                3315

Gln Gln Val Gln Ile Thr Val Trp Asp Leu Gln Leu Pro Ser Gln
            3320                3325                3330

Asp Cys Ser Gln Ser Tyr Leu Glu Leu Gln Asp Ser Val Gln Thr
            3335                3340                3345

Gly Gly Asn Arg Val Thr Gln Phe Cys Gly Ala Asn Tyr Thr Thr
            3350                3355                3360

Leu Pro Val Phe Tyr Ser Ser Met Ser Thr Ala Val Val Val Phe
            3365                3370                3375

Lys Ser Gly Val Ile Asn Arg Asn Ser Gln Val Gln Phe Ser Tyr
            3380                3385                3390

Gln Ile Ala Asp Cys Asn Arg Glu Tyr Asn Gln Thr Phe Gly Asn
            3395                3400                3405

Leu Lys Ser Pro Gly Trp Pro Gln Asn Tyr Asp Asn Asn Leu Asp
            3410                3415                3420

Cys Thr Ile Ile Leu Arg Ala Pro Gln Asn Gly Ser Ile Ser Leu
            3425                3430                3435

Phe Phe Tyr Trp Phe Gln Leu Glu Asp Ser Arg Gln Cys Met Asn
            3440                3445                3450

Asp Phe Leu Glu Val Arg Asn Gly Gly Ser Ser Thr Ser Pro Leu
            3455                3460                3465

Leu Asp Lys Tyr Cys Ser Asn Leu Leu Pro Asn Pro Val Phe Ser
            3470                3475                3480

Gln Ser Asn Glu Leu Tyr Leu Gly Phe Gly Ser Asp Gly Ser Val
            3485                3490                3495

Thr Asn Asn Gly Tyr Glu Ile Ile Trp Thr Ser Ser Ala Ala Gly
            3500                3505                3510

Cys Gly Gly Thr Leu Leu Gly Asp Glu Gly Ile Phe Thr Asn Pro
            3515                3520                3525

Gly Phe Pro Asp Ser Tyr Pro Asn Asn Thr Gly Cys Glu Trp Thr
            3530                3535                3540

Ile Val Ala Pro Ser Gly Arg Pro Val Ser Val Gly Phe Pro Phe
            3545                3550                3555

Leu Ser Ile Asp Ser Ser Gly Gly Cys Asp Gln Asn Tyr Leu Ile
            3560                3565                3570

Val Phe Asn Gly Pro Asp Ala Asn Ser Pro Pro Phe Gly Pro Leu
            3575                3580                3585

Cys Gly Ile Asn Thr Gly Ile Ala Pro Phe Tyr Ala Ser Ser Asn
            3590                3595                3600

Arg Val Phe Ile Arg Phe Gly Ala Glu Tyr Thr Thr Arg Leu Ser
```

```
                         3605                    3610                    3615
Gly Phe Glu Ile Met Trp Ser Ser
                        3620

<210> SEQ ID NO 3
<211> LENGTH: 22
<212> TYPE: DNA
<213> ORGANISM: artificial sequence
<220> FEATURE:
<221> NAME/KEY: primer_bind
<222> LOCATION: bps 838-859 of rat cubilin
<223> OTHER INFORMATION: primer for 5' RACE

<400> SEQUENCE: 3
acacaaggct ccttctactg tg                                                    22

<210> SEQ ID NO 4
<211> LENGTH: 20
<212> TYPE: DNA
<213> ORGANISM: artificial sequence
<220> FEATURE:
<221> NAME/KEY: primer_bind
<222> LOCATION: bps 6872-6891 of rat cubilin
<223> OTHER INFORMATION: primer for 3' RACE

<400> SEQUENCE: 4
gtctggtttc caagttgtgt                                                       20

<210> SEQ ID NO 5
<211> LENGTH: 21
<212> TYPE: DNA
<213> ORGANISM: artificial sequence
<220> FEATURE:
<221> NAME/KEY: primer_bind
<222> LOCATION: bps 7152-7172 of rat cubilin
<223> OTHER INFORMATION: primer for 3' RACE

<400> SEQUENCE: 5
tcagagctct cctggttgta c                                                     21

<210> SEQ ID NO 6
<211> LENGTH: 36
<212> TYPE: PRT
<213> ORGANISM: rat
<220> FEATURE:
<223> OTHER INFORMATION: amino acid sequence of rat cubilin EGF1 repeat

<400> SEQUENCE: 6

Arg Lys Val Cys Ser Ser Asn Pro Cys Leu Asn Gly Gly Thr Cys
                 5                  10                  15

Val Asn Leu His Asp Ser Phe Val Cys Ile Cys Pro Ser Gln Trp
                20                  25                  30

Lys Gly Leu Phe Cys Ser
                35

<210> SEQ ID NO 7
<211> LENGTH: 43
<212> TYPE: PRT
<213> ORGANISM: rat
<220> FEATURE:
<223> OTHER INFORMATION: amino acid sequence of rat cubilin EGF2 repeat

<400> SEQUENCE: 7

Glu Asp Val Asn Glu Cys Val Val Tyr Ser Gly Thr Pro Phe Gly
                 5                  10                  15
```

-continued

```
Cys Gln Ser Gly Ser Thr Cys Val Asn Thr Val Gly Ser Phe Arg
                20                  25                  30

Cys Asp Cys Thr Pro Asp Thr Tyr Gly Pro Gln Cys Ala
                35                  40

<210> SEQ ID NO 8
<211> LENGTH: 50
<212> TYPE: PRT
<213> ORGANISM: rat
<220> FEATURE:
<223> OTHER INFORMATION: amino acid sequence of rat cubilin EGF3 repeat

<400> SEQUENCE: 8

Ser Lys Tyr Asn Asp Cys Glu Gln Gly Ser Lys Gln Leu Cys Lys
                5                   10                  15

His Gly Ile Cys Glu Asp Leu Gln Arg Val His His Gly Gln Pro
                20                  25                  30

Asn Phe His Cys Ile Cys Asp Ala Gly Trp Thr Thr Pro Pro Asn
                35                  40                  45

Gly Ile Ser Cys Thr
                50

<210> SEQ ID NO 9
<211> LENGTH: 43
<212> TYPE: PRT
<213> ORGANISM: rat
<220> FEATURE:
<223> OTHER INFORMATION: amino acid sequence of rat cubilin EGF4 repeat

<400> SEQUENCE: 9

Glu Asp Lys Asp Glu Cys Ser Leu Gln Pro Ser Pro Cys Ser Glu
                5                   10                  15

His Ala Gln Cys Phe Asn Thr Gln Gly Ser Phe Tyr Cys Gly Ala
                20                  25                  30

Cys Pro Lys Gly Trp Gln Gly Asn Gly Tyr Glu Cys Gln
                35                  40

<210> SEQ ID NO 10
<211> LENGTH: 44
<212> TYPE: PRT
<213> ORGANISM: rat
<220> FEATURE:
<223> OTHER INFORMATION: amino acid sequence of rat cubilin EGF5 repeat

<400> SEQUENCE: 10

Asp Ile Asn Lys Cys Glu Ile Asn Asn Gly Gly Cys Ser Gln Ala
                5                   10                  15

Pro Leu Val Pro Cys Leu Asn Thr Pro Gly Ser Phe Ser Cys Gly
                20                  25                  30

Asn Cys Pro Ala Gly Phe Ser Gly Asp Gly Arg Val Cys Thr
                35                  40

<210> SEQ ID NO 11
<211> LENGTH: 48
<212> TYPE: PRT
<213> ORGANISM: rat
<220> FEATURE:
<223> OTHER INFORMATION: amino acid sequence of rat cubilin EGF6 repeat

<400> SEQUENCE: 11

Pro Val Asp Ile Cys Ser Ile His Asn Gly Gly Cys His Pro Glu
                5                   10                  15
```

```
Ala Thr Cys Ser Ser Ser Pro Val Leu Gly Ser Phe Leu Pro Val
                20                  25                  30

Cys Thr Cys Pro Pro Gly Tyr Thr Gly Asn Gly Tyr Gly Ser Asn
                35                  40                  45

Gly Cys Val

<210> SEQ ID NO 12
<211> LENGTH: 37
<212> TYPE: PRT
<213> ORGANISM: rat
<220> FEATURE:
<223> OTHER INFORMATION: amino acid sequence of rat cubilin EGF7 repeat

<400> SEQUENCE: 12

Arg Leu Ser Asn Ile Cys Ser Arg His Pro Cys Val Asn Gly Gln
                 5                  10                  15

Cys Ile Glu Thr Val Ser Ser Tyr Phe Cys Lys Cys Asp Ser Gly
                20                  25                  30

Trp Ser Gly Gln Asn Cys Thr
                35

<210> SEQ ID NO 13
<211> LENGTH: 38
<212> TYPE: PRT
<213> ORGANISM: rat
<220> FEATURE:
<223> OTHER INFORMATION: amino acid sequence of rat cubilin EGF8 repeat

<400> SEQUENCE: 13

Glu Asn Ile Asn Asp Cys Ser Ser Asn Pro Cys Leu Asn Gly Gly
                 5                  10                  15

Thr Cys Ile Asp Gly Ile Asn Gly Phe Thr Cys Asp Cys Thr Ser
                20                  25                  30

Ser Trp Thr Gly Tyr Tyr Cys Gln
                35

<210> SEQ ID NO 14
<211> LENGTH: 42
<212> TYPE: PRT
<213> ORGANISM: human
<220> FEATURE:
<223> OTHER INFORMATION: amino acid sequence of Bmp-1 EGF1 repeat

<400> SEQUENCE: 14

Glu Val Asp Glu Cys Ser Arg Pro Asn Arg Gly Gly Cys Glu Gln
                 5                  10                  15

Arg Cys Leu Asn Thr Leu Gly Ser Tyr Lys Cys Ser Cys Asp Pro
                20                  25                  30

Gly Tyr Glu Leu Ala Pro Asp Lys Arg Arg Cys Glu
                35                  40

<210> SEQ ID NO 15
<211> LENGTH: 41
<212> TYPE: PRT
<213> ORGANISM: Drosophila
<220> FEATURE:
<223> OTHER INFORMATION: amino acid sequence of Tolloid EGF1 repeat

<400> SEQUENCE: 15

Asp Val Asp Glu Cys Lys Phe Thr Asp His Gly Cys Gln His Leu
                 5                  10                  15

Cys Ile Asn Thr Leu Gly Ser Tyr Gln Cys Gly Cys Arg Ala Gly
```

```
                      20                  25                  30

Tyr Glu Leu Gln Ala Asn Gly Lys Thr Cys Glu
                35                  40

<210> SEQ ID NO 16
<211> LENGTH: 41
<212> TYPE: PRT
<213> ORGANISM: Drosophila
<220> FEATURE:
<223> OTHER INFORMATION: amino acid sequence of Tolloid EGF2 repeat

<400> SEQUENCE: 16

Asp Val Asp Glu Cys Ser Met Asn Asn Gly Gly Cys Gln His Arg
                 5                  10                  15

Cys Arg Asn Thr Phe Gly Ser Tyr Gln Cys Ser Cys Arg Asn Gly
                20                  25                  30

Tyr Thr Leu Ala Glu Asn Gly His Asn Cys Thr
                35                  40

<210> SEQ ID NO 17
<211> LENGTH: 42
<212> TYPE: PRT
<213> ORGANISM: human
<220> FEATURE:
<223> OTHER INFORMATION: amino acid sequence of C1s EGF1 repeat

<400> SEQUENCE: 17

Asp Ile Asn Glu Cys Thr Asp Phe Val Asp Val Pro Cys Ser His
                 5                  10                  15

Phe Cys Asn Asn Phe Ile Gly Gly Tyr Phe Cys Ser Cys Pro Pro
                20                  25                  30

Glu Tyr Phe Leu His Asp Asp Met Lys Asn Cys Gly
                35                  40

<210> SEQ ID NO 18
<211> LENGTH: 42
<212> TYPE: PRT
<213> ORGANISM: human
<220> FEATURE:
<223> OTHER INFORMATION: amino acid sequence of fibrillin-1 EGF5 repeat

<400> SEQUENCE: 18

Asp Ile Asp Glu Cys Ser Thr Ile Pro Gly Ile Cys Glu Gly Gly
                 5                  10                  15

Glu Cys Thr Asn Thr Val Ser Ser Tyr Phe Cys Lys Cys Pro Pro
                20                  25                  30

Gly Phe Tyr Thr Ser Pro Asp Gly Thr Arg Cys Ile
                35                  40

<210> SEQ ID NO 19
<211> LENGTH: 41
<212> TYPE: PRT
<213> ORGANISM: human
<220> FEATURE:
<223> OTHER INFORMATION: amino acid sequence of fibrillin-1 EGF13 repeat

<400> SEQUENCE: 19

Asp Ile Asp Glu Cys Glu Ser Ser Pro Cys Ile Asn Gly Val Cys
                 5                  10                  15

Lys Asn Ser Pro Gly Ser Phe Ile Cys Glu Cys Ser Ser Glu Ser
                20                  25                  30

Thr Leu Asp Pro Lys Thr Lys Thr Ile Cys Ile
```

-continued

```
                 35                  40

<210> SEQ ID NO 20
<211> LENGTH: 41
<212> TYPE: PRT
<213> ORGANISM: human
<220> FEATURE:
<223> OTHER INFORMATION: amino acid sequence of fibrillin-1 EGF26 repeat

<400> SEQUENCE: 20

Asp Val Asn Glu Cys Leu Asp Pro Thr Thr Cys Ile Ser Gly Asn
                 5                  10                  15

Cys Val Asn Thr Pro Gly Ser Tyr Ile Cys Asp Cys Pro Pro Asp
                20                  25                  30

Phe Glu Leu Asn Pro Thr Arg Val Gly Cys Val
                35                  40

<210> SEQ ID NO 21
<211> LENGTH: 110
<212> TYPE: PRT
<213> ORGANISM: rat
<220> FEATURE:
<223> OTHER INFORMATION: amino acid sequence of rat cubilin CUB2 domain

<400> SEQUENCE: 21

Cys Gly Gly Ile Leu Thr Asp Asn Tyr Gly Ser Ile Thr Ser Pro
                 5                  10                  15

Gly Tyr Pro Gly Asn Tyr Pro Pro Gly Arg Asp Cys Val Trp Gln
                20                  25                  30

Val Leu Val Asn Pro Asn Ser Leu Ile Thr Phe Thr Phe Gly Thr
                35                  40                  45

Leu Ser Leu Glu Ser His Asn Asp Cys Ser Lys Asp Tyr Leu Glu
                50                  55                  60

Ile Arg Asp Gly Pro Phe His Gln Asp Pro Val Leu Gly Lys Phe
                65                  70                  75

Cys Thr Ser Leu Ser Thr Pro Pro Leu Lys Thr Thr Gly Pro Ala
                80                  85                  90

Ala Arg Ile His Gly His Ser Cys Ser Glu Thr Ser Asp Lys Gly
                95                 100                 105

Phe His Ile Thr Tyr
                110

<210> SEQ ID NO 22
<211> LENGTH: 108
<212> TYPE: PRT
<213> ORGANISM: rat
<220> FEATURE:
<223> OTHER INFORMATION: amino acid sequence of rat cubilin CUB5 domain

<400> SEQUENCE: 22

Cys Gly Glu Val Leu Thr Ala Ser Thr Gly Ile Ile Glu Ser Pro
                 5                  10                  15

Gly His Pro Asn Val Tyr Pro Arg Gly Val Asn Cys Thr Trp His
                20                  25                  30

Val Val Val Gln Arg Gly Gln Leu Ile Arg Leu Glu Phe Ser Ser
                35                  40                  45

Phe Tyr Leu Glu Phe His Tyr Asn Cys Thr Asn Asp Tyr Leu Glu
                50                  55                  60

Ile Tyr Asp Thr Ala Ala Gln Thr Phe Leu Gly Arg Tyr Cys Gly
                65                  70                  75
```

```
Lys Ser Ile Pro Pro Ser Leu Thr Ser Asn Ser Asn Ser Ile Lys
                80                  85                  90

Leu Ile Phe Val Ser Asp Ser Ala Leu Ala His Glu Phe Gly Ser
                95                 100                 105

Ile Asn Tyr

<210> SEQ ID NO 23
<211> LENGTH: 111
<212> TYPE: PRT
<213> ORGANISM: rat
<220> FEATURE:
<223> OTHER INFORMATION: amino acid sequence of rat cubilin CUB6 domain

<400> SEQUENCE: 23

Cys Leu Tyr Asp Tyr Thr Asp Asn Phe Gly Met Leu Ser Ser Pro
                 5                  10                  15

Asn Phe Pro Asn Asn Tyr Pro Ser Asn Trp Glu Cys Ile Tyr Arg
                20                  25                  30

Ile Thr Val Gly Leu Asn Gln Gln Ile Ala Leu His Phe Thr Asp
                35                  40                  45

Phe Thr Leu Glu Asp Tyr Phe Gly Ser Gln Cys Val Asp Phe Val
                50                  55                  60

Glu Ile Arg Asp Gly Gly Tyr Glu Thr Ser Pro Leu Val Gly Ile
                65                  70                  75

Tyr Cys Gly Ser Val Leu Pro Pro Thr Ile Ile Ser His Ser Asn
                80                  85                  90

Lys Leu Trp Leu Lys Phe Lys Ser Asp Ala Ala Leu Thr Ala Lys
                95                 100                 105

Gly Phe Ser Ala Tyr Trp
                110

<210> SEQ ID NO 24
<211> LENGTH: 113
<212> TYPE: PRT
<213> ORGANISM: rat
<220> FEATURE:
<223> OTHER INFORMATION: amino acid sequence of rat cubilin CUB9 domain

<400> SEQUENCE: 24

Cys Gly Gly Glu Met Ser Gly Thr Ala Gly Ser Phe Ser Ser Pro
                 5                  10                  15

Gly Tyr Pro Asn Ser Tyr Pro His Asn Lys Glu Cys Ile Trp Asn
                20                  25                  30

Ile Arg Val Ala Pro Gly Ser Ser Ile Gln Leu Thr Ile His Asp
                35                  40                  45

Phe Asp Val Glu Tyr His Thr Ser Cys Asn Tyr Asp Ser Leu Glu
                50                  55                  60

Ile Tyr Ala Gly Leu Asp Phe Asn Ser Pro Arg Ile Ala Gln Leu
                65                  70                  75

Cys Ser Gln Ser Pro Ser Ala Asn Pro Met Gln Val Ser Ser Thr
                80                  85                  90

Gly Asn Glu Leu Ala Ile Arg Phe Lys Thr Asp Ser Thr Leu Asn
                95                 100                 105

Gly Arg Gly Phe Asn Ala Ser Trp
                110

<210> SEQ ID NO 25
```

-continued

```
<211> LENGTH: 110
<212> TYPE: PRT
<213> ORGANISM: rat
<220> FEATURE:
<223> OTHER INFORMATION: amino acid sequence of rat cubilin CUB12 domain

<400> SEQUENCE: 25

Cys Gly Gly Ser Phe Tyr Thr Leu Asp Gly Ile Phe Asn Ser Pro
                 5                  10                  15

Asp Tyr Pro Ala Asp Tyr His Gly Asn Ala Glu Cys Val Trp Asn
                20                  25                  30

Ile Ala Ser Ser Pro Gly Asn Arg Leu Gln Leu Ser Phe Leu Ser
                35                  40                  45

Phe Asn Leu Glu Asn Ser Leu Asn Cys Asn Lys Asp Phe Val Glu
                50                  55                  60

Ile Arg Glu Gly Asn Ala Thr Gly His Leu Ile Gly Arg Tyr Cys
                65                  70                  75

Gly Asn Ser Leu Pro Gly Asn Tyr Ser Ser Ala Glu Gly His Ser
                80                  85                  90

Leu Trp Val Arg Phe Val Ser Asp Gly Ser Gly Thr Gly Met Gly
                95                  100                 105

Phe Gln Ala Arg Phe
                110

<210> SEQ ID NO 26
<211> LENGTH: 110
<212> TYPE: PRT
<213> ORGANISM: rat
<220> FEATURE:
<223> OTHER INFORMATION: amino acid sequence of rat cubilin CUB17 domain

<400> SEQUENCE: 26

Cys Gly Gly Thr Val Ser Gly Asp Ser Gly Val Ile Glu Ser Ile
                 5                  10                  15

Gly Tyr Pro Thr Leu Pro Tyr Ala Asn Asn Val Phe Cys Gln Trp
                20                  25                  30

Phe Ile Arg Gly Leu Pro Gly His Tyr Leu Thr Leu Ser Phe Glu
                35                  40                  45

Asp Phe Asn Leu Gln Ser Ser Pro Gly Cys Thr Lys Asp Phe Val
                50                  55                  60

Glu Ile Trp Glu Asn His Thr Ser Gly Arg Val Leu Gly Arg Tyr
                65                  70                  75

Cys Gly Asn Ser Thr Pro Ser Ser Val Asp Thr Ser Ser Asn Val
                80                  85                  90

Ala Ser Val Lys Arg Val Thr Asp Gly Ser Val Thr Ala Ser Gly
                95                  100                 105

Phe Arg Leu Gln Phe
                110

<210> SEQ ID NO 27
<211> LENGTH: 110
<212> TYPE: PRT
<213> ORGANISM: rat
<220> FEATURE:
<223> OTHER INFORMATION: amino acid sequence of rat cubilin CUB20 domain

<400> SEQUENCE: 27

Cys Gly Gly Ile Arg Thr Gly Asp Asn Gly Val Ile Ser Ser Pro
                 5                  10                  15
```

```
Asn Tyr Pro Asn Leu Tyr Ser Ala Trp Thr His Cys Ser Trp Leu
                20                  25                  30

Leu Lys Ala Pro Glu Gly His Thr Ile Thr Leu Thr Leu Ser Asp
                35                  40                  45

Phe Leu Leu Glu Ala His Pro Thr Cys Thr Ser Asp Ser Val Thr
                50                  55                  60

Val Arg Asn Gly Asp Ser Pro Gly Ser Pro Val Ile Gly Arg Tyr
                65                  70                  75

Cys Gly Gln Ser Val Pro Arg Pro Ile Gln Ser Gly Ser Asn Gln
                80                  85                  90

Leu Ile Val Thr Phe Asn Thr Asn Gln Gly Gln Thr Arg Gly
                95                 100                 105

Phe Tyr Ala Thr Trp
                110
```

<210> SEQ ID NO 28
<211> LENGTH: 110
<212> TYPE: PRT
<213> ORGANISM: human
<220> FEATURE:
<223> OTHER INFORMATION: amino acid sequence of Bmp-1 CUB1 domain

<400> SEQUENCE: 28

```
Cys Gly Glu Thr Leu Gln Asp Ser Thr Gly Asn Phe Ser Ser Pro
                 5                  10                  15

Glu Tyr Pro Asn Gly Tyr Ser Ala His Met His Cys Val Trp Arg
                20                  25                  30

Ile Ser Val Thr Pro Gly Glu Lys Ile Ile Leu Asn Phe Thr Ser
                35                  40                  45

Leu Asp Leu Tyr Arg Ser Arg Leu Cys Trp Tyr Asp Tyr Val Glu
                50                  55                  60

Val Arg Asp Gly Phe Trp Arg Lys Ala Pro Leu Arg Gly Arg Phe
                65                  70                  75

Cys Gly Ser Lys Leu Pro Glu Pro Ile Val Ser Thr Asp Ser Arg
                80                  85                  90

Leu Trp Val Glu Phe Arg Ser Ser Ser Asn Trp Val Gly Lys Gly
                95                 100                 105

Phe Phe Ala Val Tyr
                110
```

<210> SEQ ID NO 29
<211> LENGTH: 110
<212> TYPE: PRT
<213> ORGANISM: human
<220> FEATURE:
<223> OTHER INFORMATION: amino acid sequence of Bmp-1 CUB2 domain

<400> SEQUENCE: 29

```
Cys Gly Gly Asp Val Lys Lys Asp Tyr Gly His Ile Gln Ser Pro
                 5                  10                  15

Asn Tyr Pro Asp Asp Tyr Arg Pro Ser Lys Val Cys Ile Trp Arg
                20                  25                  30

Ile Gln Val Ser Glu Gly Phe His Val Gly Leu Thr Phe Gln Ser
                35                  40                  45

Phe Glu Ile Glu Arg His Asp Ser Cys Ala Tyr Asp Tyr Leu Glu
                50                  55                  60

Val Arg Asp Gly His Ser Glu Ser Ser Thr Leu Ile Gly Arg Tyr
                65                  70                  75
```

```
Cys Gly Tyr Glu Lys Pro Asp Asp Ile Lys Ser Thr Ser Ser Arg
                80                  85                  90

Leu Trp Leu Lys Phe Val Ser Asp Gly Ser Ile Asn Lys Ala Gly
                95                  100                 105

Phe Ala Val Asn Phe
                110
```

<210> SEQ ID NO 30
<211> LENGTH: 111
<212> TYPE: PRT
<213> ORGANISM: Drosphila
<220> FEATURE:
<223> OTHER INFORMATION: amino acid sequence of Tolloid CUB2 domain

<400> SEQUENCE: 30

```
Cys Gly Gly Asp Leu Lys Leu Thr Lys Asp Gln Ser Ile Asp Ser
                5                   10                  15

Pro Asn Tyr Pro Met Asp Tyr Met Pro Asp Lys Glu Cys Val Trp
                20                  25                  30

Arg Ile Thr Ala Ala Pro Asp Asn His Gln Val Ala Leu Lys Phe
                35                  40                  45

Gln Ser Phe Glu Leu Glu Lys His Asp Gly Cys Ala Tyr Asp Phe
                50                  55                  60

Val Glu Ile Arg Asp Gly Asn His Ser Asp Ser Arg Leu Ile Gly
                65                  70                  75

Arg Phe Cys Gly Lys Leu Pro Pro Asn Ile Lys Thr Arg Ser Asn
                80                  85                  90

Gln Met Tyr Ile Arg Phe Val Ser Asp Ser Ser Val Gln Lys Leu
                95                  100                 105

Gly Phe Ser Ala Ala Leu
                110
```

<210> SEQ ID NO 31
<211> LENGTH: 116
<212> TYPE: PRT
<213> ORGANISM: Drosphila
<220> FEATURE:
<223> OTHER INFORMATION: amino acid sequence of Tolloid CUB3 domain

<400> SEQUENCE: 31

```
Cys Gly Gly Val Val Asp Ala Thr Lys Ser Asn Gly Ser Leu Tyr
                5                   10                  15

Ser Pro Ser Tyr Pro Asp Val Tyr Pro Asn Ser Lys Gln Cys Val
                20                  25                  30

Trp Glu Val Val Ala Pro Pro Asn His Ala Val Phe Leu Asn Phe
                35                  40                  45

Ser His Phe Asp Leu Glu Gly Thr Arg Phe His Tyr Thr Lys Cys
                50                  55                  60

Asn Tyr Asp Tyr Leu Ile Ile Tyr Ser Lys Met Arg Asp Asn Arg
                65                  70                  75

Leu Lys Lys Ile Gly Ile Tyr Cys Gly His Glu Leu Pro Pro Val
                80                  85                  90

Val Asn Ser Glu Gln Ser Ile Leu Arg Leu Glu Phe Tyr Ser Asp
                95                  100                 105

Arg Thr Val Gln Arg Ser Gly Phe Val Lys Phe
                110                 115
```

```
<210> SEQ ID NO 32
<211> LENGTH: 109
<212> TYPE: PRT
<213> ORGANISM: Drosphila
<220> FEATURE:
<223> OTHER INFORMATION: amino acid sequence of Tolloid CUB4 domain

<400> SEQUENCE: 32

Cys Lys Phe Glu Ile Thr Thr Ser Tyr Gly Val Leu Gln Ser Pro
                 5                  10                  15

Asn Tyr Pro Glu Asp Tyr Pro Arg Asn Ile Tyr Cys Tyr Trp His
                20                  25                  30

Phe Gln Thr Val Leu Gly Phe Ile Gln Leu Thr Phe His Asp Phe
                35                  40                  45

Glu Val Glu Ser His Gln Glu Cys Ile Tyr Asp Tyr Val Ala Ile
                50                  55                  60

Tyr Asp Gly Arg Ser Glu Asn Ser Ser Thr Leu Gly Ile Tyr Cys
                65                  70                  75

Gly Gly Arg Glu Pro Tyr Ala Val Ile Ala Ser Thr Asn Glu Met
                80                  85                  90

Phe Met Val Leu Ala Thr Asp Ala Gly Leu Gln Arg Lys Gly Phe
                95                 100                 105

Lys Ala Thr Phe

<210> SEQ ID NO 33
<211> LENGTH: 109
<212> TYPE: PRT
<213> ORGANISM: Xenopus laevis
<220> FEATURE:
<223> OTHER INFORMATION: amino acid sequence of Uvs-2 CUB2 domain

<400> SEQUENCE: 33

Cys Gly Gly Ala Phe Tyr Ser Ser Pro Lys Thr Phe Thr Ser Pro
                 5                  10                  15

Asn Tyr Pro Gly Asn Tyr Thr Thr Asn Thr Asn Cys Thr Trp Thr
                20                  25                  30

Ile Thr Ala Pro Ala Gly Phe Lys Val Ser Leu Arg Ile Thr Asp
                35                  40                  45

Phe Glu Leu Glu Ile Gly Ala Ser Cys Arg Tyr Asp Tyr Leu Asn
                50                  55                  60

Ile Tyr Asn Ser Thr Leu Gly Ala Val Met Gly Pro Tyr Cys Gly
                65                  70                  75

Pro Ile Asp Phe His Ser Ala Ile Val Ser Lys Ser Asn Ser Met
                80                  85                  90

Met Ile Thr Met Asn Ser Asp Phe Ser Lys Gln Tyr Lys Gly Phe
                95                 100                 105

Ser Ala Thr Tyr

<210> SEQ ID NO 34
<211> LENGTH: 112
<212> TYPE: PRT
<213> ORGANISM: human
<220> FEATURE:
<223> OTHER INFORMATION: amino acid sequence of C1s CUB1 domain

<400> SEQUENCE: 34

Glu Pro Thr Met Tyr Gly Glu Ile Leu Ser Pro Asn Tyr Pro Gln
                 5                  10                  15

Ala Tyr Pro Ser Glu Val Glu Lys Ser Trp Asp Ile Glu Val Pro
```

-continued

```
                       20                  25                  30

Glu Gly Tyr Gly Ile His Leu Tyr Phe Thr His Leu Asp Ile Glu
                35                  40                  45

Leu Ser Glu Asn Cys Ala Tyr Asp Ser Val Gln Ile Ile Ser Gly
            50                  55                  60

Asp Thr Glu Glu Gly Arg Leu Cys Gly Gln Arg Ser Ser Asn Asn
        65                  70                  75

Pro His Ser Pro Ile Val Glu Glu Phe Gln Val Pro Tyr Asn Lys
                80                  85                  90

Leu Gln Val Ile Phe Lys Ser Asp Phe Ser Asn Glu Glu Arg Phe
                95                 100                 105

Thr Gly Phe Ala Ala Tyr Tyr
                110

<210> SEQ ID NO 35
<211> LENGTH: 109
<212> TYPE: PRT
<213> ORGANISM: human
<220> FEATURE:
<223> OTHER INFORMATION: amino acid sequence of Tsg6 CUB domain

<400> SEQUENCE: 35

Cys Gly Gly Val Gly Thr Asp Pro Lys Arg Ile Phe Lys Ser Pro
                 5                  10                  15

Gly Phe Pro Asn Glu Tyr Glu Asp Asn Gln Ile Cys Tyr Trp His
                20                  25                  30

Ile Arg Leu Lys Tyr Gly Gln Arg Ile His Leu Ser Phe Leu Asp
                35                  40                  45

Phe Asp Leu Glu Asp Asp Pro Gly Cys Leu Ala Asp Tyr Val Glu
                50                  55                  60

Ile Tyr Asp Ser Tyr Asp Asp Val His Gly Phe Val Gly Arg Tyr
            65                  70                  75

Cys Gly Asp Glu Leu Pro Asp Asp Ile Ile Ser Gly Asn Val Met
            80                  85                  90

Thr Leu Lys Phe Leu Ser Asp Ala Ser Val Thr Ala Gly Gly Phe
                95                 100                 105

Gln Ile Lys Tyr

<210> SEQ ID NO 36
<211> LENGTH: 98
<212> TYPE: PRT
<213> ORGANISM: pig
<220> FEATURE:
<223> OTHER INFORMATION: amino acid sequence of Aqn-3 CUB domain

<400> SEQUENCE: 36

Cys Gly Gly Phe Leu Lys Asn Tyr Ser Gly Trp Ile Ser Tyr Tyr
                 5                  10                  15

Lys Ala Leu Thr Thr Asn Cys Val Trp Thr Ile Glu Met Lys Pro
                20                  25                  30

Gly His Lys Ile Ile Leu Gln Ile Leu Pro Leu Asn Leu Thr Cys
            35                  40                  45

Lys Glu Tyr Leu Glu Val Arg Asp Gln Arg Ala Gly Pro Asp Asn
                50                  55                  60

Phe Leu Lys Val Cys Gly Gly Thr Gly Phe Val Tyr Gln Ser Ser
            65                  70                  75

His Asn Val Ala Thr Val Lys Tyr Ser Arg Asp Ser His His Pro
```

```
                    80                  85                  90
Ala Ser Ser Phe Asn Val Tyr Phe
                95
```

<210> SEQ ID NO 37
<211> LENGTH: 21
<212> TYPE: DNA
<213> ORGANISM: artificial sequence
<220> FEATURE:
<221> NAME/KEY: primer_bind
<223> OTHER INFORMATION: a cubilin primer used for RT-PCR

<400> SEQUENCE: 37
tgcctaccac agcccaaatg a                                          21

<210> SEQ ID NO 38
<211> LENGTH: 19
<212> TYPE: DNA
<213> ORGANISM: artificial sequence
<220> FEATURE:
<221> NAME/KEY: primer_bind
<223> OTHER INFORMATION: a cubilin primer used for RT-PCR

<400> SEQUENCE: 38
agagccacaa tgactgcag                                             19

<210> SEQ ID NO 39
<211> LENGTH: 22
<212> TYPE: DNA
<213> ORGANISM: artificial sequence
<220> FEATURE:
<221> NAME/KEY: primer_bind
<223> OTHER INFORMATION: a megalin primer used for RT-PCR

<400> SEQUENCE: 39
gccagggaga caggaacagt ag                                         22

<210> SEQ ID NO 40
<211> LENGTH: 22
<212> TYPE: DNA
<213> ORGANISM: artificial sequence
<220> FEATURE:
<221> NAME/KEY: primer_bind
<223> OTHER INFORMATION: a megalin primer used for RT-PCR

<400> SEQUENCE: 40
tcacaaaatg ccagaccacg aa                                         22